United States Patent
Amano et al.

(10) Patent No.: US 6,241,684 B1
(45) Date of Patent: *Jun. 5, 2001

(54) EXERCISE WORKOUT SUPPORT DEVICE

(75) Inventors: Kazuhiko Amano, Suwa; Kazuo Uebaba, Yokohama; Hitoshi Ishiyama, Toride, all of (JP)

(73) Assignee: Seiko Epson Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,267

(22) PCT Filed: Apr. 8, 1997

(86) PCT No.: PCT/JP97/01193

§ 371 Date: Feb. 2, 1998

§ 102(e) Date: Feb. 2, 1998

(87) PCT Pub. No.: WO97/37588

PCT Pub. Date: Oct. 16, 1997

(30) Foreign Application Priority Data

| Apr. 8, 1996 | (JP) | ................................................ 8-085555 |
| Nov. 15, 1996 | (JP) | ................................................ 8-305318 |

(51) Int. Cl.⁷ ........................................................ A61B 5/00
(52) U.S. Cl. ........................... 600/531; 600/529; 600/503
(58) Field of Search ................................... 600/300–301, 600/481–485, 500–503, 529–538; 128/897–899

(56) References Cited

U.S. PATENT DOCUMENTS

| 4,312,358 | 1/1982 | Barney . |
| 4,367,752 | 1/1983 | Jimenez et al. . |
| 4,408,613 | 10/1983 | Relyea . |
| 4,434,801 | 3/1984 | Jiminez et al. . |
| 4,566,461 | * 1/1986 | Lubell et al. ........................ 128/668 |
| 5,001,632 | 3/1991 | Hall-Tipping . |
| 5,301,154 | 4/1994 | Suga . |
| 5,515,858 | * 5/1996 | Myllymaki ........................... 600/503 |
| 5,853,351 | * 1/1998 | Mauro et al. ............................ 482/8 |
| 5,857,465 | * 1/1999 | Nakamura et al. .................. 600/503 |

FOREIGN PATENT DOCUMENTS

| 0 556 702 | 8/1993 | (EP) . |
| 2 685 189 | 6/1993 | (FR) . |
| WO 86/02538 | 5/1986 | (WO) . |

* cited by examiner

*Primary Examiner*—Eric F. Winakur
*Assistant Examiner*—Michael Astorino

(57) ABSTRACT

A device is provided, which is capable of determining the maximum oxygen uptake quantity without the restriction of a large device or requiring troublesome operations to be carried out. The device displays the upper and lower limit values for the pulse rate corresponding to an appropriate exercise intensity, and realizes in a wireless manner by means of optical communications the sending and receiving of information such as pulse wave signals to and from an information processing device which processes pulse wave information. The device is provided with a pulse wave detector 101 for detecting the test subject s pulse waveform; an FFT processor 103 for determining the test subject s heartbeat rate from the pulse waveform; a body motion detector 104 for detecting body motion when the test subject is running; an FFT processor 106 for determining the pitch from body motion during running by the test subject; exercise intensity calculator 108 for determining pitch, the test subject s stride, and the exercise intensity from body motion during running; and a nomogram recorder 109 for recording the relationship indicated by an Astrand-Ryhming nomogram, and determining the maximum oxygen uptake quantity from the heart rate and exercise intensity. The obtained maximum oxygen uptake quantity is divided by the test subject s body weight, to calculate the maximum oxygen uptake quantity per unit body weight. Next, the maximum oxygen uptake quantity and pulse according to sex are determined, and the pulse rate is multiplied by the upper and lower limit value coefficients, to determine the upper limit value UL and the lower limit value LL for the pulse rate.

15 Claims, 47 Drawing Sheets

FIG. 14
| VO$_{2max}$ | 36 | 37 | 38 | 39 | 40 | 41 | 42 |
|---|---|---|---|---|---|---|---|
| PULSE RATE | 105 | 110 | 115 | 120 | 125 | 130 | 135 |
FIG. 15A
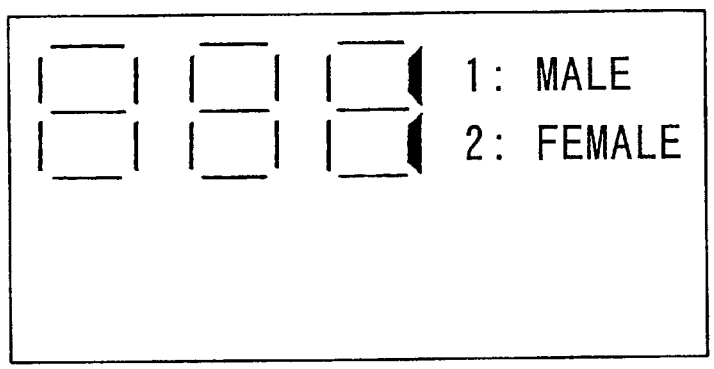
FIG. 15B
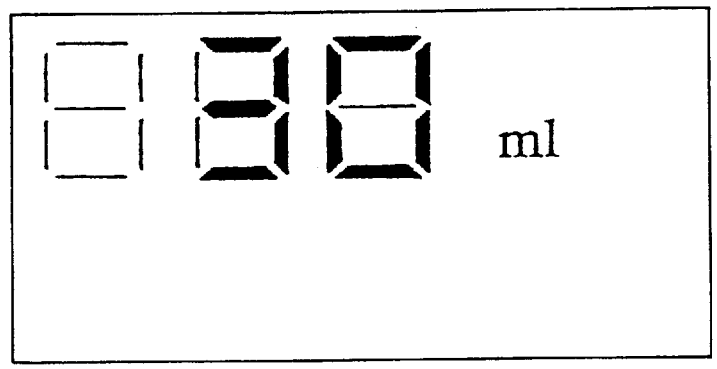

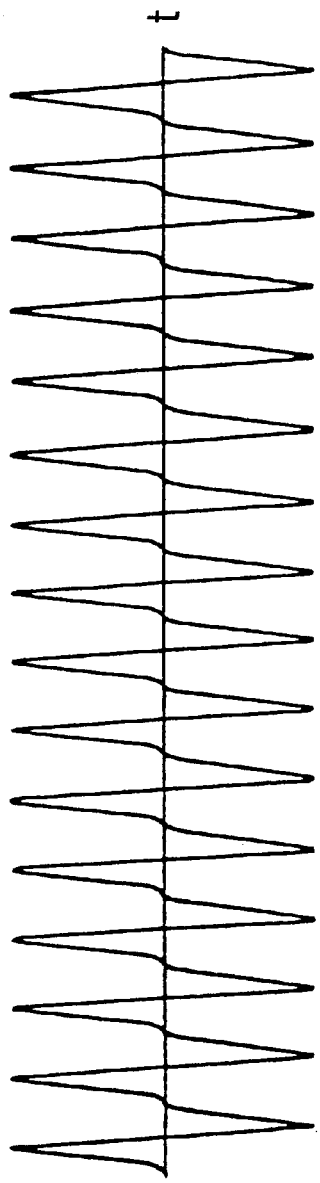
FIG. 21A ORIGINAL WAVEFORM
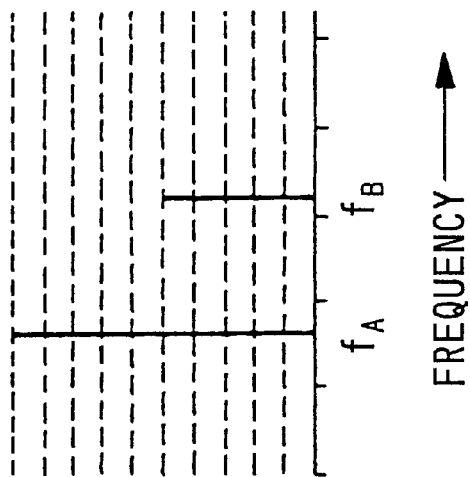
FIG. 21B

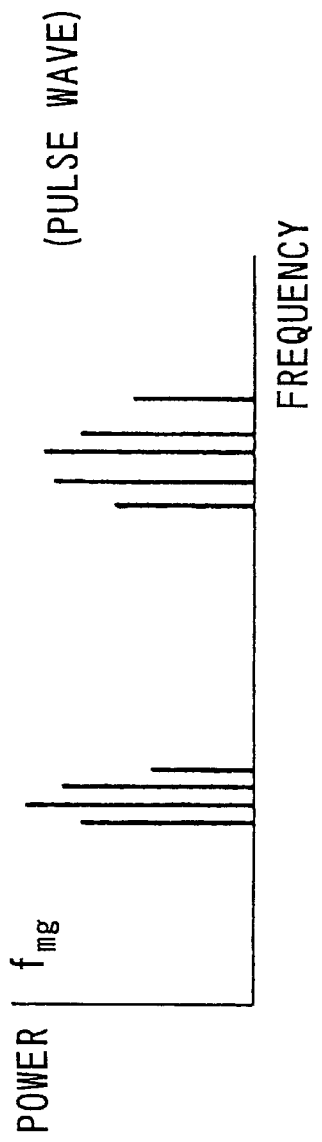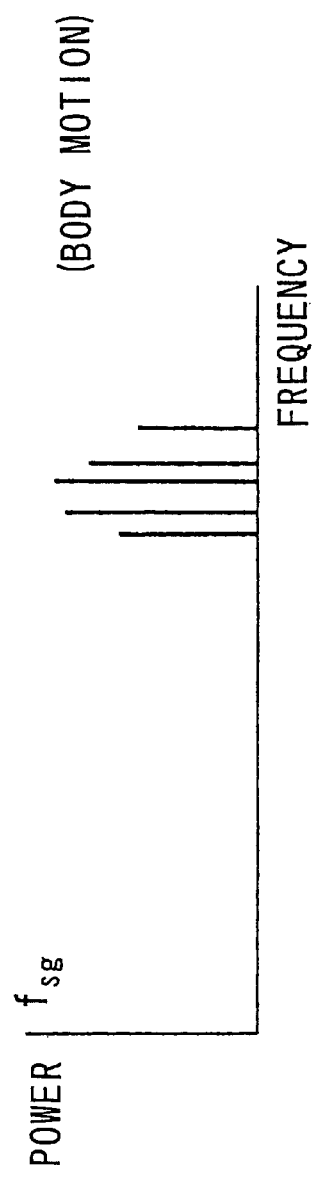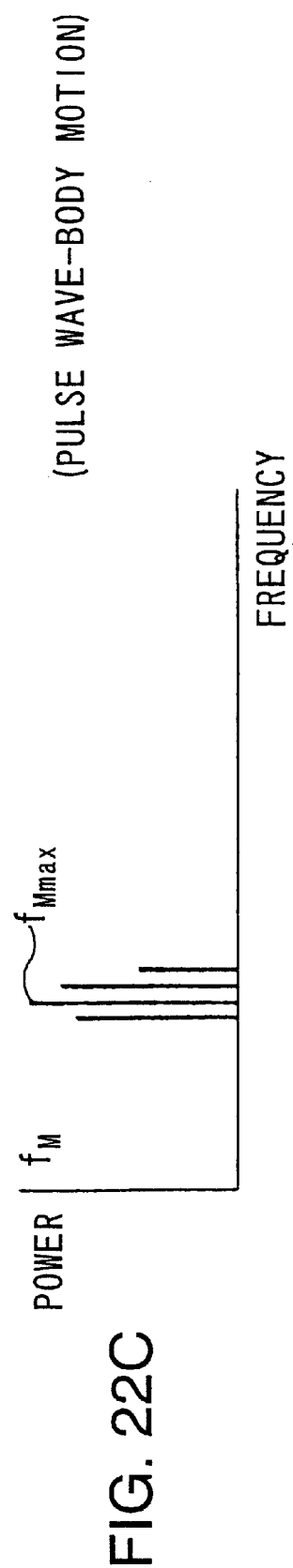

FIG. 35
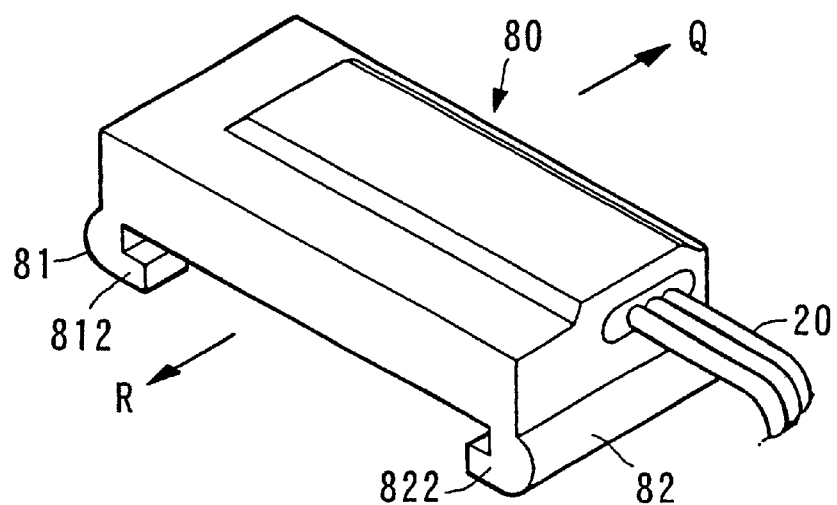
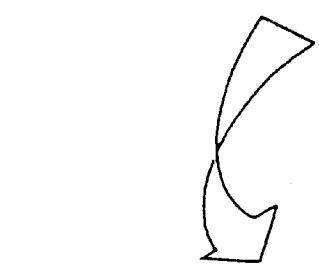
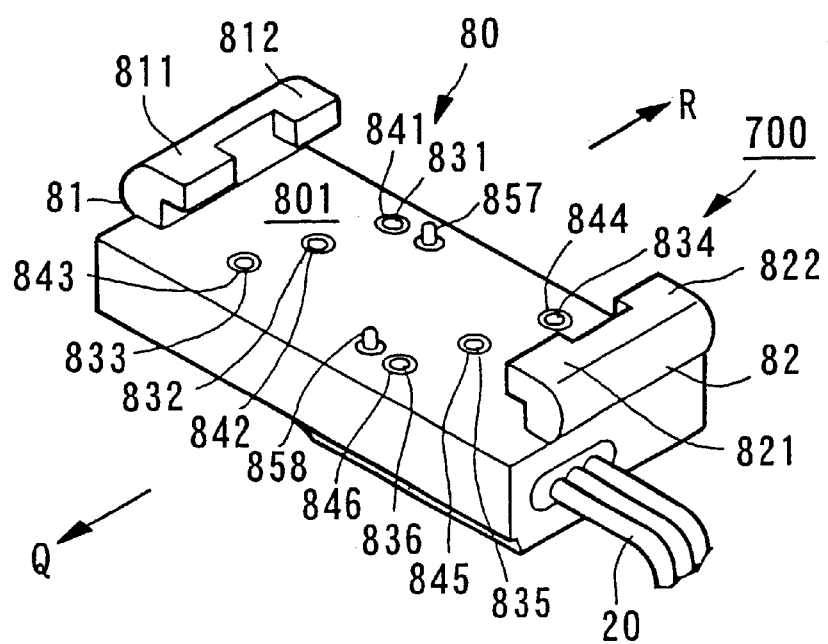

FIG. 38
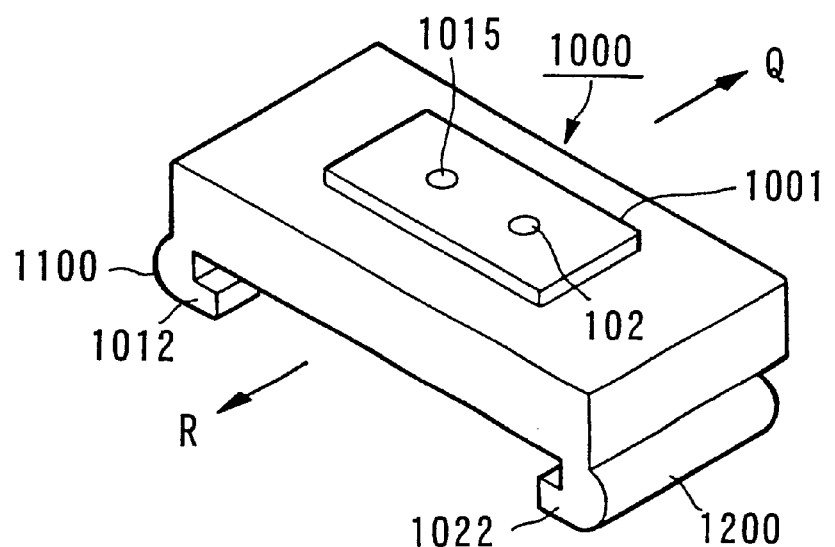
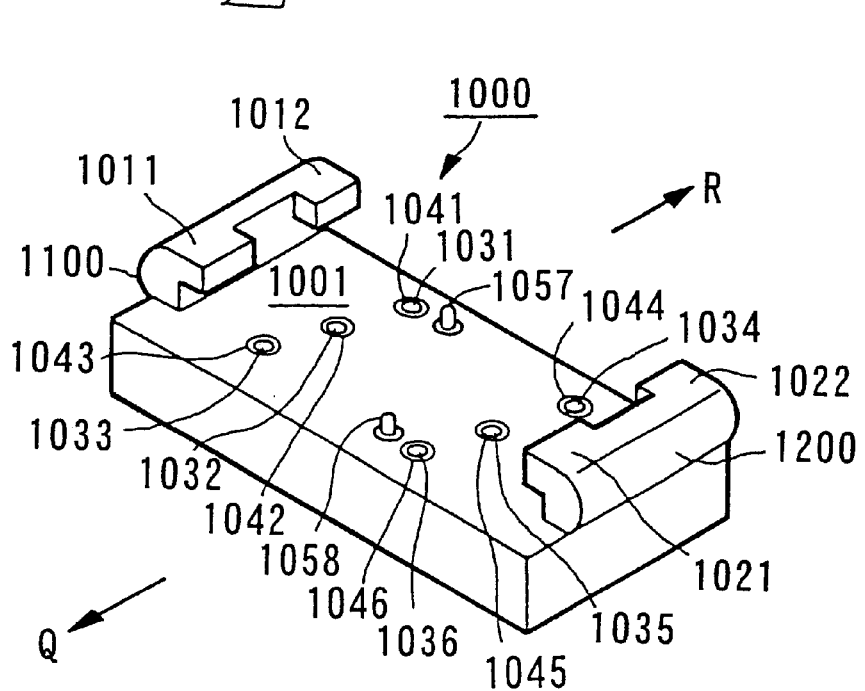

FIG. 41
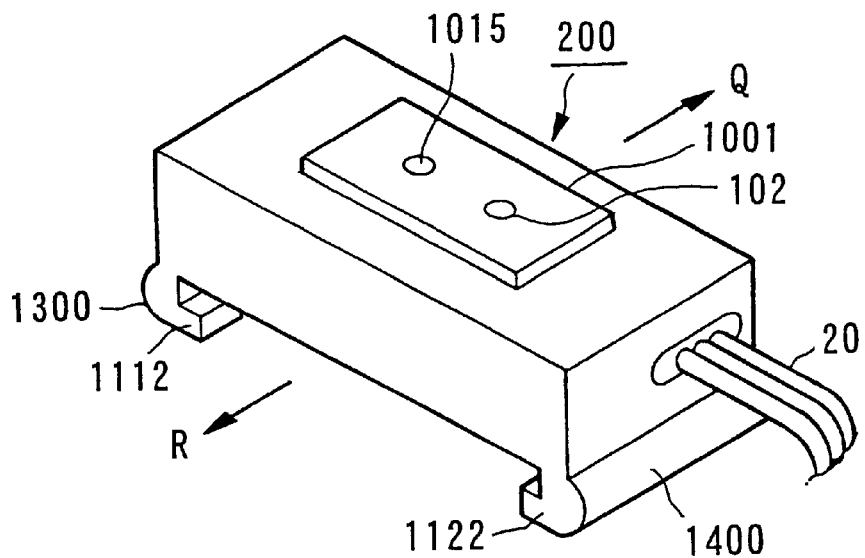
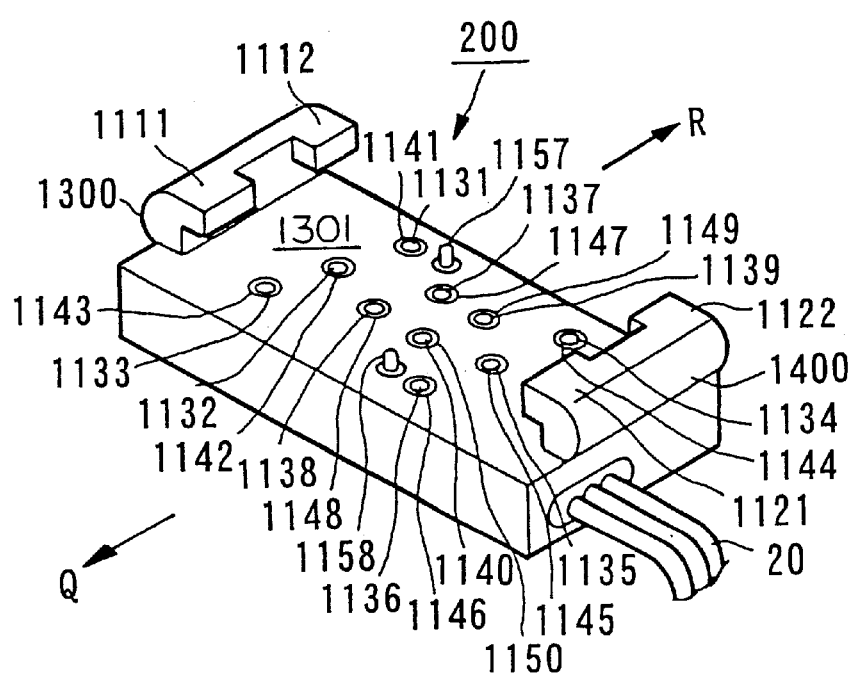

EXERCISE WORKOUT SUPPORT DEVICE

BACKGROUND OF THE INVENTION

1. Field of the Invention

The present invention relates to an exercise workout support device suitably employed to prescribe appropriate exercise to the user.

In particular, the present invention is suitable for use in a maximum oxygen uptake quantity estimating device, which enables the user to determine his own maximum oxygen uptake quantity easily; an exercise workout support device which shows the upper and lower limit values for a pulse rate corresponding to an appropriate exercise intensity; a portable pulse wave measuring device, which is provided to a portable device and measures pulse rate or other pulse wave information; or in the technique of sending information between a portable pulse wave measuring device and a data processing device, which processes the measurement data from the aforementioned portable pulse wave measuring device.

2. Description of the Related Art

In recent years, many people have been exercising for the improvement of their health.

When exercising, however, it is necessary to carry out exercise of a suitable intensity, since exercise below a given intensity level is not efficacious, while exercise above a given intensity level is dangerous. However, it has been difficult to know whether or not the intensity of exercise was appropriate until now.

This is because it is difficult to obtain data for determining suitable exercise intensity, and because it is difficult to promptly and accurately transmit the obtained data. The various factors involved will now be explained in detail.

(1) Data acquisition

Exercise intensity may be obtained by a conventionally known method employing the maximum oxygen uptake quantity, for example.

In general, maximum oxygen uptake quantity ($VO_{2max}$) refers to the maximum amount of oxygen taken up by a person (or, more broadly, by a living body) per unit time. Specifically, body size may be taken into account, such that the value of $VO_{2max}$ divided by the individual s body weight ($VO_{2max}$/wt) is an absolute index showing the endurance of that person. For this reason, the significance of the maximum oxygen uptake quantity is extremely high in sports physiology and the like. For example, by employing the maximum oxygen uptake quantity per unit body weight, it is possible to quantitatively evaluate the individual s endurance, making it easier to confirm the effects of training.

There are many conventionally known methods for determining maximum oxygen uptake quantity. However, all have in common the point that a test subject is required to perform exercise of a given intensity, with physiological parameters with respect to the exercise then measured.

These various methods may be broadly divided into two types: a direct method, in which the maximum oxygen uptake quantity is directly determined by measuring the test subject s expiration; and an indirect method, in which physiological parameters which have a high correlation to the maximum oxygen uptake quantity are measured and the maximum oxygen uptake quantity is indirectly obtained from these parameters. In the case of indirect methods, a variety of methods are available, including those that measure cardiac load or lactic acid values which are highly correlated to maximum oxygen uptake quantity, or a method which employs an Astrand-Ryhming nomogram.

However, in the case of both direct and indirect methods, the conventional art requires the use of a device such as a treadmill or bicycle ergometer in order to apply a given exercise load on the test subject. For this reason, there were physical limitations with respect to the number and location of such devices, as well as a necessity to restrict the test subject to the device itself. Accordingly, this was problematic as it applied a psychological stress on the test subject.

Moreover, in the case of direct methods, the device itself becomes very large since it directly measures the air gas expired by the test subject. Additionally, it is necessary to apply an exercise load up to the subject s all-out limit, so that the application of such methods was problematic in the case of individuals who are ill, not in good health or are middle aged or older.

On the other hand, from among the indirect methods, the method in which the lactic acid value is measured requires that blood be drawn, while the method in which the cardiac load is measured requires that systolic blood pressure be determined. Accordingly, these methods are troublesome.

(2) Data transmission

With respect to pulse wave measuring devices which are attached to the arm and can display various information, there are available devices which optically detect changes in blood quantity, and measure pulse rate and other pulse wave information based on these detected results. In these types of optical pulse wave measuring devices, a sensor unit provided with an light receiving element such as a photo transistor and a light emitting element like an LED (light emitting diode) is attached to the finger, for example. Light is then irradiated from the LED, with the light reflected by the blood vessels in the finger received at the photo transistor. The change in blood quantity is thereby detected as the change in the quantity of light received. Pulse rate and the like are then calculated based on this detected result, and are displayed. For this purpose, the device is designed so that a signal can be input or output between the device main body and the sensor unit by means of a connector on the main body of the device, and a connector consisting of a connector material which is formed to the tip of a cable which extends from the sensor unit.

Since the above-described pulse wave measuring device is attached to the arm, if a time measuring function is also provided to the device, it then becomes possible to measure lap or sprint times while also measuring the pulse wave during a marathon, for example. Accordingly, if this data is sequentially displayed on the display of the main body of the device at the end of the competition, reference data is obtained for determining the pace allocation for the next race.

However, in order to carry out a more detailed analysis of the information obtained during a marathon, it becomes necessary to send information stored in the main body of the device to a data processing device which is provided separately from the device main body. However, in the conventional art, a communications cable had to be attached between the device s main body and the data processing device so that this information could be relayed. Accordingly, this represented a troublesome procedure for the user.

SUMMARY OF THE INVENTION

The present invention was conceived in consideration of the above-described circumstances, and has as its first objective the provision of an exercise workout support device which can show the upper and lower limit values for the pulse rate corresponding to a suitable exercise intensity.

Further, the present invention has as its second objective the provision of a maximum oxygen uptake quantity estimating device which does not require the user to be restricted to the device, and which can determine the maximum oxygen uptake quantity easily and without troublesome operations.

Additionally, the present invention has as its third objective the provision of a portable pulse wave measuring device which enables wireless transmission and receipt of data such as pulse wave signals via optical communications with a data processing device which processes pulse wave information.

In view of the above-described first objective, the present invention is provided with:

an exercise intensity detecting means for detecting the test subject's exercise intensity;

a beat rate detecting means for detecting the test subject's beat rate;

a recording means for recording in advance the relationship between exercise intensity and beat rate, and the corresponding maximum oxygen uptake quantity; and a calculating means for obtaining the maximum oxygen uptake quantity corresponding to the detected beat rate and exercise intensity from the relationship stored in the recording means;

wherein the exercise intensity measuring means, beat rate detecting means, recording means and calculating means being incorporated into a portable device carried by the test subject.

As a result, it becomes possible to obtain maximum oxygen uptake quantity easily, without restricting the test subject to a large device or requiring troublesome operations to be performed.

In order to achieve the above-described second objective, the upper and lower limit values for the pulse rate corresponding to an appropriate exercise intensity are obtained from the $VO_{2max}$ determined in advance, and are displayed.

As a result, the upper and lower limits for the pulse rate corresponding to an appropriate exercise intensity can be displayed.

In order to achieve the above-described third objective, a portable pulse wave measuring device which is incorporated in a portable device, has a pulse wave detecting means for detecting the pulse wave in the body, and which sends and receives information including the pulse wave to and from a data processing device provided external to the portable device, has a communications means which uptakes the pulse wave and relays pulse wave data obtained from the pulse wave to an information processing device in a wireless manner by means of optical signals.

Accordingly, the pulse wave information obtained by the portable device is relayed by means of wireless communication using optical signals to a data processing device provided externally. Thus, it is not necessary to go through such procedures as connecting the portable device and the data processing device with a cable, but rather it is possible to relay data to the data processing device from the portable device when physically separated from the data processing device. Accordingly, this is very advantageous from the users perspective, as troublesome operations have been eliminated.

BRIEF DESCRIPTION OF THE DRAWINGS

FIG. 14 is an explanatory diagram showing an example of the pulse rate table in this same embodiment.

FIGS. 15A and 15B are is an explanatory diagrams showing an example of a display on display 8.

FIG. 21A is a diagram showing the signal obtained when frequency fA and frequency fB are summed.

FIG. 21B is a graph showing the result obtained after carrying out FFT processing on the summed signal.

FIG. 22A shows the result obtained after carrying out FFT processing of the signal output from pulse wave sensor 301.

FIG. 22B shows the result obtained after carrying out FFT processing of the signal output from body motion sensor 302.

FIG. 22C shows the pulse wave component obtained by subtracting the result shown in FIG. 22B from the result shown in 22A.

FIG. 35 shows the structure of connector piece 80 according to this embodiment.

FIG. 38 shows the structure of communications unit 100 according to this embodiment.

FIG. 41 shows the structure of communications unit 100 according to this embodiment.

PREFERRED EMBODIMENTS OF THE PRESENT INVENTION

1. Embodiment 1

The first preferred embodiment of the present invention will now be explained with reference to the accompanying figures.

1.1 Structure of the Embodiment

First, a maximum oxygen uptake quantity estimating device according to the first embodiment will be explained. The maximum oxygen uptake quantity estimating device according to this embodiment employs an Astrand-Ryhming nomogram (Astrand, P.O. and Ryhming, I.: A nomogram for calculation of aerobic capacity (physical fitness) from pulse rate during submaximal work. J. Appl. Physiol., 218~221, 1954.) to estimate the maximum oxygen uptake quantity ($VO_{2max}$(liter/min)) from the exercise intensity (operational intensity, work) and heartbeat rate at a given point in time as a test subject is performing a specified exercise. This estimated value is then divided by the test subject s body weight, to obtain a maximum oxygen uptake quantity ($VO_{2max}$/wt (unit: milliliter/kg/min)) per unit body weight.

1.1.1. Astrand-Ryhming nomogram

Figure 3:
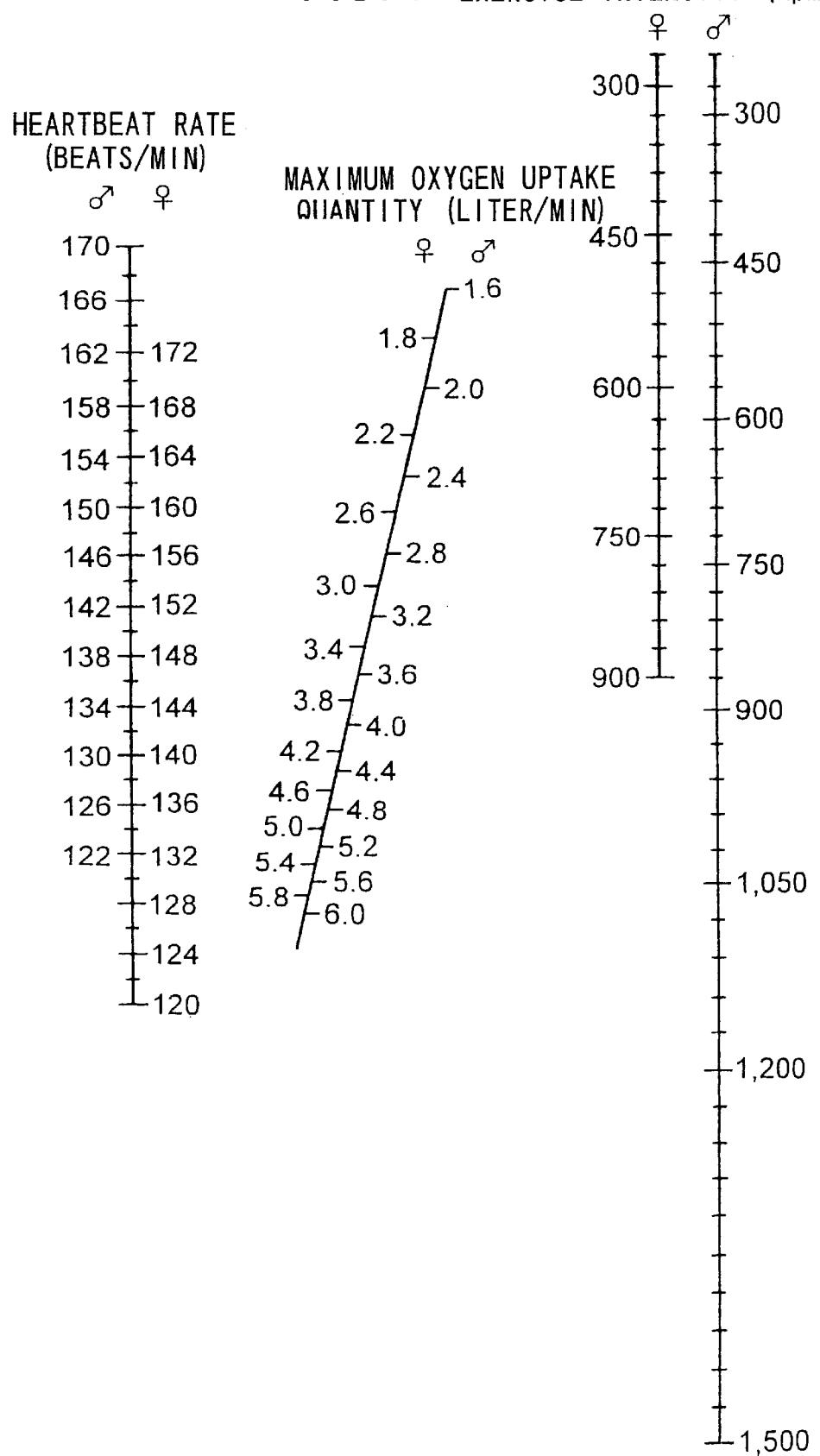
FIG. 3 is a diagram describing the Astrand-Ryhming nomogram employed in the present invention.

Before explaining the structure of this embodiment, a brief explanation of the aforementioned Astrand-Ryhming nomogram will first be made. FIG. 3 shows the details of a nomogram.

In this nomogram, the exercise intensity and heartbeat rate are plotted on the right and left axes respectively. Maximum oxygen uptake quantity ($VO_{2max}$) is indicated by the coordinates of the intersection of the middle line with a straight line drawn between the two axes. Parameters suitable for each of the two sexes are employed. In other words, by indicating the sex of the subject, the maximum oxygen uptake quantity ($VO_{2max}$) can be estimated from a function which employs exercise intensity and heartbeat rate as arguments.

1.1.1.1. Conditions for applying a nomogram

The conditions under which an Astrand-Ryhming nomogram may be employed will now be explained.

Figure 4:
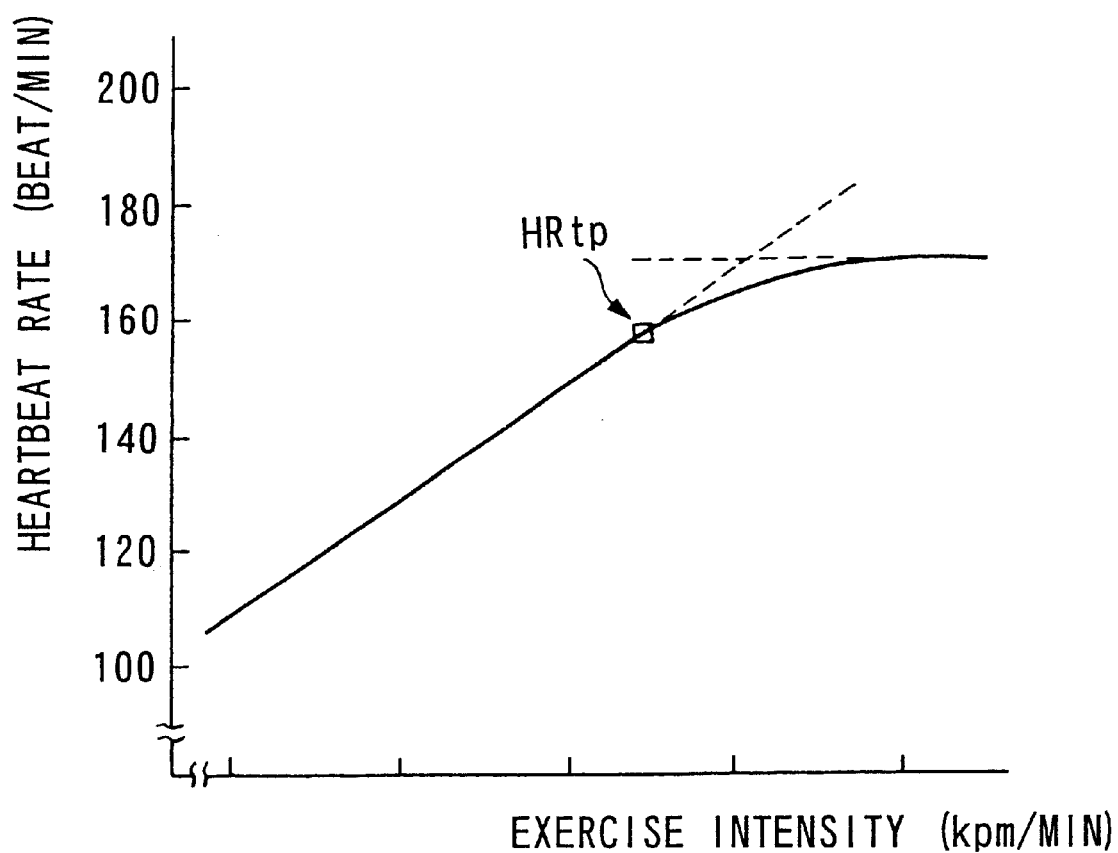
FIG. 4 is a diagram showing the relationship between exercise intensity and heartbeat rate.

In general, when exercise intensity is below a specific level, then the relationship between heartbeat rate and exercise intensity is such that heartbeat rate increases in proportion to the exercise intensity, as shown in FIG. 4. However, when the exercise intensity exceeds a given value, then the proportion of increase in the heartbeat rate with respect to the increase in exercise intensity slows, until finally saturation occurs. The point at which deviation from the proportional relationship between exercise intensity and heartbeat rate begins to occur is typically referred to as HRtp (Heart Rate turn point).

Although slightly higher than the anaerobic threshold (AT value), this HRtp is viewed to be roughly equivalent thereto.

The Astrand-Ryhming nomogram is formed by presupposing that there is a straight line relationship between the test subject s exercise intensity and heartbeat rate.

For this reason, in order to accurately estimate the maximum oxygen uptake quantity using the aforementioned nomogram, it is necessary to establish a straight line relationship between the test subject s exercise intensity and heartbeat rate. In order to judge whether or not a straight line relationship exists, it is necessary to measure exercise intensity at at least three or more stages, and determine the heart beat rate at each stage. Further, it is necessary that the test subject exercise until the HRtp appears.

1.1.2. Functional structure

Figure 1:
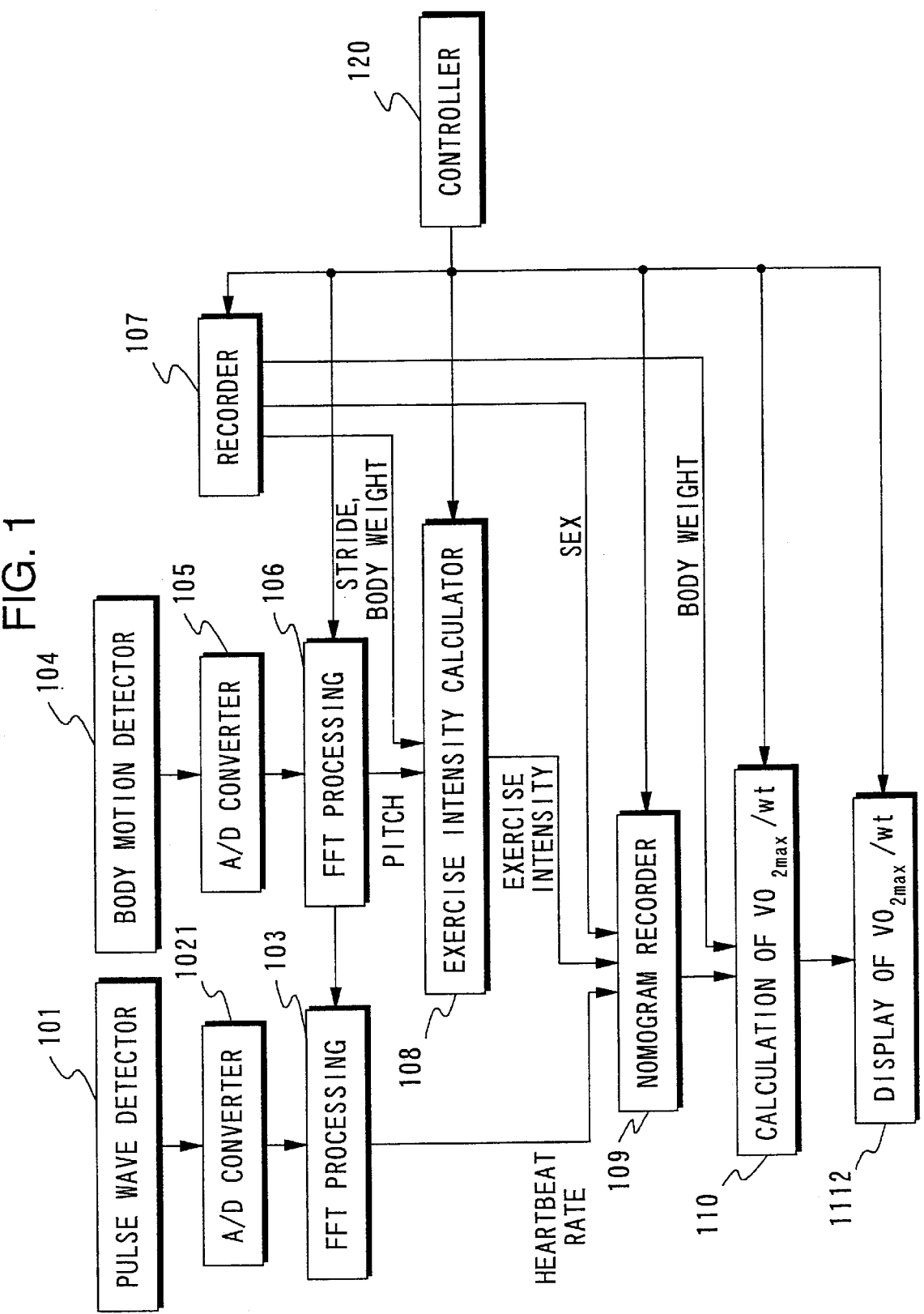
FIG. 1 is a block diagram showing the functional structure of the maximum oxygen uptake quantity estimating device according a first embodiment of the present invention.

The functional structure of the maximal oxygen uptake quantity estimating device according to this embodiment will now be explained. FIG. 1 is a block diagram showing the functional structure of the device.

In this figure, pulse wave detector 101 is a sensor which detects the test subject s pulse waveform. The pulse waveform signal from pulse wave detector 101 is converted to a digital signal by A/D converter 1021, and is subjected to FFT processing by FFT processor 103. The pulse rate is then determined from the results of this processing. Note that it is necessary to obtain the heartbeat rate for this embodiment. However, since the heartbeat rate equals the pulse rate, it is assumed that the obtained pulse rate is the heartbeat rate. Accordingly, with respect to pulse wave detector 101, it is acceptable to substitute a design wherein the heartbeat is directly detected.

Body motion detector 104 is a sensor for detecting body motion when the test subject is running. It may be formed of an acceleration sensor, for example. The body motion signal from this body motion detector 104 is converted to a digital signal by A/D converter 105, and is subjected to FFT processing by FFT processor 106 in the same manner as the pulse waveform. The pitch during running, i.e., the number of steps per unit time, is obtained from the results of this processing.

Recorder 107 records information relating to test subject s stride, sex and weight.

Exercise intensity calculator 108 calculates the exercise intensity from the obtained pitch, and the test subject s stride and body weight. In this example, the exercise carried out by the test subject is assumed to be running, so that exercise intensity may be indicated as the product of the distance run per unit time and the test subject s body weight. The distance run per unit time can be obtained by multiplying the test subject s stride and pitch.

Nomogram recorder 109 records the Astrand-Ryhming nomogram relationships described above. Accordingly; if these nomograms are employed, then maximum oxygen uptake quantity ($VO_{2max}$) can be obtained from the heartbeat rate, exercise intensity, and the test subject s sex.

$VO_{2max}$/wt calculator 110 calculates the maximum oxygen uptake quantity per unit weight ($VO_{2max}$/wt) by dividing the obtained maximum oxygen uptake quantity ($VO_{2max}$) by the test subject s body weight.

$VO_{2max}$/wt display 1112 displays the value obtained for maximum oxygen uptake quantity per unit weight ($VO_{2max}$/wt) to the test subject.

Controller 120 controls the various operations in this case.

1.1.3. Electrical structure

Figure 2:
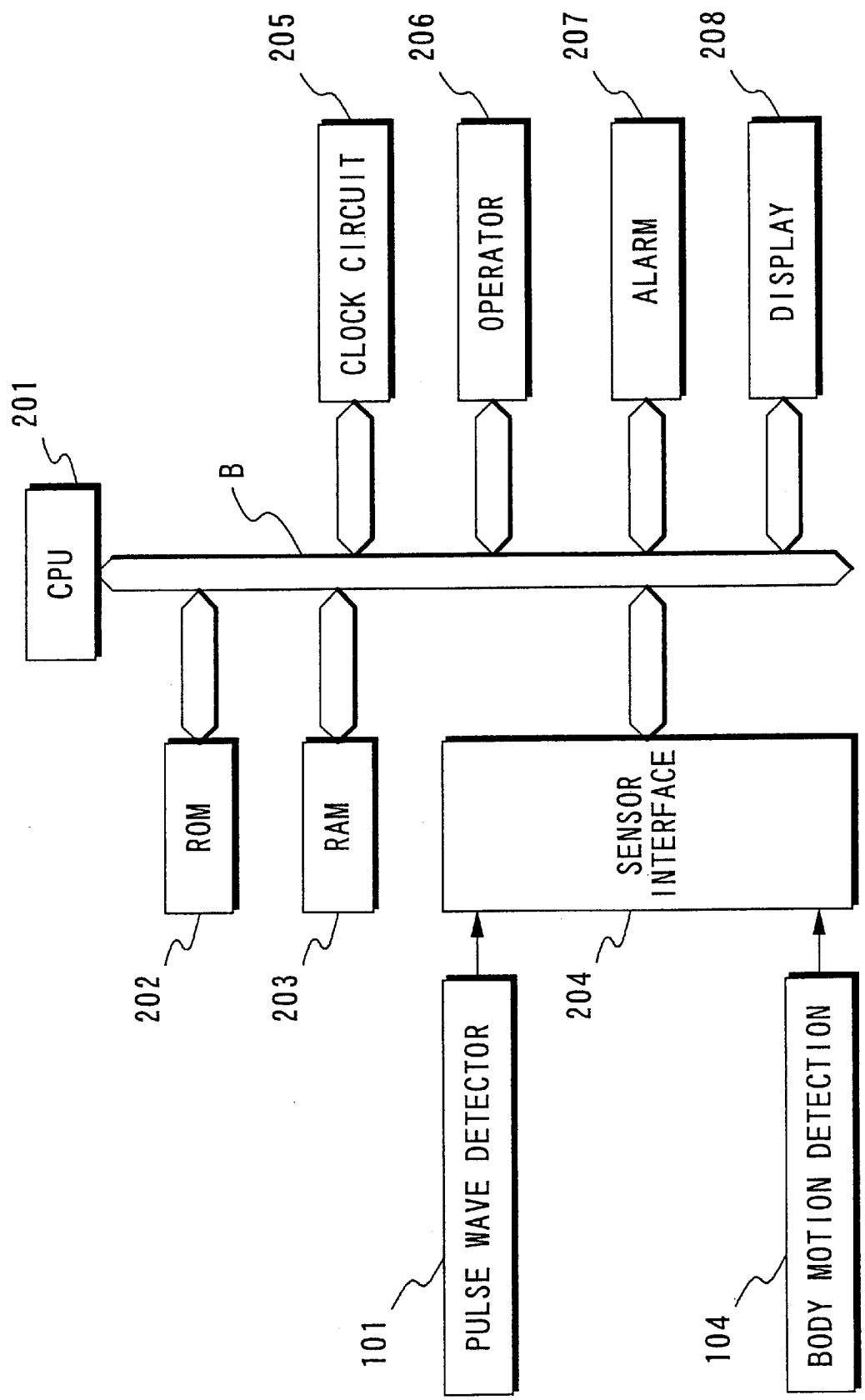
FIG. 2 is a block diagram showing the electrical structure of the maximum oxygen uptake quantity estimating device according to this same embodiment.

Next, the electrical structure for realizing the functional structure shown in FIG. 1 will be explained. FIG. 2 is a block diagram showing this structure.

In this figure, CPU 201 carries out control of various parts via bus B, as well as executing various processing and calculations. The FFT processors 103,106 shown in FIG. 1 correspond to exercise intensity calculator 108, $VO_{2max}$/wt calculator 110, and controller 120.

ROM 202 stores basic programs used by CPU 201, as well as the relationship expressed by the aforementioned Astrand-Ryhming nomogram, and corresponds to nomogram recorder 109 shown in FIG. 1.

With respect to the arrangement for storing the nomograms in ROM 202, the nomogram relationships shown in FIG. 3 may be rendered into a table and stored. If the significant digit for the heartbeat rate and exercise intensity is carried out to the third place, then a 50 step interval from 120 to 170 (beats/min) is provided for pulse rate and a 120 step interval from 300 to 1500 (kpm/min) is provided for exercise intensity. Therefore, if these are combined, 6,000 manners result. Accordingly, 12,000 manners result when the data for the different sexes is combined. In other words, the maximum oxygen uptake quantity ($VO_{2max}$) corresponding to the exercise intensity and the heartbeat rate can be obtained by means of the structure in which the values of the maximum oxygen uptake quantity ($VO_{2max}$) corresponding to each of the aforementioned combinations are stored in ROM 202, and the values corresponding to the measured heartbeat rate and exercise intensity are read out by CPU 201. The capacity required for the table is 12,000 manners, or slightly less than 12 kilo- bytes.

The unit of exercise intensity shown on the right axis is kpm/min, so that CPU 201 converts the obtained exercise intensity into kilo-pound-meters, and then applies the nomogram. Note that 1.00 [kpm/min]=0.1653 [W].

It is also acceptable to provide a design in which ROM 202 records the functions themselves as indicated by the nomogram, rather than employing a table, while CPU 201 carries out calculations using these functions.

RAM 203 temporarily stores various data employed in control by CPU 201, such as the test subject s body weight, stride, and sex. RAM 203 corresponds to recorder 107 shown in FIG. 1.

Sensor interface 204 carries out sampling of each analog output signal from pulse wave detector 101 and body motion detector 104 at respective specified time periods, and then converts the analog signal to a digital signal and outputs it. Sensor interface 204 corresponds to A/D converters 1021, 105 in FIG. 1.

In addition to the normal functions of a watch, clock circuit 205 is provided with a function for sending an interrupt signal to CPU 201 at specific time intervals determined in advance.

Operator 206 is provided so that the test subject input various values and set various functional modes. It consists of various button switches which will be described later.

Alarm 207 generates an alarm under the control of CPU 201, and notifies the test subject of various changes in state. From this respect then, the alarm is not specifically limited to one which relies on the aural sense. Rather, the alarm may take on any form recognized by the test subject s five senses, such as, for example, a vibration which relies on tactile perception.

Display 208 displays various information from CPU 201, and is composed, for example, of an LCD (liquid crystal display). Display 208 corresponds to the $VO_{2max}$/wt display 1112 shown in FIG. 1.

1.1.4. External structure

Figure 5:
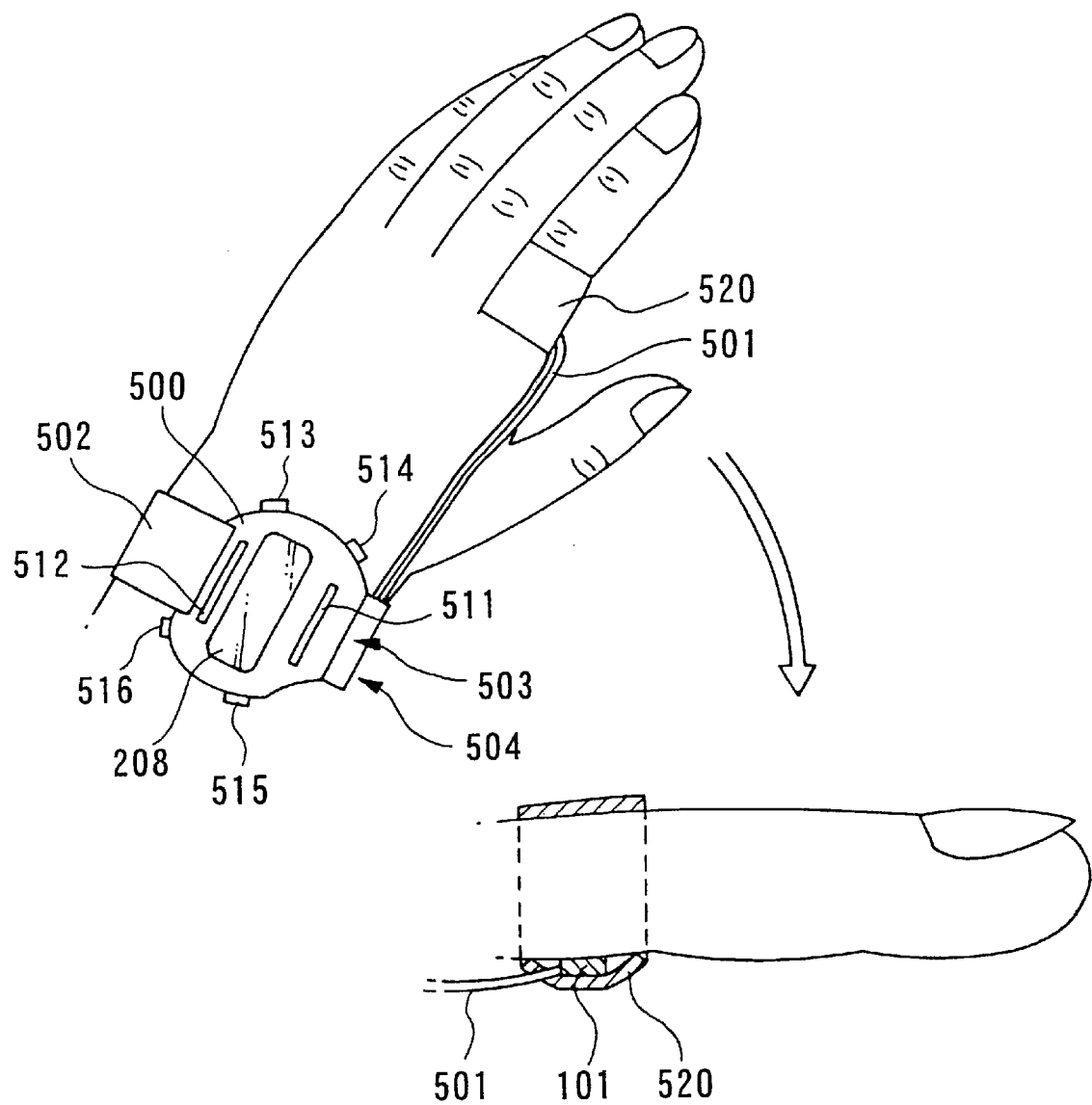
FIG. 5 shows the external structure of the maximum oxygen uptake quantity estimating device according to this same embodiment.

The maximum oxygen uptake estimating device according to the present embodiment is typically incorporated in an object which can be carried around by the test subject. One example of this design is the arrangement shown in FIG. 5, in which the device is incorporated in a wrist watch.

As shown in this figure, the maximum oxygen uptake quantity estimating device according to the present embodiment is composed of a device main body 500 having the structure of a wristwatch, a cable 501 connected to device main body 500, and a pulse wave detector 101 provided to the tip of cable 501.

A wrist band 502 is attached to device main body 500. More specifically, one end of wrist band 502 is wrapped around the wrist of the user from the 12 o'clock position, with the other end fixed at the 6 o'clock position of device main body 500.

A connector 503 is provided to the surface of device main body 500 at the 6 o'clock position. Connector piece 504, which is provided to an end of cable 501, is attached to connector 503 so as to be freely detachable. By releasing connector piece 504 from connector 503, the device may be used as a regular wristwatch or stopwatch.

A display 208 is provided to the surface of device main body 500. In addition to displaying the current time and date, display 208 employs a dot matrix or segment display to display various information such as the estimated maximum oxygen uptake quantity ($VO_{2max}$/wt), modes, etc.

Button switch 511 is disposed to below display 208 on the surface of device main body 500. It is employed for turning back the setting value by one when correcting the stride, body weight, time or date values.

In addition, button switch 512 is disposed above display 208, for advancing the setting values by one when correcting stride, body weight, time or date values. It is also employed by the test subject to start or stop measurement of elapsed time, for setting the sex of the test subject, and the like.

Button switches 513~516 are provided to the outer periphery and surface of device main body 500, at the 2, 4, 8, and 10 o'clock positions. The functions of each of these buttons are as follows.

Button switch 513 is provided for setting the various modes of the device, for example, the time display mode, the time measurement mode, the maximum oxygen uptake quantity estimating mode, the input and update mode, and the like. Button switch 514 is for setting which value from among the values for time (hour-minute-seconds), date (year-month-day), 12/24 hour clock display, body weight, stride, and sex, is being input/updated when the device is in the input and update mode. Button switch 515 is for switching the contents of the display on display 208. Finally, button switch 516 is for directing illumination of a back light in display 208. When button switch 516 is pressed, an electroluminescence (EL) back light on display 208 is turned on for 3 sec, for example, after which it automatically turns off.

Pulse wave detector 101 is composed of a blue light LED and light receiving element (neither are shown in the figures), and is blocked from receiving light by band 520 for fixing the sensor in place. Pulse wave detector 101 is attached between the base and the second joint of the test subject s index finger. Pulse wave detector 101 irradiates light from a blue light LED, and receives the light that is reflected by the hemoglobin in the capillaries at a light receiving element. The output waveform according to this received light is output to device main body 500 via cable 501 as the pulse waveform.

Note that elements not visible in the outer appearance of the device, for example, CPU 201, body motion detector 104, sensor interface 204 and the like, are housed in device main body 500.

1.2. Operation of the embodiment

The operation of the maximum oxygen uptake quantity estimating device according to the present embodiment will now be explained. As explained above, this device is provided with a variety of mode, one of which is a maximum oxygen uptake quantity estimating mode which estimates the maximum quantity of oxygen taken up. The operation of this mode will be explained below, while an explanation of the other modes will be omitted as they do not directly relate to this application.

1.2.1 Prerequisite for estimating maximum oxygen uptake quantity

Figure 6:
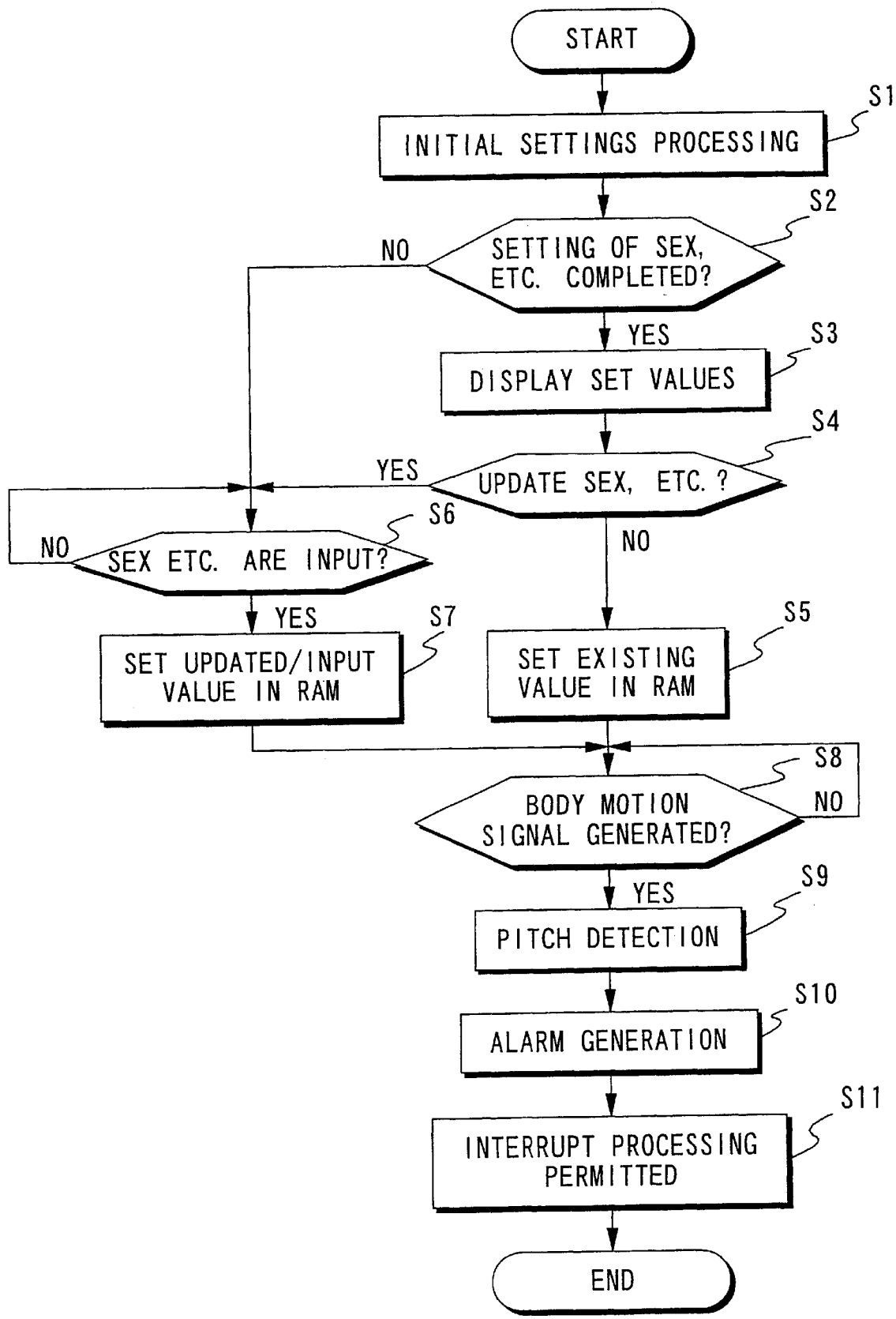
FIG. 6 is a flow chart showing the main operations in this same embodiment.

When the test subject operates button switch 513 to place the operational mode of device main body 500 in the mode for estimating maximum oxygen uptake quantity, CPU 201 first executes the program shown in FIG. 6. This main program sets the information employed as the prerequisite when estimating maximum oxygen uptake quantity ($VO_{2max}$/wt). Specifically, CPU 201 carries out the following steps S1~S11.

First, in step S1, CPU 201 executes initial setting processing such as securing the necessary area in RAM 203, clearing the aforementioned area, and the like.

Next, in step S2, CPU 201 determines whether or not information concerning the test subject s sex, body weight, and stride are set in RAM 203. When the maximum oxygen uptake quantity is estimated for the first time in this embodiment, the aforementioned information is not set in RAM 203, so that the determination in step S2 is carried out.

When the aforementioned information is set in RAM 203, however, then CPU 201 reads out the aforementioned set values from RAM 203 in step S3, and displays them on display 208. Next, in step S4, a message prompting the test subject to select whether or not to update these values is displayed.

When the test subject indicates that he does not want to update these values, then, in step S5, CPU 201 resets the aforementioned information as a predetermined value in RAM 203.

On the other hand, when the aforementioned information is not set in RAM 203, or when the test subject indicates that he does wish to update the information, then, in step S6, CPU 201 determines whether on not the aforementioned information has been input. If the information has been input, then processing returns to step S6. In other words, the processing order stands by in step S6 until the test subject s sex, body weight, and stride are input. Further, once this information is input/updated, then, in step S7, CPU 201 sets these values in RAM 203.

With respect to the directive for updating sex, etc., an approach may be considered, for example, in which the operational mode of device main body 500 is set to the input/update mode when the test subject operates button switch 513. Further, as a means of indicating that the value is not to be updated, an approach may be considered in which the test subject does not operate button switch 513 for a specified period of time. Methods for updating/inputting sex, body weight, stride and other information include a method in which the test subject sets the device in the input/update mode, uses button switch 514 to set the update/input target to sex, body weight, stride, etc., and then advances or reduces by one the targeted value using button switches 511 and 512.

When information related to the test subject s sex, body weight, and stride are set in RAM 203, then, in step S8, CPU 201 detects the body motion signal from body motion detector 104, and determines whether or not the test subject has actually started to run. If the test subject has not started to run, then processing again returns to step S8. In other words, the processing order stands by in step S8 until the test subject begins running.

When the test subject actually begins to run, then, in step S9, CPU 201 detects the pitch of running using a method which will be explained below. Next, in step SIO, control is carried out with respect to alarm 207, which is to inform the test subject that initiation of running has been confirmed, so that alarm 207 generates an alarm sound corresponding to the detected pitch for 10 seconds, for example. As a result, an alarm sound synchronized to the exercise is generated when the test subject begins to run.

In step S11, CPU 201 authorizes execution of two interrupt processes (calculation display processing and exercise intensity increase notification processing) which are executed at respective fixed intervals of time. In other words, when information such as the sex of the user is set in RAM 203, and the test subject actually begins to run, then CPU 201 is designed to carry out calculation display processing and exercise intensity increase notifying processing in parallel at respective fixed time intervals.

1.2.2. Pitch detection

The principle of the pitch detection operation during running which is executed in step S9 will now be explained briefly.

When the test subject is running, then it may be considered that (1) an acceleration signal accompanying vertical motion, and (2) an acceleration signal accompanying the swinging motion of the arms are superimposed in the body motion signal at body motion detector 104.

When an attempt is made to detect the components of the acceleration signal separately, then, because the vertical acceleration is expressed equally when taking a step with the right foot and when taking a step with the left foot, one period of the acceleration signal accompanying the vertical motion is viewed to be equivalent to one step during running.

On the other hand, the movement of the left arm to which device main body 500 is attached is pendulum motion in which the left hand is drawn back from a forward position when the left foot is placed forward, and is brought up from a rear position when the right foot is placed forward. Accordingly, the acceleration signal accompanying the arm swing is synchronized with the acceleration signal accompanying the vertical motion. Further, one period of this motion is equivalent to two steps during running.

For this reason, the first order harmonic wave component of the body motion signal in which the acceleration components from the vertical movement and the arm swinging movement are superimposed is dependent on vertical motion, while the second order harmonic wave component is dependent on the arm swinging motion.

However, it is typically the case in running that the acceleration accompanying the arm swinging motion is greater than the acceleration accompanying the vertical movement. Thus, the second order harmonic wave from the arm swinging motion is characteristically expressed in the body motion signal. Accordingly, the pitch of the running can, for example, be detected as a result of the following processing carried out by CPU 201 on the body motion signal from body motion detector 104.

Namely, first, CPU 201 carries out FFT processing of the body motion signal from body motion detector 104. Second, the harmonic wave component having the largest pitch is defined as the second order harmonic wave component, and the peak frequency thereof is detected. Third, the aforementioned peak frequency is determined, and multiplied by ½, to obtain the pitch.

1.2.3. Calculation display processing

Figure 7:
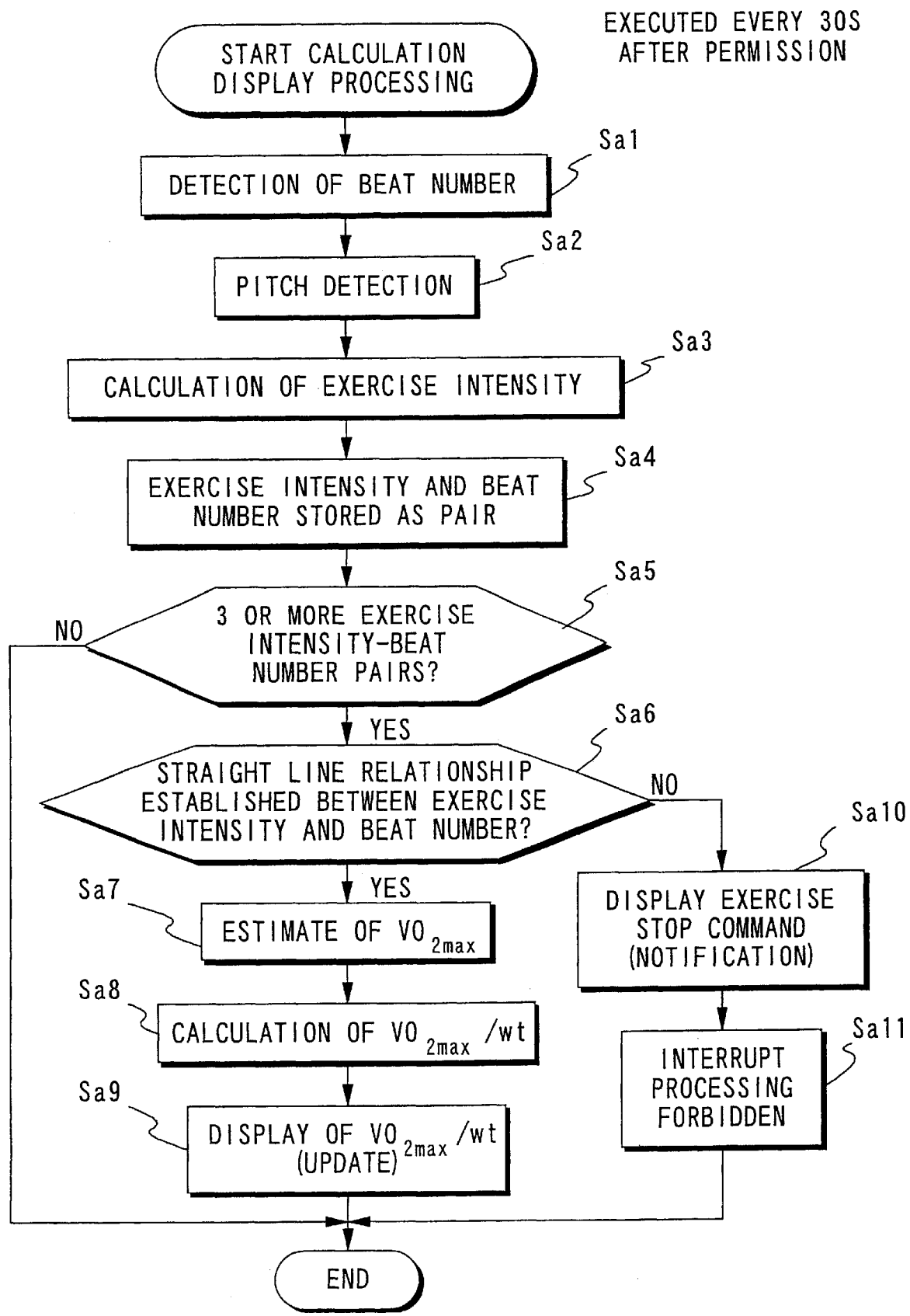
FIG. 7 is a flow chart showing the processing for calculation display in this same embodiment.

Next, the operation in calculation display processing, which is one type of interrupt processing, will be explained with reference to FIG. 7. In this calculation display processing, the maximum oxygen uptake quantity ($VO_{2max}$/wt) is estimated at fixed intervals of time from the test subject s exercise intensity and heartbeat rate during running, and displayed on the display.

CPU 201 detects the initiation of running by the test subject (step S8), and gives permission to execute interrupt processing (step S11). CPU 201 then executes the calculation display processing shown in FIG. 7 at specific time intervals (30 sec, for example).

First, at step Sa1, CPU 201 reads out the pulse waveform from pulse wave detector 101 via sensor interface 204, and determines the pulse rate, i.e., the beat rate (beats/min).

Next, in step Sa2, the body motion signal from body motion detector 104 is processed in the same way as in step S9, to detect the pitch of running.

In step Sa3, CPU 201 multiplies the test subject s stride which is stored in RAM 203 with the pitch detected on the immediately preceding step, to calculate the distance run by the test subject per unit time. This distance run is then multiplied by the user s body weight which is stored in RAM 203, to obtain exercise intensity [W]. This is then converted into [kpm/min].

Next, in step Sa4, CPU 201 stores the converted exercise intensity [kpm/min] and the detected beat rate [beat/min] as a pair in RAM 203.

In step Sa5, CPU 201 determines whether or not there are at least 3 exercise intensity-beat rate pairs stored in RAM 203. If there are less then 3 pairs, then it is not possible to determine whether or not a straight line relationship exists between exercise intensity and beat rate. Thus, the result of the determination is [NO], and the current calculation display processing is terminated. As will be described below, the test subject increases the intensity of exercise in stages during running in response to processing to notify the test subject to increase the intensity of exercise. Meanwhile, the calculation display processing is executed every 30 seconds, with the number of exercise intensity-beat rate pairs stored in RAM 203 increasing. Accordingly, once there are three or more exercise intensity-beat rate pairs, then the result of the determination becomes [YES].

When there are three or more exercise intensity-beat rate pairs, then at step Sa6, CPU 201 determines whether or not there is a straight line relationship between these. In this case, it is acceptable to consider that a slight error is included in the exercise intensity and beat rate. If a straight line relationship is established, then the aforementioned running is being carried out prior to the appearance of a Heart Rate turn point HRtp, and fulfills the conditions for applying an Astrand-Ryhming nomogram. Thus, CPU 201 executes the following steps Sa7~Sa9, to estimate maximum oxygen uptake quantity ($VO_{2max}$/wt).

In other words, in step Sa7, CPU 201 reads out from the table stored in ROM 202 the value corresponding to the sex of the test subject, which was recorded in RAM 203, of the maximum oxygen uptake quantity ($VO_{2max}$) corresponding to the beat rate and exercise intensity stored in step Sa4 during the current calculation display processing. In step Sa8, CPU 201 divides the read out maximum oxygen uptake quantity ($VO_{2max}$) is divided by the body weight of the test subject which is stored in RAM 203, and, in step Sa9, displays the value obtained from this division operation as the maximum oxygen uptake quantity ($VO_{2max}$/wt) per unit body weight on display 208.

Accordingly, once a straight line relationship between exercise intensity and beat rate has been established after the test subject has started running, then the maximum oxygen uptake quantity ($VO_{2max}$/wt) per unit body is displayed on display 208 each time the calculation display processing is executed.

On the other hand, if a straight line relationship is not established in step Sa6, then that indicates that the Heart Rate turn point HRtp has appeared during the running, or that the test subject has for some reason stopped running. Accordingly, in step Sa10, CPU 201 notifies the test subject to this effect by displaying a command to stop running (or a display indicating that the device has been released from the maximum oxygen uptake quantity estimating mode if there is no body motion signal being output). This notification may be accomplished by means of an alarm sound from alarm 207, or by means of both the display and the alarm sound.

In this way, the calculation display processing is executed every 30 seconds after the test subject has started running. Once a straight line relationship between exercise intensity and beat rate during running has been established, maximum oxygen uptake quantity ($VO_{2max}$/wt) is estimated from exercise intensity and heartbeat rate, and displayed on the display. On the other hand, if a straight line relationship has not been established, then the test subject is prompted to stop running. If there is insufficient data to determine whether or not a straight line relationship has been established, then the current exercise intensity and heartbeat rate are recorded, and the determination is put off until the next time.

Note that time interval for executing calculation display processing is not limited to 30 seconds.

1.2.4. Exercise intensity increase notifying means

Figure 8:
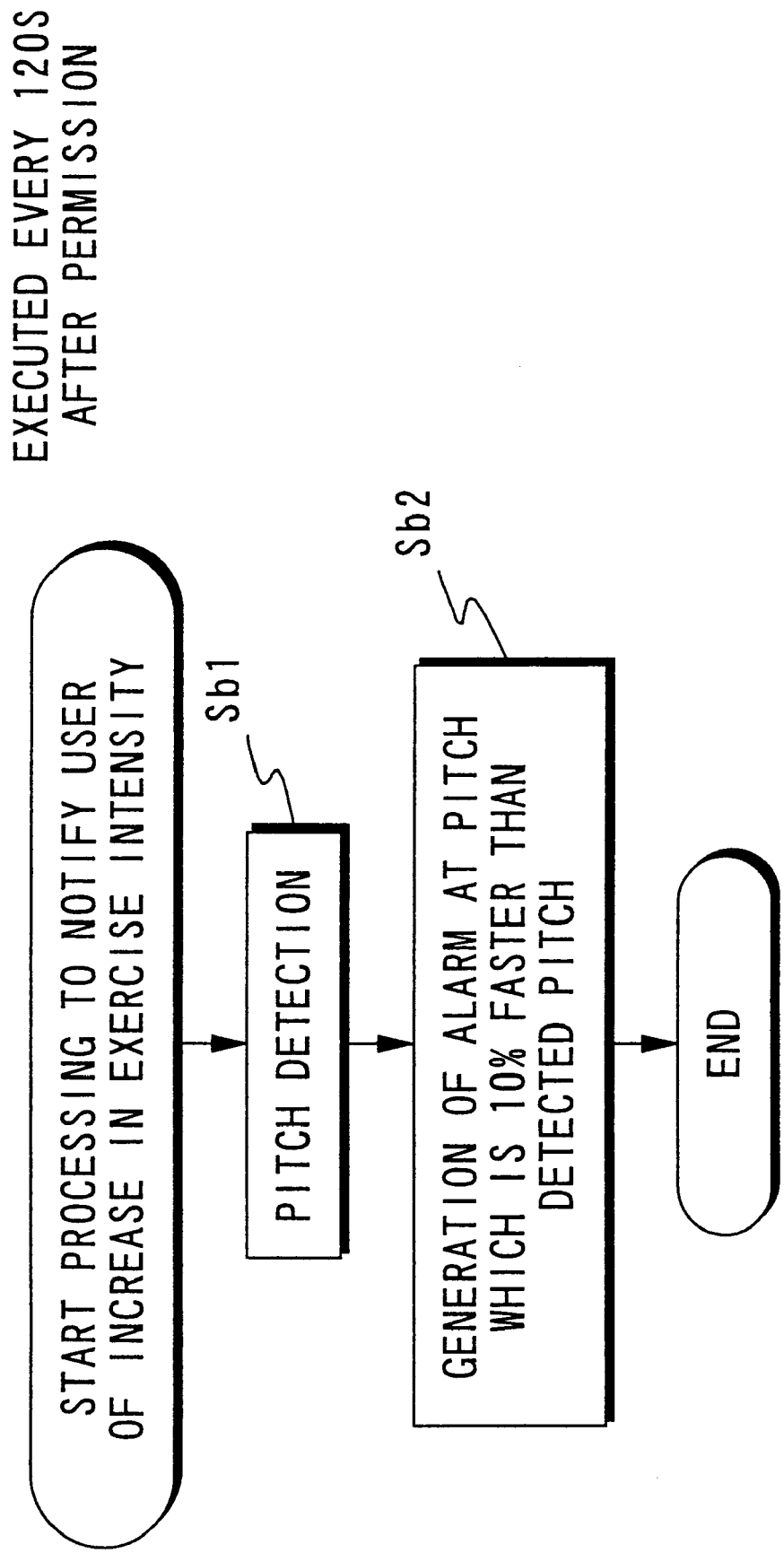
FIG. 8 is a flow chart showing the processing for notifying the user of an increase in exercise intensity in this same embodiment.

Next, FIG. 8 will be used to explain the other interrupt processing, exercise intensity increase notifying processing. In this exercise intensity increase notifying processing, an order to increase the exercise intensity during running is directed at the test subject at fixed time intervals (120 sec, for example) after the test subject has started running.

CPU 201 detects that the test subject has started running (step S8), and permits execution of interrupt processing (step S11). When this occurs, CPU 201 then executes the exercise intensity increase notifying processing shown in FIG. 8 at fixed time intervals (120 sec, for example).

First, at step Sb1, CPU 201 detects the pitch of the running by processing the body motion signal of body motion detector 104 in the same manner as in steps S9 and Sa2 described above.

Next, in step Sb2, CPU 201 determines the pitch at which there is a 10% increase over the pitch detected in the preceding step, and controls alarm 207 to generate a beep alarm in accordance with this pitch for 10 seconds, for example. As a result, the test subject is able to referentially know the timing when increasing exercise intensity in stages during running, as well as the pitch when running at the next stage.

In this way, the exercise intensity increase notifying processing is executed every 120 seconds after the test subject begins running, with the test subject being notified to increase exercise intensity by 10% each time.

With respect to exercise intensity during running, note that the exercise intensity is not obtained during exercise intensity increase notifying processing, but rather is obtained by measurements and calculations in steps Sa2 and Sa3 in the calculation display processing discussed above. Thus, it is not necessary that the test subject increase exercise intensity by 10% only. In other words, exercise intensity increase notification is merely a target. Thus, the test subject may maintain exercise intensity at a constant level, or conversely, may reduce exercise intensity to some extent. Moreover, it is also acceptable for the test subject to vary exercise intensity according to his own preferences.

In addition, from the perspective of a target, the interval for executing exercise intensity increase notifying processing is not limited to 12 seconds.

1.3. Specific operation

Next, the specific operation in embodiment of this type will be explained.

The test subject operates button switch 513 to place the device main body 500 in the mode for estimating the maximum oxygen uptake quantity. As a result, CPU 201 carries out the main program shown in FIG. 6. Information concerning the sex, body weight, and stride which currently set are displayed on display 208 (step S3). When the information displayed here differs from that of the test subject, then the test subject operates button switch 514 to select the target for update. Then, using button switches 511 and 512, the test subject sets the selected values so that they are appropriate for him. As a result, this value is set in RAM 203 as new information relating to the test subject (step S7). On the other hand, if the displayed information is that of the test subject, then the test subject does not operate the device for a specific period of time, such that this fact is communicated to device main body 500. As a result, the preceding information is reset in RAM 203 as information relating to the test subject (step S5). In this way, various information such as sex, etc., relating to the test subject is set in RAM 203. As a result, the next time that the device is set to the maximum oxygen uptake quantity estimating mode, the information is again read out and displayed, so that the test subject does not have to again enter information relating to himself each time the device is set to the maximum oxygen uptake quantity estimating mode.

Once information such as sex and the like relating to the test subject are set in RAM 203 and the test subject begins running, an alarm sound is generated corresponding to the pitch of running (step S10). Thus, the test subject may confirm that device main body 500 has detected the running and has initiated estimation processing.

When the test subject starts running, interrupt processing is permitted at device main body 500 (step S11). Thus, calculation display processing and exercise intensity increase notifying processing are executed every 30 seconds and 120 seconds, respectively.

After starting to run, the test subject carries out running at a constant pitch for 120 seconds, until the first exercise intensity increase notifying processing is initiated. During this 120 seconds, calculation display processing is executed 4 times. However, since the exercise intensity is constant, there is only one exercise intensity-beat rate pair obtained. Accordingly, during this time, the processing in steps Sa6~Sa9 in the calculation display processing are not carried out.

Next, once 120 seconds have elapsed since the test subject started running, the first exercise intensity increase notifying processing is executed. As a result, an alarm sound is generated at an interval which represents a 10% increase over the previous pitch. In accordance with the alarm sound, the test subject increases the pitch by 10%, and tries to maintain running at this pitch for 120 seconds, until the second exercise intensity increase notifying processing is executed. The calculation display processing is carried out 4 times during this 120 seconds. However, the number of obtained exercise intensity-beat rate pairs when combined with the pair obtained in the previous processing does not exceed 2. Accordingly, steps Sa6~Sa9 in calculation display processing are not carried out during this time interval.

When 120 seconds have elapsed since the first exercise intensity increase notifying processing was executed, the second exercise intensity increase notifying processing is executed. An alarm sound is generated at an interval corresponding to a further 10% increase in pitch. The test subject increases the pitch by 10%, and tries to maintain running at this pitch.

When calculation display processing is executed 30 seconds after this point in time, it is viewed that the change in the pulse rate due to the increase in pitch has already entered a steady state. For this reason, the obtained exercise intensity-beat rate pair, when combination with the pairs obtained previously, makes three pairs. Accordingly, if a straight line relationship can be established between these pairs, then steps Sa7~Sa9 in calculation display processing are executed, and the maximum oxygen uptake quantity ($VO_{2max}$/wt) per unit body weight of the test subject is displayed on display 208. As a result, the test subject is able to know his maximum oxygen uptake quantity per unit body weight ($VO_{2max}$/wt).

Each time the calculation display processing is executed every 30 seconds thereafter, the test subject s maximum oxygen uptake quantity per unit body weight ($VO_{2max}$/wt) is displayed on display 208. However, the displayed maximum oxygen uptake quantity ($VO_{2max}$/wt) should not have changed very much. Namely, while the maximum oxygen uptake quantity ($VO_{2max}$/wt) can be improved by training, it is essentially a value specific to each individual.

Since exercise intensity increase notifying processing is executed every 120 seconds, the alarm sound is generated at an interval corresponding to a 10% increase in pitch. The test subject raises the pitch by 10%, and tries to maintain running at this level. However, as a result of increasing the pitch in stages, the exercise intensity and heartbeat rate at that point in time may deviate from a straight line relationship with the exercise intensity and heartbeat rate obtained previously. When this happens, it signifies that a Heart Rate turn point HRtp has been exceeded. Accordingly, in this case, a command to stop running is displayed on display 208 as a result of calculation display processing executed at that point in time (step Sa10). Thereafter, execution of interrupt processing is not allowed (step S11), and operation of the maximum oxygen uptake quantity estimating mode is terminated. As a result, the operations in this embodiment come to an end.

As a result of the present embodiment, the test subject is able to know his own maximum oxygen uptake quantity simply by carrying out running according to his own preference, without being restricted by a large device. Accordingly, it is extremely easy for the test subject to have an objective evaluation of his physical capacity, and to confirm the effects of training.

In the preceding embodiment, pulse wave detector 101 is composed of a blue light LED and a light receiving element, and is designed to detect light reflected by hemoglobin in the capillaries as the pulse waveform. However, the present invention is not limited thereto. For example, it is acceptable to use a piezoelectric microphone to form pulse wave detector 101, for example. However, where employing a piezoelectric microphone, the vibration accompanying the pulse wave and the vibrational component accompanying body motion are simultaneously detected. As a result, it is necessary to carry out processing to subtract out the body motion signal from body motion detector 104 from the output signal component from the piezoelectric microphone, so that only the vibration component accompanying the pure pulse wave is obtained.

In the above-described embodiment, FFT processing was employed to obtain the pulse wave signal, or to obtain the heartbeat rate or pitch from the body motion signal. However, the present invention is not limited thereto. Rather, it is also acceptable to employ MEM analysis, wavelet analysis or the like. Further, simple peak detection may also be used.

In the preceding embodiment, the stride value was directly input into device main body 500. However, it is also acceptable to provide a design where the body height value is input instead. Stride is then indirectly obtained by multiplying the input value for body height by a fixed coefficient, or according to a function obtained by taking the input body height and body weight as arguments. This stride value is then set in RAM 203, and may be employed when obtaining exercise intensity.

2. Embodiment 2

An explanation will now be made of the second embodiment of the present invention.

Although there are slight differences between individuals, stride is generally viewed to become shorter when the pitch of running is increased. However, in the first embodiment, a constant value for stride was employed despite the fact that the pitch was increased, since the stride value set in RAM 203 was used without modification. Namely, the first embodiment does not take into consideration this characteristic of running.

Accordingly, from this perspective, the first embodiment has a flaw in that the exercise intensity obtained at step Sa3 tends to be inaccurate.

Thus, in the second embodiment, a table showing the relationship between pitch and the stride correction coefficient is obtained in advance and stored. When the pitch changes during running, then the stride correction coefficient corresponding to the changed pitch is read out, and multiplied by the stride set in RAM 203, so as to correct to a stride corresponding to the aforementioned pitch. Accordingly, the flaw encountered in the first embodiment is removed in the second embodiment.

Figure 9:
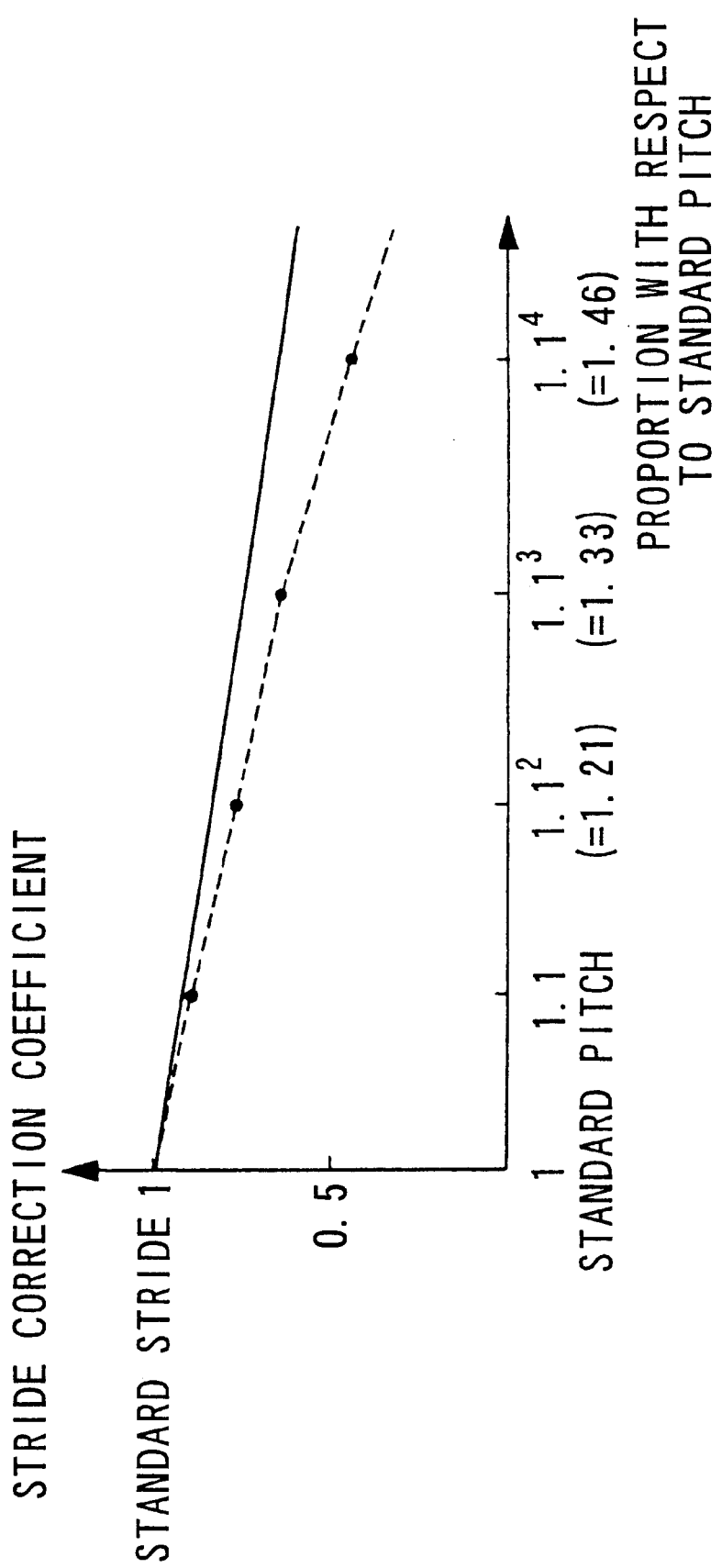
FIG. 9 is a diagram showing the relationship between the pitch and the stride correction coefficient in the maximum oxygen uptake quantity estimating device according to the second embodiment of the present invention.

Accordingly, the structure of the maximum oxygen uptake quantity estimating device according to the second embodiment does not include any essential components which must be added to the maximum oxygen uptake quantity estimating device according to the first embodiment which is shown in FIGS. 1 and 2. Rather, it is merely necessary to provide a table in RAM 203 showing the relationship between pitch and the stride correction coefficient. In this table, the stride correction coefficient becomes slightly less than 1 in accordance with the increase in pitch, as shown by the solid line in FIG. 9: Note that the standard pitch is the pitch at which the stride during running becomes equal to the input stride (standard stride).

The relationship between pitch and the stride correction coefficient is viewed to vary greatly for each test subject. Accordingly, it is necessary to edit the relationship shown by the solid line in FIG. 9 to match the individual characteristics of the test subject, so that it becomes that indicated by the dashed line in the same figure.

The details are as follows. First, the test subject measures stride with respect to the standard pitch after increasing the pitch in stages by 10%, for example, and determines what proportion the measured stride is with respect to the standard stride. Second, the test subject uses button switches 511~514 to input this proportion and the proportion with respect to the standard pitch into device main body 500.

When this is done, CPU 201 carries out the following operations. Namely, CPU 201 plots the input pitch proportion and stride proportion, and interpolates between these plots to obtain the characteristics such as shown by the dashed line in FIG. 9. This is then rendered into a table and stored in a specific area in RAM 203.

When the test subject is running, and exercise intensity is calculated in step Sa3, CPU 201 first determines what proportion the pitch detected in the preceding step Sa2 is with respect to the standard pitch, and second, reads out the stride correction coefficient corresponding to this proportion from the aforementioned table. Third, CPU 201 multiplies the standard stride read out from RAM 203 by the aforementioned coefficient, to correct the stride so as to match the pitch of the running. Fourth, CPU 201 employs the corrected stride in the calculation of exercise intensity.

Accordingly, in the second embodiment, stride is corrected even when the pitch is increased during running. Moreover, this correction matches characteristics specific to the individual test subject, allowing the maximum oxygen uptake quantity ($VO_{2max}$/wt) to be obtained more accurately.

3. Embodiment 3

The third embodiment of the present invention will now be explained.

When running, it is not necessary the case that the activity is limited to a flat path. Rather, on the typical road, there are generally some slopes. In the case where slopes are present during running, the stride becomes shorter when running up the slope, but becomes longer when running down the slope (in the case of marathon runners, however, this relationship is reversed).

For this reason, when running on a slope, the stride will vary even if the pitch is constant. Thus, the exercise intensity changes. However, in the first embodiment above, the value set in RAM 203 is employed for stride. Accordingly, if pitch is constant, then exercise intensity is calculated as a constant value even if slopes are present.

Accordingly, the first embodiment has a disadvantage in that the exercise intensity obtained in step Sa3 tends to be inaccurate.

Therefore, in this third embodiment, the slope during running is obtained, and the stride is corrected in response to this slope. As a result, the disadvantage encountered in the first embodiment is resolved here.

Figure 10:
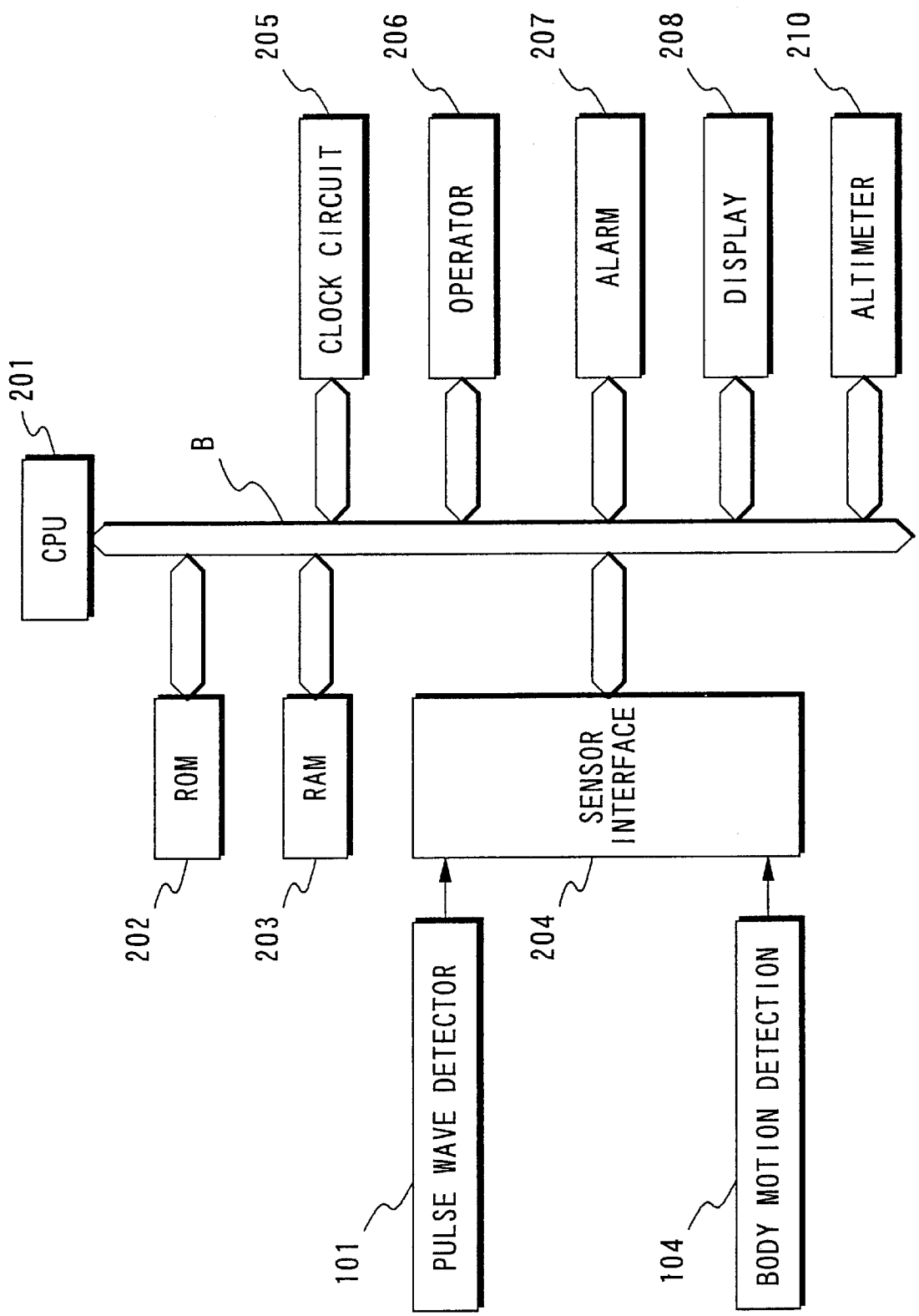
FIG. 10 is a block diagram showing the electrical structure of the maximum oxygen uptake quantity estimating device according to a third embodiment of the present invention.

FIG. 10 is a block diagram showing the electrical structure of the maximum oxygen uptake quantity estimating device according to the third embodiment. The structure shown in this figure differs from the structure of the first embodiment shown in FIG. 2 in the provision of an altimeter 210. This altimeter 210, which is housed inside device main body 500, obtains the difference in altitude based on the difference in air pressure.

If the processing to obtain the altitude difference is executed during the calculation display processing, then the processing interval is 30 seconds. Accordingly, the difference in altitude during running is obtained for this time interval.

Figure 11:
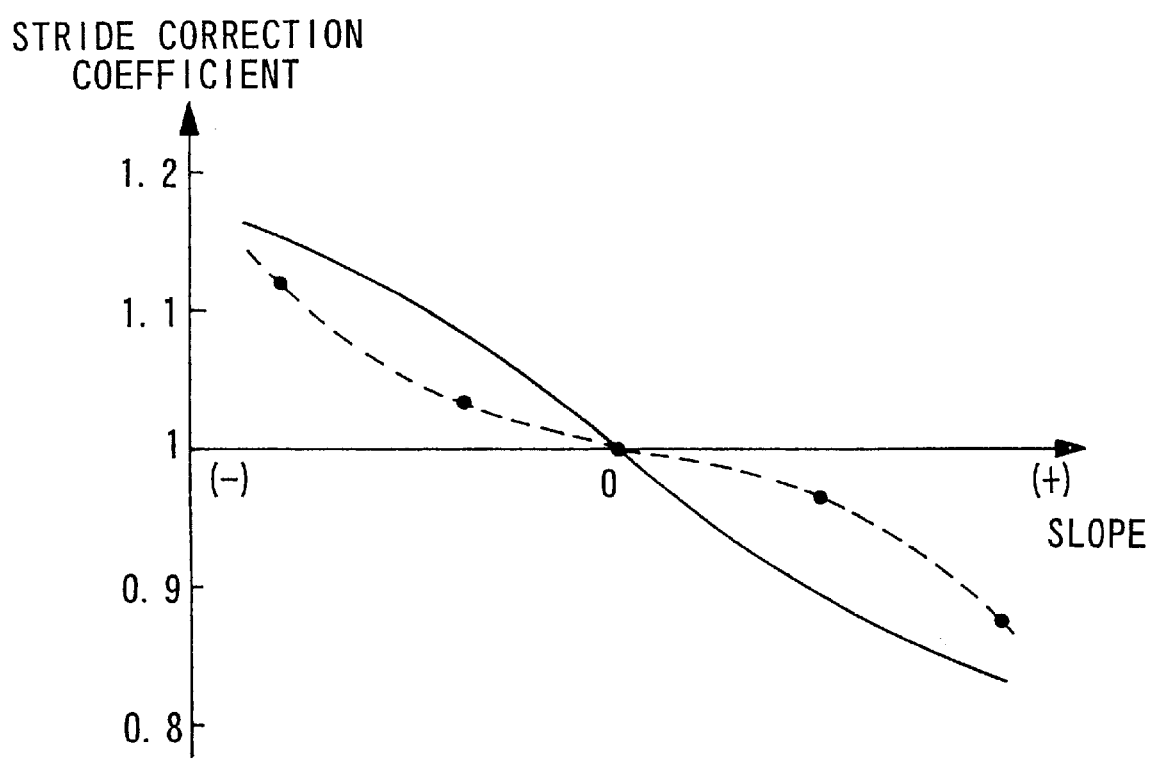
FIG. 11 is a diagram showing the relationship between the altitude difference and the stride correction coefficient in this same embodiment.

Additionally, RAM 203 in the third embodiment of the present invention is provided with a stride coefficient table having characteristics such as shown in FIG. 11.

As shown by the solid line in this table, when the slope is (+), i.e., where ascending a hill, the stride correction coefficient becomes gradually less than [1] as the slope becomes stronger. Conversely, when the slope is (−), i.e., where descending a hill, the stride correction coefficient becomes gradually greater than [1] as the slope becomes stronger.

As in the second embodiment, the relationship between the slope and the stride correction coefficient will vary greatly between individual test subjects. Thus, it is necessary to edit the relationship shown by the solid line in the figure to match the characteristics of the individual test subject, so that the relationship becomes as indicated by the dashed line in the figure.

The details of this process are as follows. First, the test subject runs on a path having a slope, and the proportion of the running stride with respect to the standard stride is determined together with the slope. It is preferable to have not one, but several slope-stride pairs. Second, the test subject uses button switches 511~514 to input the obtained slope and stride proportion into device main body 500.

As a result, CPU 201 carries out the following operations. Namely, CPU 201 plots the input slope and stride proportion, and interpolates between these plots to obtain the characteristics indicated by the dashed line in FIG. 11, for example. This is then rendered into a table and stored in a specific area in RAM 203.

Figure 12:
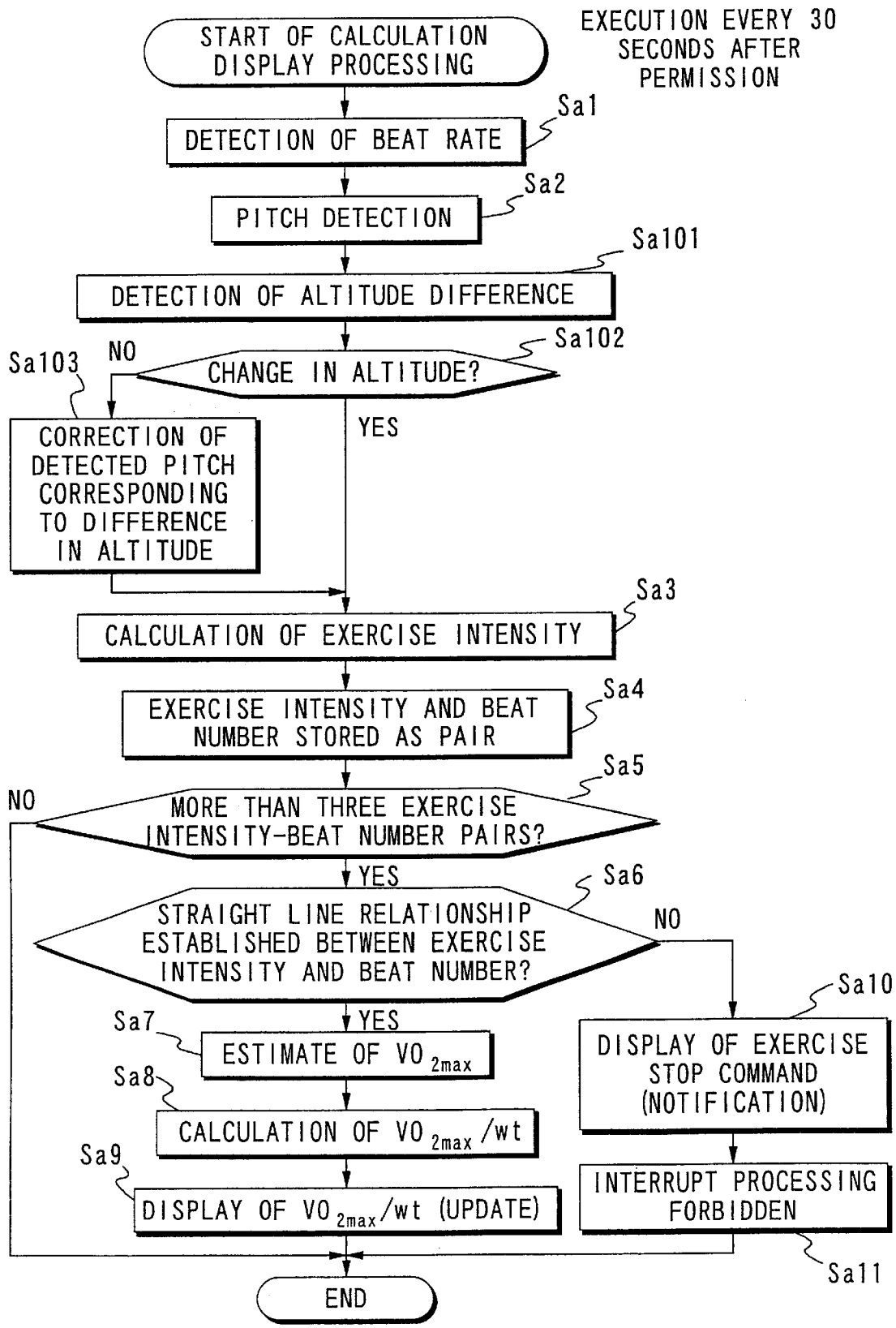
FIG. 12 is a flow chart showing the main operations in this same embodiment.

When the test subject is running, then the flow chart for calculation display processing, which is executed as an interrupt processing, becomes as shown in FIG. 12. As shown in this figure, the calculation display processing in this third embodiment has steps Sa101~Sa103 added to the processing shown in FIG. 7, immediately proceeding step Sa2.

Namely, when the pitch during running is detected in step Sa2, then, in step Sa102, CPU 201 obtains information regarding the altitude difference detected by altimeter 210. CPU 201 stores this information in RAM 203, and, in step Sa103, determines whether or not an altitude difference is present based on the obtained information.

If an altitude difference is not present at this point, or more specifically, if an altitude difference is not present during the running performed between the previous and current execution of calculation display processing, then this indicates that the test subject was running over a flat path. Therefore, the standard stride set in RAM 203 is employed without modification when calculating exercise intensity (step Sa3)

On the other hand, if an altitude difference is present, then, in step Sa103, CPU 201 first determines the slope from the aforementioned altitude difference and the distance run during the 30 seconds. Second, the stride correction coefficient corresponding to this slope is obtained by reading it out from the table. Third, the standard stride read out from RAM 203 is multiplied by the correction coefficient, to correct the stride corresponding to this slope. Accordingly, if there is an altitude difference present during running, then CPU 201 corrects the standard stride set in RAM 203, and employs this corrected stride to calculate exercise intensity (step Sa3).

Accordingly, the stride is corrected in response to the slope during running in this third embodiment. Moreover, this correction is matched to the individual characteristics of the test subject, so that it is possible to more accurately obtain the maximum oxygen uptake quantity ($VO_{2max}$/wt).

Note that it is also acceptable to obtain exercise intensity after taking into consideration the change in the positional energy of the test subject accompanying a change in altitude, irrespective of the change in stride due to the slope. In other words, it is also acceptable to provide a design in which the positional energy, which is expressed as the product of the altitude difference obtained from altimeter 210 and the test subject s body weight which is set in RAM 203, is added to or subtracted from (added when ascending a hill, and subtracted when descending a hill) the obtained exercise intensity.

Further, the maximum oxygen uptake quantity ($VO_{2max}$/wt) can be obtained even more accurately by combining both the second and third embodiments. Namely, if the stride set in RAM 203 is corrected to match the pitch and slope, then the maximum oxygen uptake quantity ($VO_2max$/wt) can be obtained even more accurately.

4. Embodiment 4

4.1. Basic structure and operation

The fourth embodiment according to the present invention will now be explained with reference to the figures.

Figure 13:
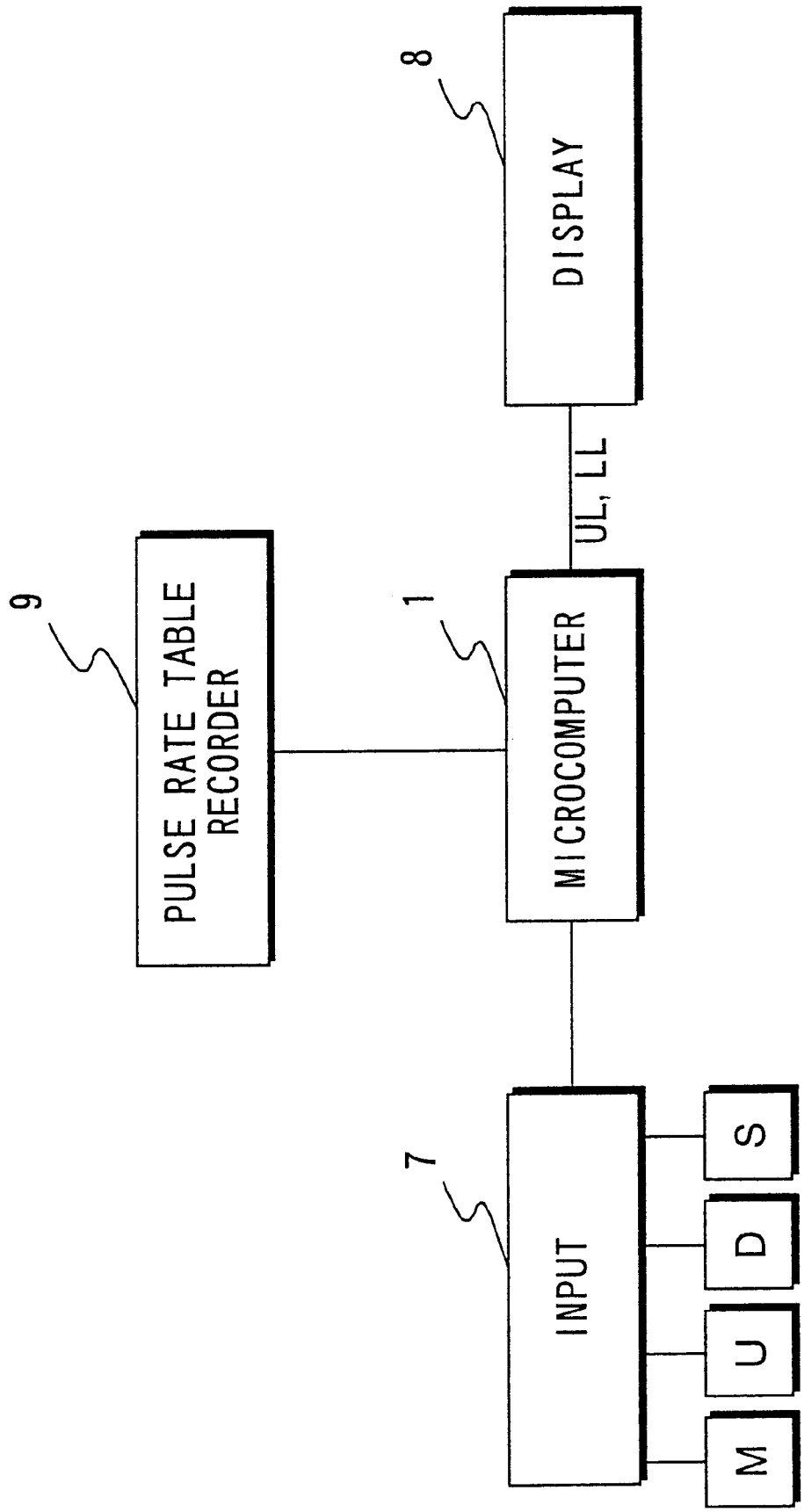
FIG. 13 is a block diagram showing an example of the structure of an exercise workouts support device according to a fourth embodiment of the present invention.

FIG. 13 is a block diagram showing an example of the structure of the exercise workout support device according to the fourth embodiment of the present invention.

In this figure, microcomputer 1 is composed of a CPU (central processing unit) and its peripheral circuits. Microcomputer 1 controls all parts of the device, and determines the upper limit UL and lower limit LL of the pulse rate.

Input 7 is provided with a mode switch M used in selecting each of the modes, an up switch U and a down switch D used to change the setting values, and a set switch S used to decide the setting values.

Display 8 is comprised of a liquid crystal display, and displays the upper limit UL and lower limit LL determined by microcomputer 1.

Pulse rate table recorder 9 is formed of ROM (read-only memory), and stores the pulse rate table shown below.

FIG. 14 is an explanatory figure showing an example of the pulse rate table.

As shown in this figure, this pulse rate table stores the pulse rate corresponding to the $VO_{2max}$ for each $VO_{2max}$.

In the figure, $VO_{2max}$ is the oxygen uptake quantity at the point in time when a given individual is exercising at his maximum intensity. $VO_{2max}$ is employed to indicate the oxygen uptake quantity, as well as the exercise intensity, such as, for example, exercise at a $VO_2max$ of 40 [ml/kg/min].

The pulse rate corresponding to each $VO_{2max}$ in this figure indicates the pulse rate when an average person for whom $VO_{2max}$ is the aforementioned value exercises at an intensity which corresponds to 50% of $VO_{2max}$.

Note that there are two types of pulse rate tables recorded in pulse rate table recorder 9 (i.e., for males and females). The table shown in FIG. 14 is for males.

The operation of an exercise workout support device according to the above structure will now be explained.

The user estimates his own $VO_{2max}$ in advance using the methods explained in the first through third embodiments, or by means of a conventional indirect method. In this case, there is available an indirect method wherein $VO_{2max}$/wt is estimated from heartbeat rate and power under maximum exercise (see Hoken-No-Kagaku (Science of Health), Vol. 32, No. 3, 1990.).

Next, the user turns on the power source for the device and presses mode switch M (see FIG. 13), thereby changing the display on display 8 to the state shown in FIG. 15(*a*).

In this state, when the user presses the up switch U (or the down switch D) one time, the display on display 8 changes from 1 (male) to 2 (female), or from 2 (female) to 1 (male). After matching the display to his or her sex in this way, the user then inputs the aforementioned value by pressing set switch S. As an example in this case, 1 (male) is input.

Once the sex of the user is input, microcomputer 1 reads out the pulse rate table corresponding to the input sex from among the two pulse rate tables (for males and females) stored in pulse rate table recorder 9. Since 1 (male) was input in this case, microcomputer 1 reads out the pulse rate table for males (see FIG. 14).

Next, the user presses mode switch M, causing the display on display 8 to change to the state shown in FIG. 15(*b*).

In this state, the display on display 8 is counted up when the user continues to press up switch U, or is counted down when the user continues to presses down switch D. Once the user has matched the display to his own $VO_{2max}$, he inputs this value by pressing set switch S. As an example in this case, 40 is input.

Once $VO_{2max}$ is input, microcomputer 1 reads out the pulse rate corresponding to this $VO_{2max}$ from the pulse rate table read out above (see FIG. 14). Here, since 40 was input, microcomputer 1 reads out the value 125 corresponding to the aforementioned value 40.

Next, microcomputer 1 determines the value of the upper limit UL for pulse rate by multiplying the read out pulse rate by a specific upper limit value coefficient 1.2 (i.e., 120%). In this example, since the aforementioned pulse rate was 125, the value of the upper limit becomes 150.

Similarly, microcomputer 1 determines the value of the lower limit LL for the pulse rate by multiplying the pulse rate read out above by a specific lower limit value coefficient 0.8 (i.e., 80%). In this example, since the aforementioned pulse rate was 125, the value of the lower limit becomes 100.

Finally, microcomputer 1 sends the upper limit UL and lower limit LL to display 8 where they are displayed.

4.2. Example application in pitch maker

Next, an explanation will be made of an example application in which the device is employed in a pitch maker.

4.2.1. Overall structure

The structure of a pitch maker in which this device is employed will be explained with reference to the figures.

Figure 16:
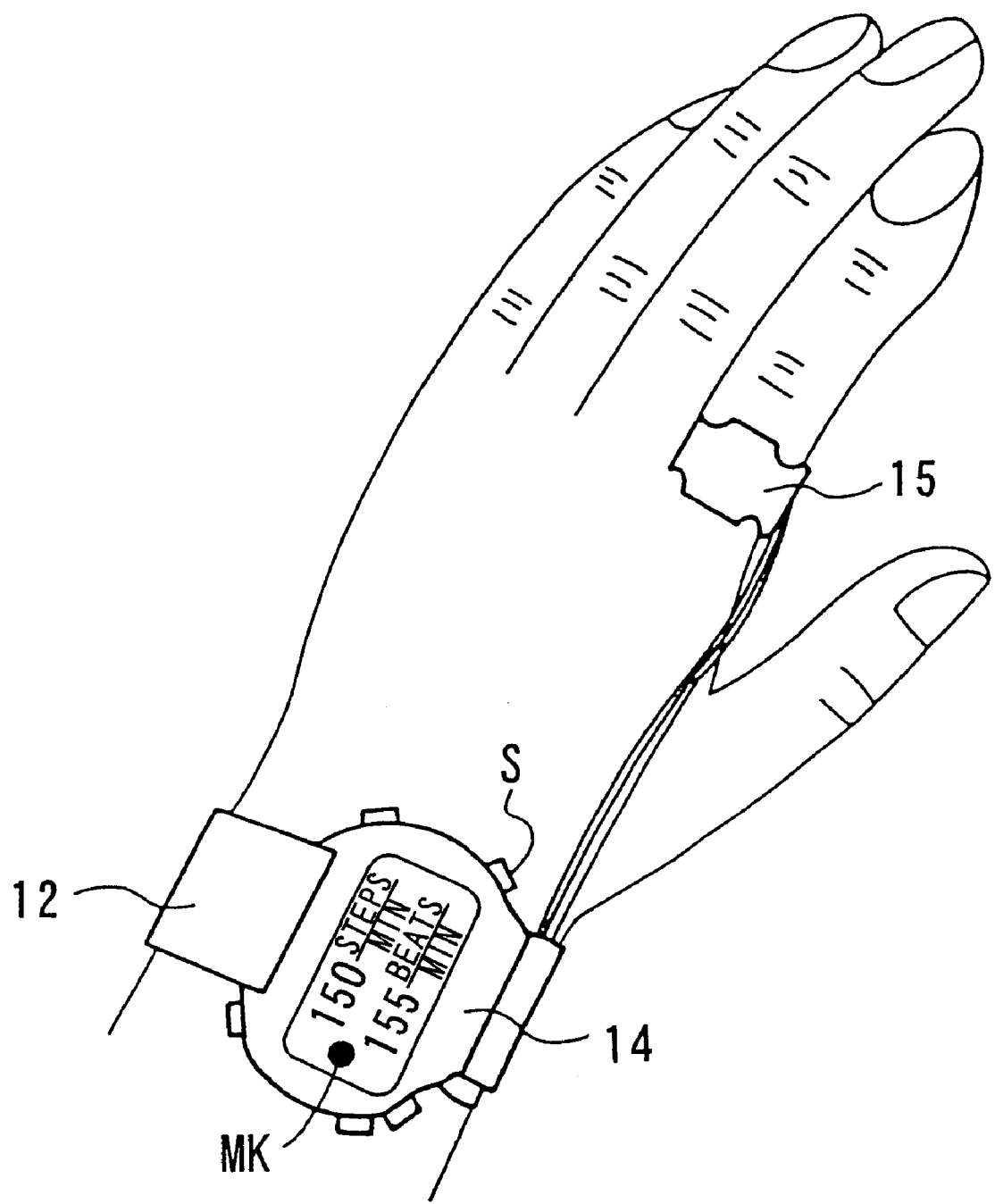
FIG. 16 is a slant view showing the outer appearance of the pitch maker employed by the exercise workout support device in this same embodiment.

FIG. 16 is a slant view of the outer appearance of the aforementioned pitch maker.

In this figure, the main body 14 of the device is attached to the arm of the user by means of a wrist band 12.

Pulse wave sensor 301 (see FIG. 19) and body motion sensor 302 (see FIG. 19), which will be explained below, are fixed in place to the finger by means of finger belt 15.

Figure 17:
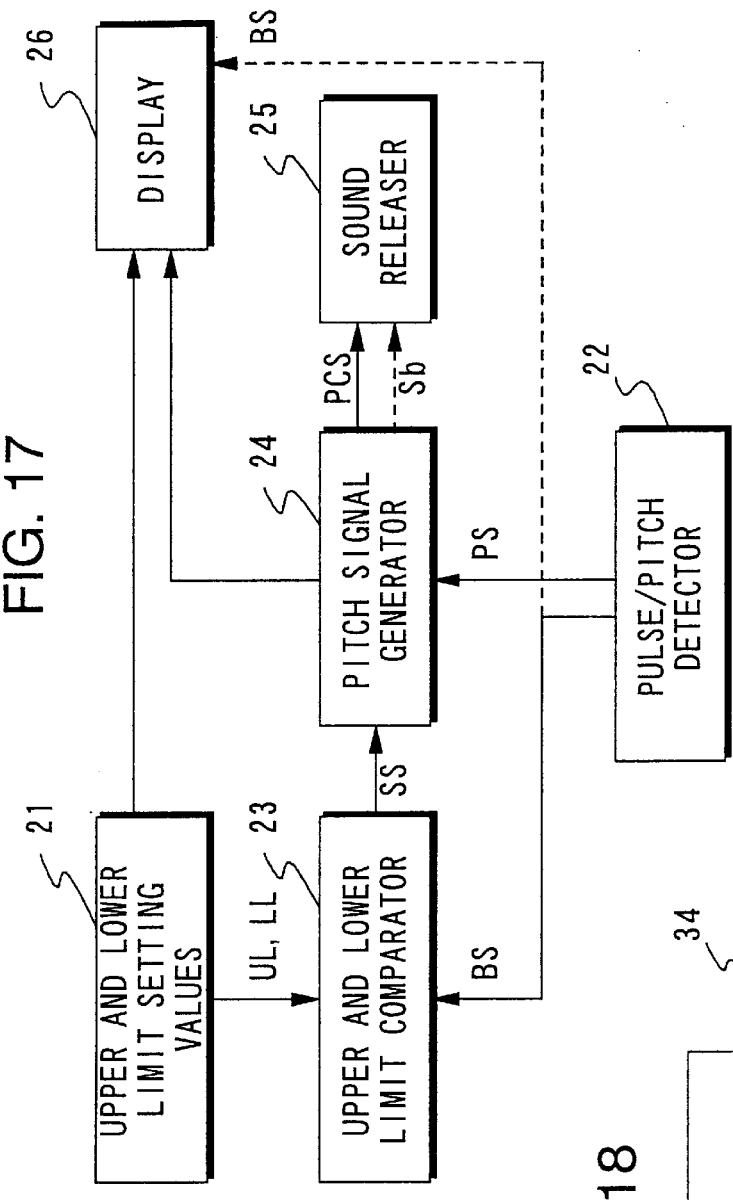
FIG. 17 is a block diagram showing an example of the electrical structure of the pitch maker.

Next, FIG. 17 is a block diagram showing an example of the electrical composition of the aforementioned pitch maker.

In this figure, upper and lower limit setting element 21 is the device according to the present invention which was already explained above under the section, Basic structure and operation. Upper and lower limit setting element 21 determines the upper limit UL and the lower limit LL of the pulse rate, and outputs these.

Pulse rate/pitch detector 22 detects the pitch and pulse of the user during exercise, and outputs a pitch detection signal PS and a pulse detection signal BS showing these values. The structure and operation of pulse/pitch detector 22 will be discussed in detail under (2) Pulse/pitch detector which follows below.

Upper and lower limit comparing element 23 detects whether or not the pulse indicated by pulse detection signal B which is supplied from the pulse/pitch detector 22 exceeds the lower limit LL or the upper limit LL. A signal SS expressing this state is output to pitch signal generator 24.

Pitch signal generator 24 is a circuit for forming a pitch control signal PCS based on the pitch detection signal PS supplied from pulse/pitch detector 22 and signal SS supplied from upper and lower limit comparing element 23. It has the structure shown in FIG. 18, for example.

Figure 18:
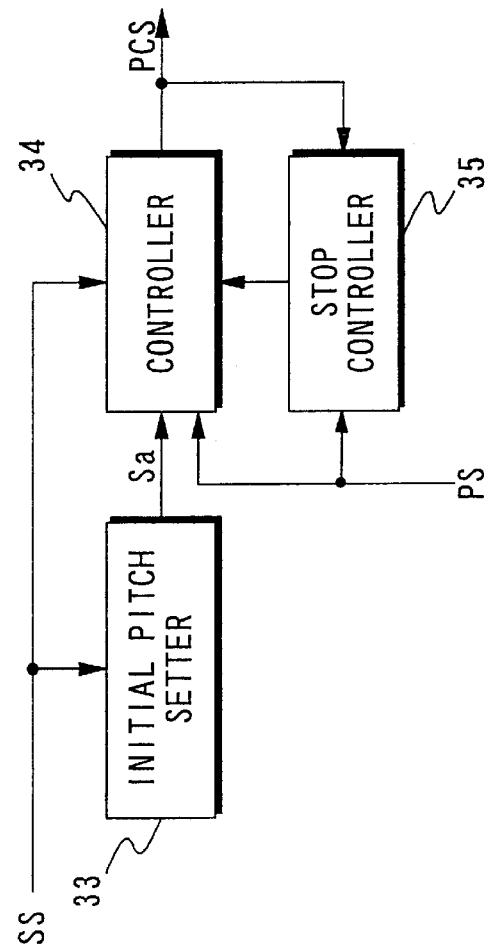
FIG. 18 is a block diagram showing an example of the structure of pitch signal generator 24.

In FIG. 18, the initial pitch setting element 33 is a circuit which detects the first time that the user s pulse rate exceeds the lower limit LL based on signal SS, and outputs a signal Sa to controller 34.

When signal Sa is supplied, controller 34 outputs the user s pitch which is indicated by pitch detection signal PS at that point in time as pitch control signal PCS.

Controller 34 checks the following signal SS after signal Sa has been output. When the user s pulse rate is found to be below the lower limit LL, then controller 34 adjusts pitch control signal PCS so that the pitch is increased at a fixed rate until the user s pulse rate is again above the lower limit LL.

In addition, controller 34 checks the signal SS which follows the output of signal Sa. When the user s pulse rate is found to be above the upper limit UL, then controller 34 adjusts pitch control signal PCS so that the pitch is lowered at a fixed rate until the pulse rate is again below the upper limit UL.

Stop control element 35 is a circuit for comparing pitch control signal PCS and pitch detection signal PS. Stop control element 35 stops the output of pitch control signal PCS when these signals are equivalent for fixed period of time (or when they are almost the same), and outputs the pitch control signal PCS again when the two signals are different. However, when changing (raising or lowering) pitch, controller 34 is designed to continue outputting pitch control signal PCS irrespective of the operation of stop controller 35.

The structure of pitch signal generator 24 and the details of processing where explained above. However, the present invention is not limited thereto, but rather, provided that the same processing is carried out, other circuit structures are possible. Additionally, it is also acceptable to realize the preceding by means of software.

Next, sound releaser 25 shown in FIG. 17 is formed of a piezoelectric buzzer and its drive circuit, for example, and releases a beeping sound at a pitch in accordance with pitch control signal PCS. When pitch control signal PCS is not supplied, then sound release is halted.

Display 26 is comprised of a liquid crystal display. As shown in FIG. 16, display 26 displays the pitch indicated by pitch control signal PCS as a numerical value, and turns mark MK on and off in response to that pitch. Further, display 26 displays a pulse rate based on pulse detection signal BS supplied from pulse/pitch detector 22. When the display mode is changed by means of the mode switch M (see FIG. 13) of upper and lower limit setting element 21, display 26 is designed to display the values of an upper limit UL and a lower limit LL (not shown in the figures).

4.2.2. Pulse/pitch detector

An explanation will now be made of the structure and operation of pulse/pitch detector 22 with reference given to the figures.

Figure 19:
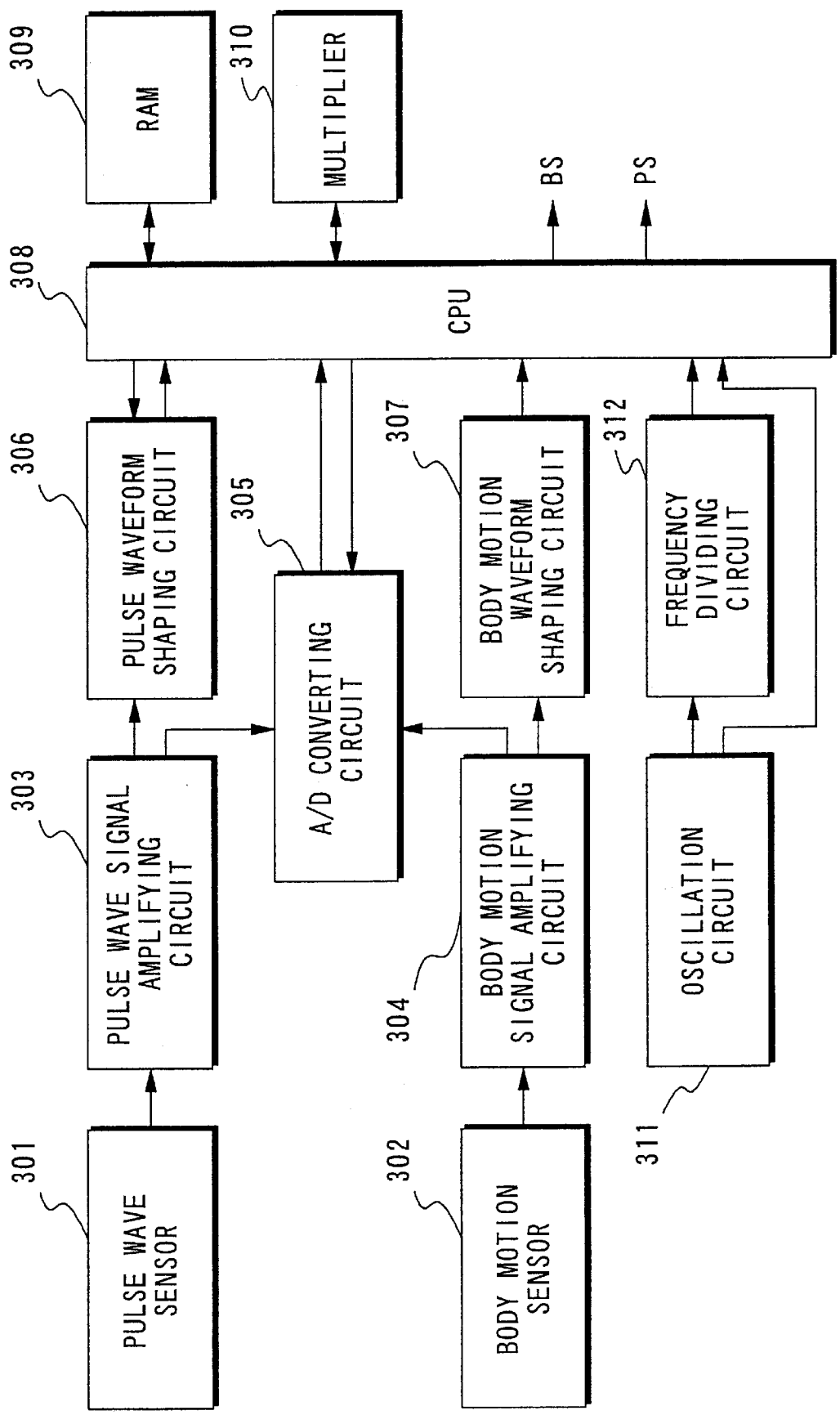
FIG. 19 is a block diagram showing an example of the structure of pulse/pitch detector 22.

FIG. 19 is a block diagram showing an example of the structure of pulse/pitch detector 22.

In this figure, pulse wave sensor 301 detects the pulse wave in the body, and outputs the detected pulse wave signal to a pulse wave signal amplifying circuit 303. Pulse wave sensor 301 may be a piezoelectric mike, for example.

Body motion sensor 302 detects body motion, and outputs the detected body motion signal to body motion signal amplifying circuit 304. Body motion sensor 302 may be an acceleration sensor, for example.

Pulse wave signal amplifying circuit 303 amplifies the detected pulse wave signal, and outputs the signal to A/D converting circuit 305 and pulse waveform shaping circuit 306.

Body motion signal amplifying circuit 304 amplifies the detected body motion signal, and outputs the signal to A/D converting circuit 305 and body motion waveform shaping circuit 307.

A/D converting circuit 305 converts the amplified pulse wave signal and body motion signal from analog to digital signals, and outputs this result to CPU 308.

Pulse waveform shaping circuit 306 shapes the amplified pulse wave signal, and outputs it to CPU 308.

Body motion waveform shaping circuit 307 shapes the amplified body motion signal, and outputs the result to CPU 308.

Figure 20:
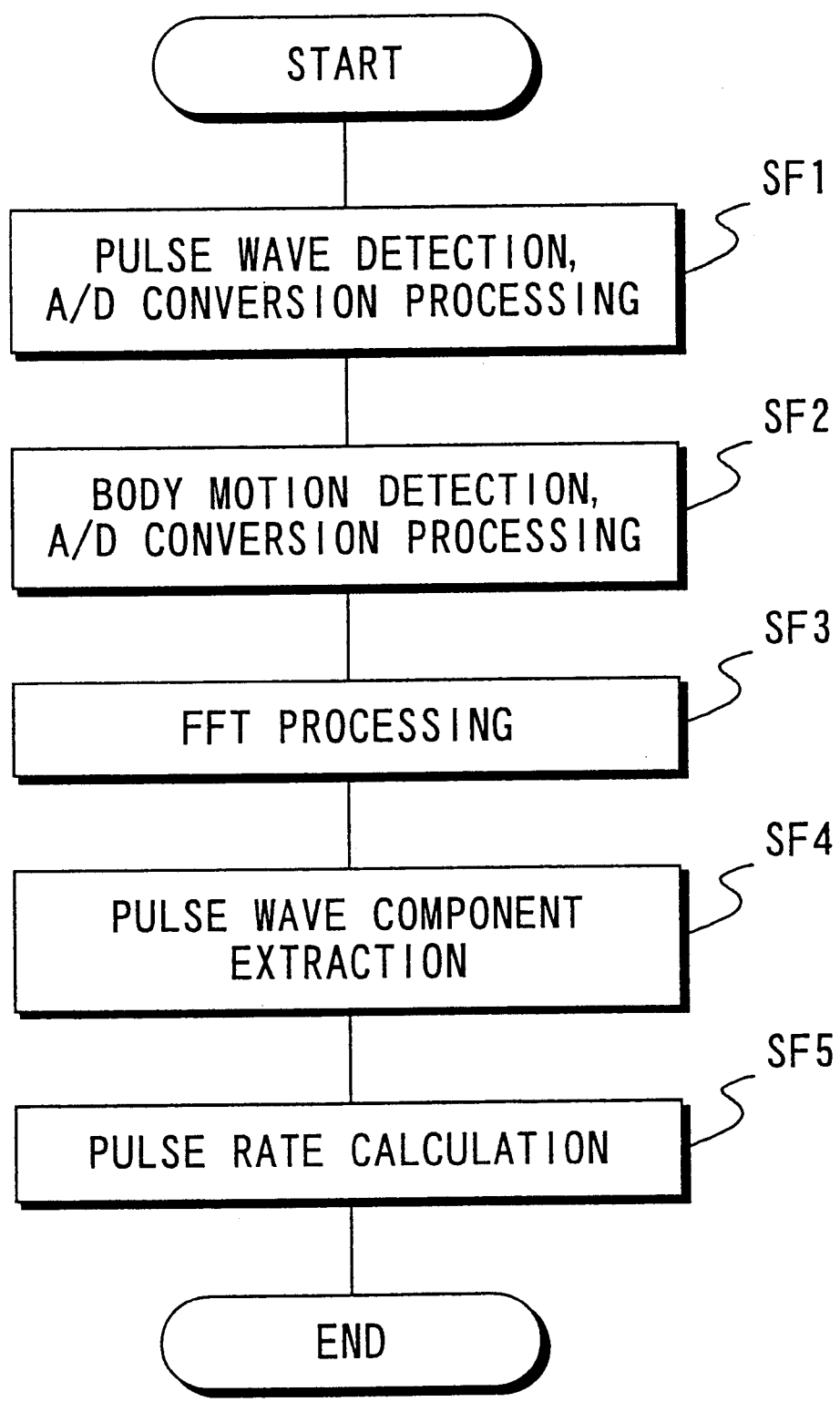
FIG. 20 is a flow chart showing the order of processing in pulse/pitch detector 22.

FIG. 20 is a flow chart showing the order of processing in pulse/pitch detector 22.

In step SF1 in this figure, the pulse wave is detected, the pulse wave signal is amplified, and the amplified pulse wave signal is converted from analog to digital.

At step SF2, body motion is detected, this body motion signal is amplified and the amplified body motion signal is converted from an analog to a digital signal.

At step SF3, the analog-to-digital converted pulse wave signal and body motion signal are subjected to FFT processing.

At step SF4, the beat frequency component is extracted based on the FFT processed pulse wave signal and body motion signal.

At step SF5, the pulse rate is calculated based on the extracted beat frequency component.

Beat frequency component as used in this specification is defined as the beat frequency component obtained after removing the frequency component corresponding to the body motion signal from the result obtained after FFT processing of the pulse wave signal.

4.2.2.1. Principle of processing to extract beat frequency component

The beat frequency component was extracted in step SF4 above. The principle behind this operation will now be explained.

FIG. 21A shows the signal obtained after adding frequencies fA and fB (where, however, the amplitude of frequency fB is ½ that of frequency fA). FIG. 21B is a graph showing the result obtained after FFT processing of the added signal.

The lowest frequency obtained as a result of FFT processing is determined according to the inverse of the duration of analysis. For example, if the duration of analysis was 16 sec, then the line spectrum is $\frac{1}{16}$ sec. In other words, a resolution of 62.5 msec is obtained. Accordingly, the signal which is subject to analysis is resolved to a harmonic wave component which is an integer multiple of 16 Hz. The size (power) of the respective harmonic components is expressed along the vertical axis. FIG. 21B shows that frequency fB has half the power of frequency fA.

FIG. 22A is a graph showing an example of the results obtained after carrying out FFT processing of the signal output from pulse wave sensor 301 and body motion sensor 302 during exercise. FIG. 22A shows the result (pulse wave spectrum $f_{mg}$) obtained after carrying out FFT processing to the signal output from pulse wave sensor 301; 22B shows the result (body motion spectrum $f_{sg}$) obtained after carrying out FFT processing to the signal output from body motion sensor 302; and 22C shows the beat spectrum fM obtained after subtracting the body motion spectrum $f_{sg}$ from the pulse wave spectrum $f_{mg}$.

As shown in those figures, the beat frequency component and the frequency component from the signal generated by body motion are both present in FIG. 22A.

In contrast, since body motion sensor 302 corresponds to body motion only, only the frequency component from the signal generated by body motion is obtained in FIG. 22B.

Accordingly, the body motion spectrum $f_{sg}$ is subtracted from the pulse wave spectrum $f_{mg}$, and the largest spectrum from among the remaining line spectrum fM is specified as the beat frequency component.

The pulse rate is calculated based on this beat frequency component in step SF5 shown in FIG. 20.

However, it may be difficult to actually carry out frequency analysis of the waveforms output from these sensors by means of the method of simply taking the difference, due to the influence of the harmonic wave signals. Accordingly, a more detained explanation will now be made of the method for specifying the pulse wave.

First we will consider the frequency range for analysis. Ordinarily, the frequency of body motion is 1~2 Hz. Accordingly, if $f_{max}$=4 Hz, then a check up through the third harmonic wave is sufficient.

In this embodiment, the maximum body motion component in the 2 to 4 Hz frequency region is extracted, and the maximum component therein is assumed to be the second harmonic wave of the body motion component. The reason for this assumption will now be explained.

Figure 23:
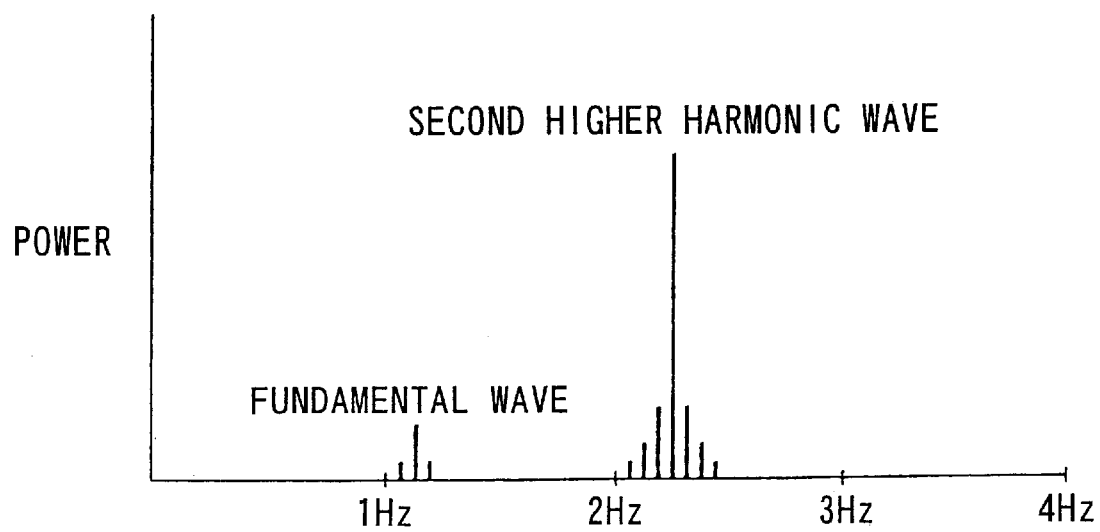
FIG. 23 is the result obtained after carrying out FFT processing on the output of body motion sensor 302.

FIG. 23 shows the results obtained after carrying out FFT processing on the output from body motion sensor 302. In general, when exercising, and particularly, when running, the power of the second harmonic wave becomes higher as compared to the fundamental wave (an increase of 3 to 10-fold, in the case of normal running, for example), as shown in FIG. 23. The following three points may be considered when analyzing the factors detected by body motion sensor 302 when the user is running. Namely, 1. upward and downward motion during running
2. the fundamental wave of arm swinging
3. the second harmonic wave of arm swinging With respect to (1), the upward and downward motion appears uniformly when taking a step with the right foot and when taking a step with the left foot, so that this motion becomes the second harmonic wave of the body motion component.

With respect to (2), a pendulum motion is indicated, in which the swinging forward and drawing back motion of the arms constitutes one period. Typically, however, it is difficult to render the swinging of the arms during running into a smooth pendulum motion, while the power of this component is weak.

With respect to (3), because acceleration is applied at the instant the arms swing forward and the instant they are drawn back, the second harmonic wave appears more strongly than the fundamental wave.

Accordingly, within the frequency of body motion, the second harmonic wave component is characteristically obtained.

In the case of ordinary running, given a range of 2 to 4 Hz, it is possible to cover the region in which the second harmonic wave appears, regardless of whether the pace of running is slow or fast. Accordingly, by extracting the characteristic second harmonic wave component after limiting the region in this way, it is possible to increase the accuracy of detection.

4.2.2.2. Details of processing to extract beat frequency component

Figure 24:
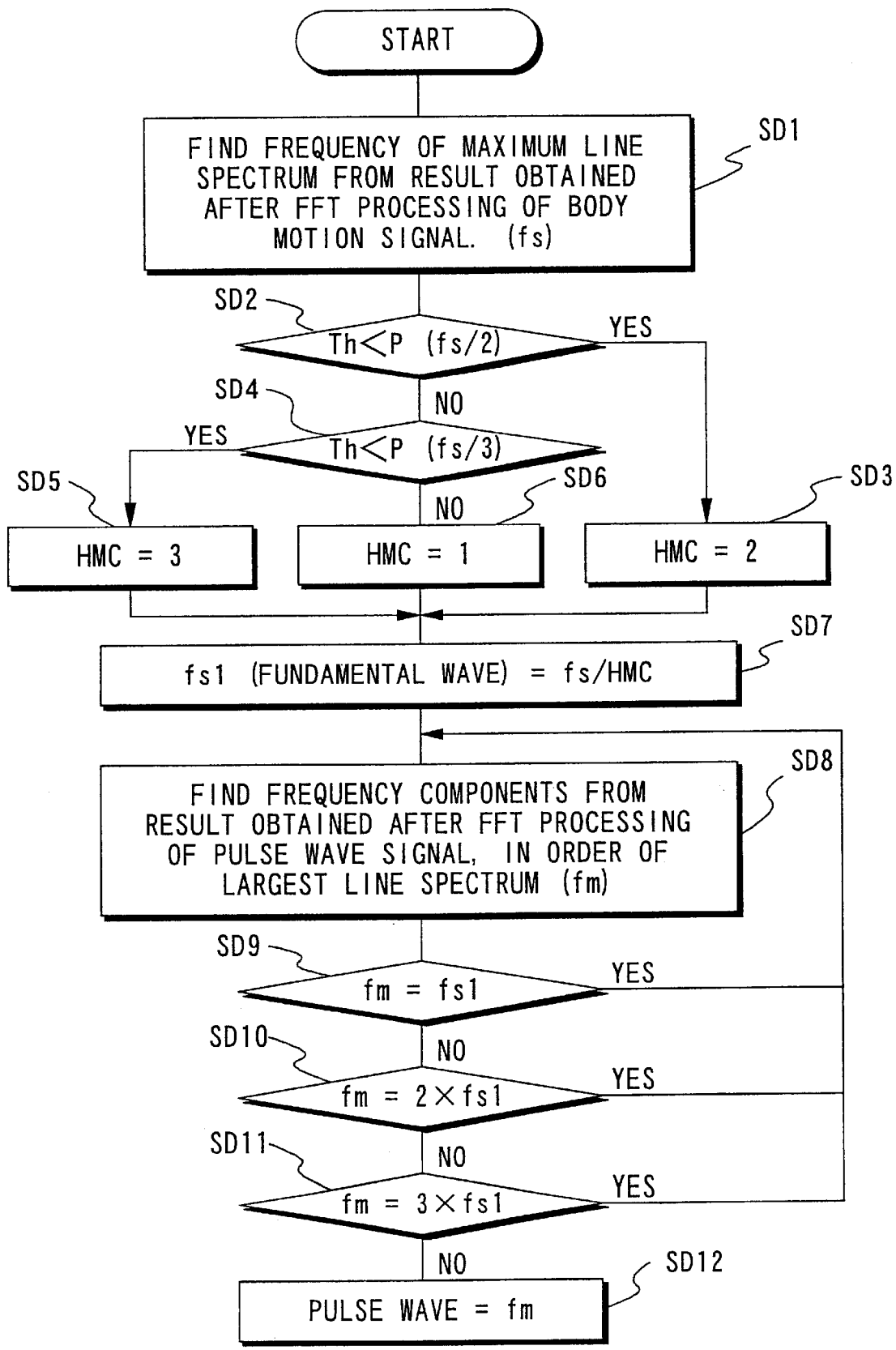
FIG. 24 is a flow chart showing the processing method for specifying the pulse wave component after specifying the harmonic wave of the body motion signal.

FIG. 24 is a flow chart for the processing method for specifying the pulse wave component after specifying the harmonic wave of the body motion signal.

In step SD1, CPU 308 determines the line spectrum fs at which power P is maximal, based on the results of frequency analysis of the body motion signal.

In steps SD2, CPU 308 decides whether or not a body motion component $P(f_s/2)$ above a given fixed value Th is present at a frequency position which is one-half that of frequency $f_s$.

When the result of this determination is YES, i.e., when a body motion component $P(f_s/2)$ above a given fixed value Th is present, then processing proceeds to step SD3.

In step SD3, frequency $f_s$ is specified as the second harmonic wave (HMC=2).

When the result of the determination in step SD2 is NO, i.e., when a body motion component $P(f_s/2)$ above a given fixed value Th is not present, then processing proceeds to step SD4.

In step SD4, CPU 308 decides whether or not a body motion component $P(f_s/3)$ above a given fixed value Th is present at a frequency which is ⅓ that of frequency $f_s$.

When the result of this determination is YES, i.e., when a body motion component $P(f_s/3)$ above a given fixed value Th is present, then processing proceeds to step SD5.

In step SD5, CPU 308 specifies fs as the third harmonic wave (HMC=3) of body motion.

When the result of the determination in step SD4 is NO, i.e., when a body motion component $P(f_s/3)$ above a given fixed value Th is not present, then CPU 308 specifies frequency $f_s$ as frequency $f_{s1}$ of the fundamental wave.

As a result of the preceding processing, it is possible to specify which of the harmonic waves is frequency $f_s$, so that in step SD7, the fundamental wave $f_{s1}$ of body motion is obtained.

In steps SD8~SD11, using the results of frequency analysis of the pulse wave, a comparison is made between the frequency fm and the body motion frequency for the line spectrums in sequential order starting with the line spectrum having the largest power P. In this way, a check is made as to whether or not that frequency coincides with the fundamental wave ($f_{s1}$), second harmonic wave ($2xf_{s1}$), or third harmonic wave ($3xf_{s1}$) of the body motion signal.

As a result of this processing, in step SD12, the maximum pulse wave frequency component $f_m$ which does not coincide with a body motion component can be extracted.

This concludes the explanation of the structure and operation of pulse/pitch detector 22.

4.2.3. Operation

The operation of the pitch maker will now be explained, with reference given to the figures.

First, upper and lower limit setting element 21 (i.e., the exercise workout support device according to the present invention) shown in FIG. 17 determines the upper limit UL and lower limit LL for pulse rate by means of the processing described above under the section titled Basic structure and operation.

Figure 27:
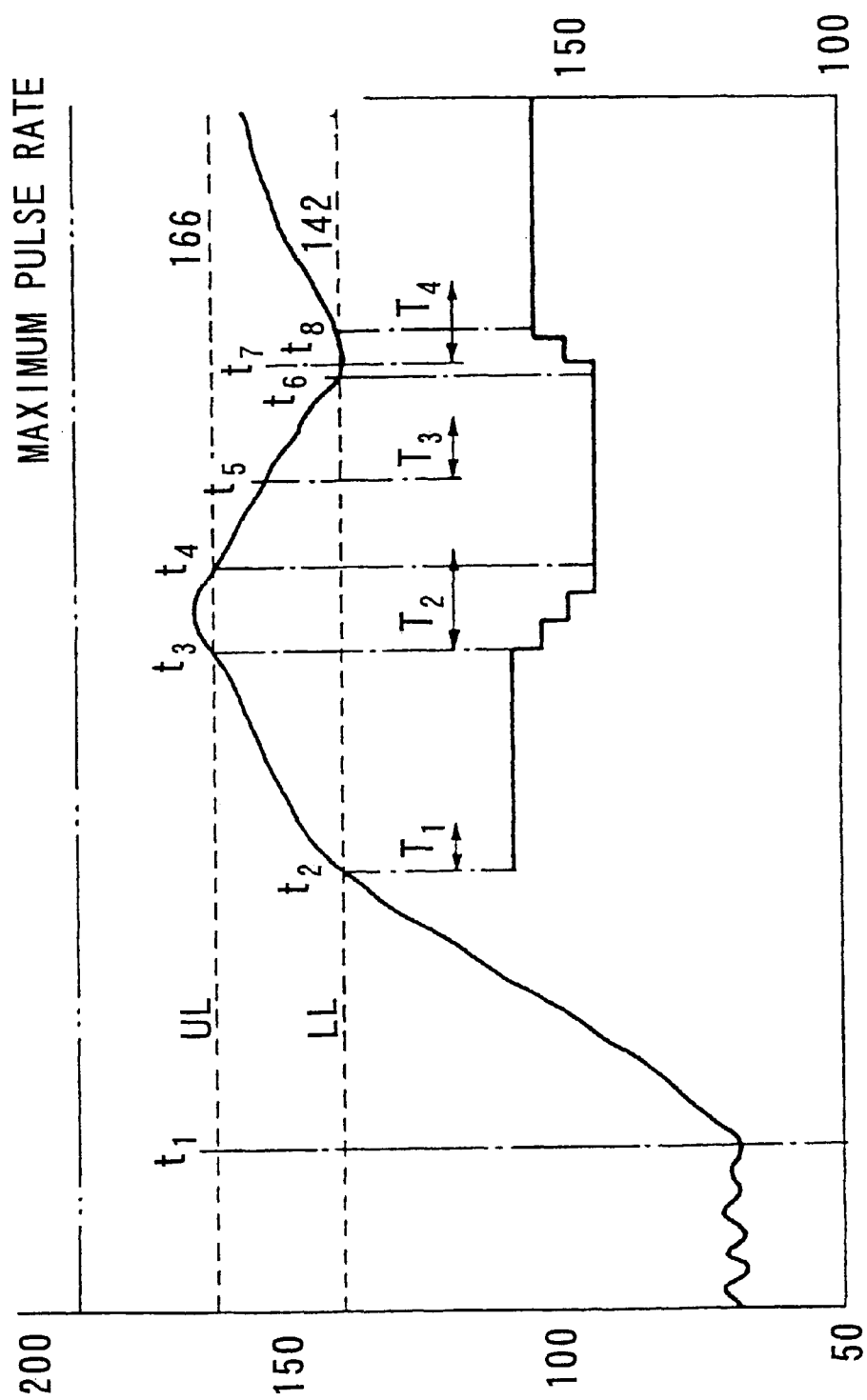
FIG. 27 is a timing chart for explaining the operation of the pitch maker.

Next, the finger belt 15 shown in FIG. 16 is attached to the finger, and running is initiated from time $t_1$ shown in FIG. 27, for example.

As a result, pulse/pitch detector 22 shown in FIG. 17 detects the user s pulse and pitch by means of the processing described in (2) pulse/pitch detector above, and outputs the pulse detection signal BS and the pitch detection signal PS expressing these values.

Upper and lower limit comparing element 23 compares pulse detection signal BS and upper limit UL and lower limit LL, and outputs signal SS corresponding to the result of this comparison.

In this case, when the user first begins running, his pulse does not reach the lower limit LL, as shown in FIG. 27. For this reason, initial pitch setting element 33 (see FIG. 18), does not output a signal Sa, and controller 34 does not carry out setting of the initial pitch. Accordingly, pitch control signal PCS is not generated, and sound releaser 25 does not generate a pitch sound.

Next, the user finishes warming up and the pitch gradually increases. Exercise intensity increases in accordance with the rising pitch, so that pulse rate rises.

At time $t_2$ shown in FIG. 27, the pulse rate indicated by pulse detection signal BS exceeds lower limit LL. Signal SS output by upper and lower limit comparing element 23 indicates [lower limit exceeded], and the initial pitch setting element 33 (see FIG. 18) outputs a signal Sa.

When signal Sa is output, controller 34 uptakes the user s pitch indicated by pitch detection signal PS, and sets this as that the initial pitch. Pitch control signal PCS is output in response to this pitch.

As a result, sound releaser 25 generates a pitch sound at a pitch corresponding to the pitch control signal PCS (the user s pitch at the current point in time, or 160 steps/min for the example shown in FIG. 27). In other words, when the user s pulse exceeds the lower limit LL, then the pitch sound is generated for the first time. Moreover, the interval during which sound is released is equivalent to the pitch of the user at that point in time.

Further, when the user s pitch and the pitch generated by sound releaser 25 are equivalent, and the duration of that equivalence exceeds a specific period of time, then stop controller 35 (see FIG. 18) outputs a control signal with respect to controller 34. As a result, pitch control signal PCS is terminated, and the pitch sound from sound releaser 25 ends. Accordingly, the release of the pitch sound at sound releaser 25 is carried out only from time $t_2$ to time $T_1$ shown in FIG. 27.

The reason for cutting off the pitch sound after the elapse of time $T_1$ is as follows. Namely, the pitch of a user who has entered a steady state in running is typically stable, so that, in the absence of any particular reason why this would not occur, running is carried out at an almost constant pitch even if a pitch sound or other directive is not provided.

Accordingly, the unnecessary pitch directive is not carried out, thereby reducing energy consumption.

Next, the pulse of the user running at the initial pitch rises as shown in FIG. 27. When the pulse exceeds the upper limit UL at time $t_3$, the output signal SS from upper and lower limit comparing element 23 indicates [upper limit exceeded]. Controller 34 (see FIG. 18) adjusts pitch control signal PCS so that the pitch is lowered at a fixed rate until the user s pulse falls below the upper limit UL.

Controller 34 again outputs a pitch control signal PCS when the pitch is changing, and outputs a pitch sound from sound releaser 25. This is required to make the user aware of the pitch change.

At time $t_4$, the user s pulse falls below upper limit UL, and controller 34 halts adjustment with respect to pitch control signal PCS. Accordingly, the setting pitch of controller 34 is fixed at the pitch immediately preceding time $t_4$ (145 steps/min). When the changed pitch and the user s pitch coincide for a fixed period of time, this is detected by stop controller 35, and pitch control signal PCS is again stopped.

Next, when the user s pitch changes at time $t_5$ due to some reason such as a change in physical condition, for example, then this is detected by stop controller 35. As a result, stop controller 35 outputs a pitch control signal PCS to controller 34. As a result, sound releaser 25 again releases a pitch sound, with the user varying the pitch of his running in accordance with the pitch sound. When the user s pitch and the setting pitch of controller 34 coincide for a fixed period of time, then the generation of pitch control signal PCS is stopped by stop controller 35. The user s pulse gradually falls, so that at time $t_6$, for example, it falls below lower limit LL. Since the output signal SS from upper and lower limit comparing element 23 indicates that the pitch has fallen below the lower limit, controller 34 adjusts the pitch control signal PCS so that the pitch increases at a fixed rate until the user s pulse exceeds the lower limit LL.

Controller 34 again outputs a pitch control signal PCS when the pitch changes, and causes a pitch sound to be output from sound releaser 25. In this case, there is a slight time difference from time $t_6$ when pulse fell below the lower limit LL and time $t_7$ when adjustment of pitch control signal PCS was initiated. This is because controller 34 monitors signal SS at specific periods. In the case of this example, the timing $t_7$ at which monitoring is carried out is slightly slower than the timing of time $t_6$. However, this does not present a problem since a sufficiently early period is set for the pitch directive to the user.

The pitch sound generated at time $t_7$ is halted after the elapse of time $T_4$. This is accomplished under the control of stop controller 35 in the same manner as described above.

This concludes the explanation of the operation of the pitch maker.

5. Embodiment 5

5.1. Structure of the embodiment

5.1.1. Overall structure

The fifth embodiment of the present invention will now be explained with reference to the figures.

Figure 29:
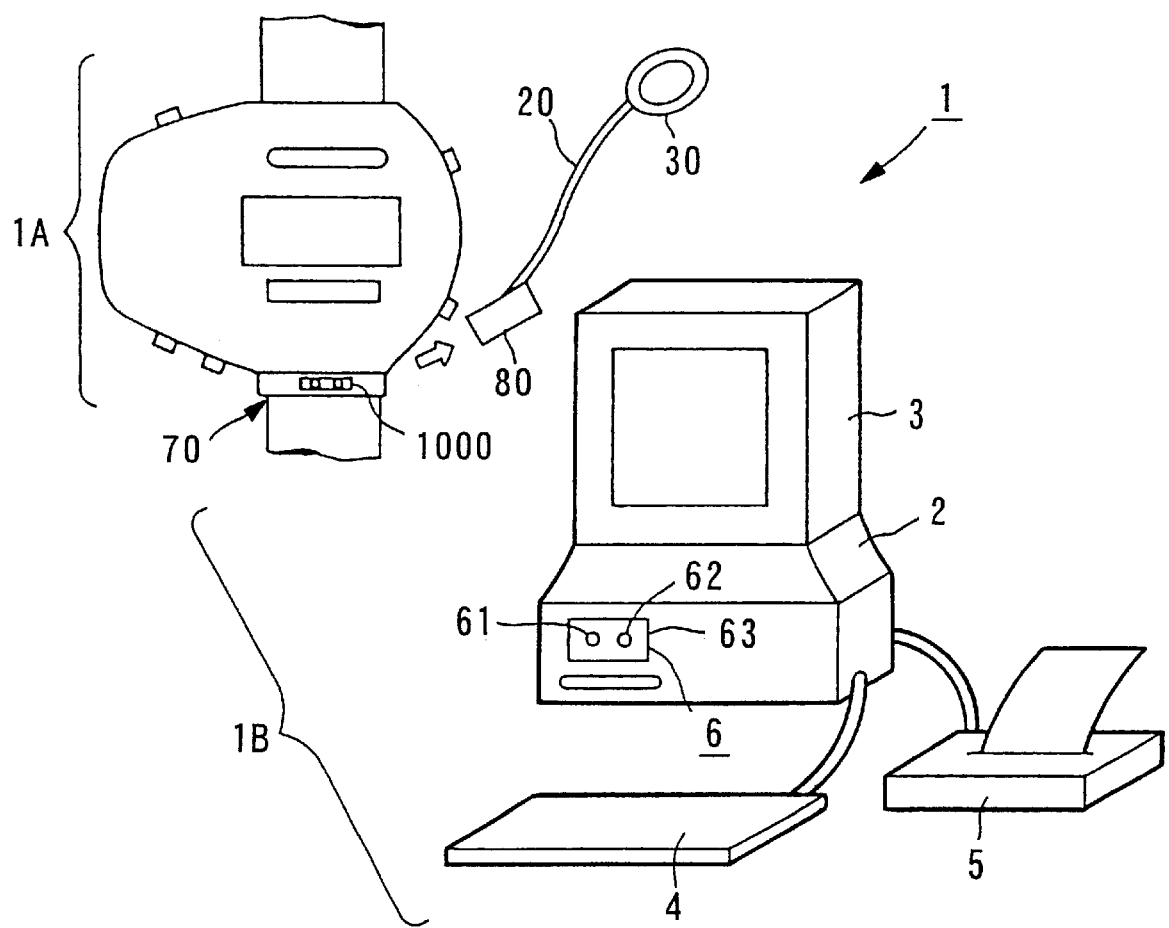
FIG. 29 shows the structure of the portable pulse wave measuring device and a data processing device for processing pulse wave data measured by the aforementioned device, according to the fifth embodiment of the present invention.
Figure 30:
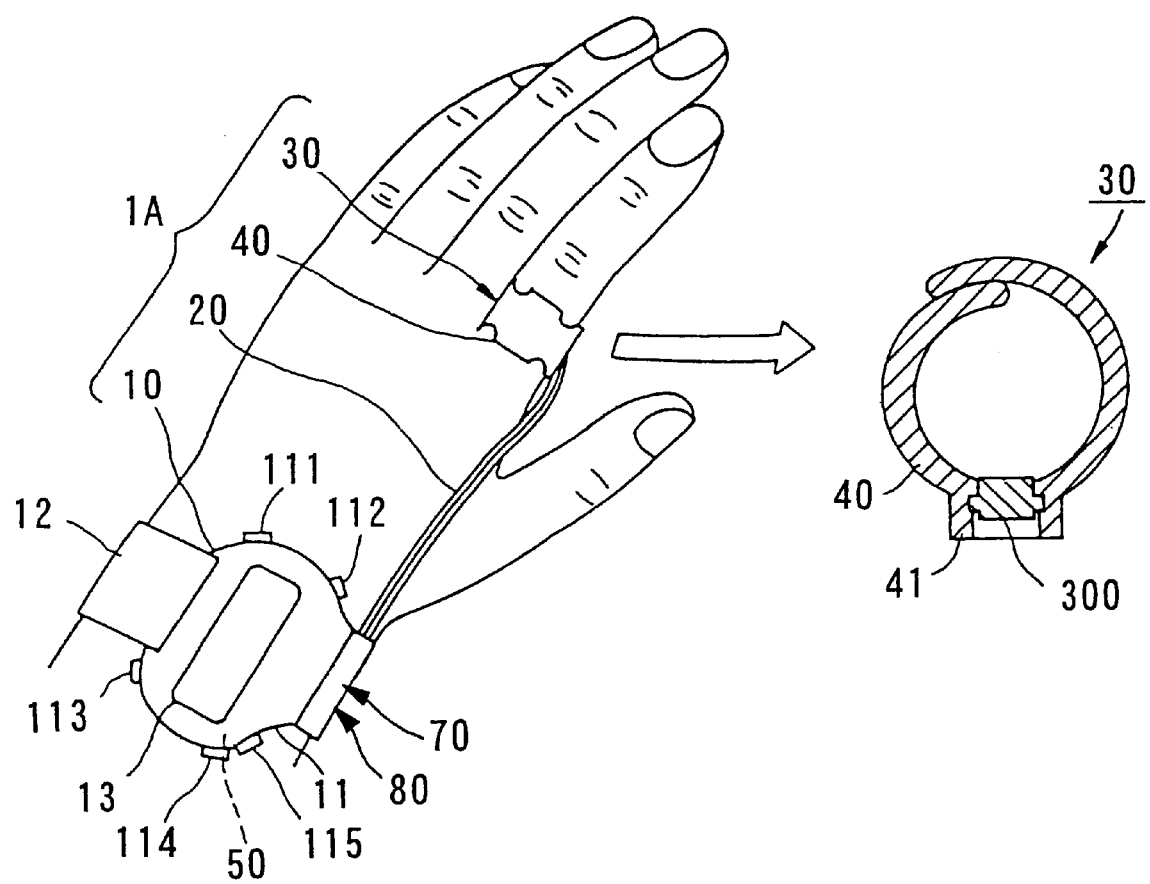
FIG. 30 shows the method of use for a pulse wave measuring device attached to the arm according to the same embodiment.

FIG. 29 shows the portable pulse wave measuring device and the data processing device for processing the information measured by this portable pulse wave measuring device, according to the present embodiment. Hereinafter, these will collectively be referred to as pulse wave information processing device . FIG. 30 is an explanatory figure showing the method of application for portable pulse wave measuring device. As may be understood from these figures, the portable device in this embodiment takes the form of a pulse wave measuring device which attaches to the arm which employs a wristwatch. As shown in FIG. 29, pulse wave information processing device 1 is formed of pulse wave measuring device 1A which attaches to the arm, and data processing device 1B which sends data between itself and pulse wave measuring device 1A which attaches to the arm.

As will be explained later, a connector 70 is provided to pulse wave measuring device 1A which attaches to the arm. Communications unit 100 for communicating with data processing device 1B is attached to connector 70. This communications unit 100 is employed to send data which uses an optical signal between pulse wave measuring device 1A which attaches to the arm and data processing device 1B. Communications unit 100 is designed to be freely releasable from pulse wave measuring device 1A which attaches to the arm. As will be explained below, connector piece 80 may be attached to connector 70 in place of communications unit 100, with a sensor unit 30 for measuring the pulse wave provided to the end of connector piece 80 via a cable 20.

Data processing device 1B is formed of a device main body 2, display 3, key board 4, printer 5, and the like. With the exception of the following points, it is formed in the same manner as an ordinary personal computer. Accordingly, a detailed description thereof is omitted. Namely, data processing device 1B internally houses a transmission controller and a receiving controller, which are not shown in the figures, for sending and receiving data by means of optical signals. The transmission controller is provided with LED 61 for sending optical signals, and the receiving controller is provided with a photo transistor 62 for receiving optical signals. LED 61 and photo transistor 62 employ near infrared (having a central wavelength of 940 nm, for example), and carry out optical communications via a visible light cutting filter 63 for blocking visible light, and through a communications window 6 used for optical communications which is provided to the front surface of data processing device 1B.

Next, in FIG. 30, the pulse wave measuring device 1A which attaches to the arm is roughly composed of a device main body 10 having a wristwatch structure, a cable 20 attached to device main body 10, and a sensor unit 30 provided to the end of cable 20. A wrist band 12 is provided to device main body 10 and is wrapped around the arm from the 12 o clock position, and fixed in place at the 6 o'clock position. This device main body 10 is designed to be freely detachable from the arm of the user by means of wrist band 12. Sensor unit 30 is provided with a band 40, which has a width of about 10 mm, for fixing the sensor in place. This band 40 for fixing the sensor in place is attached between the base and the joint of the index finger.

Note that when expressing direction according to time positions on a watch face, this refers to direction on the device main body, and does not mean that the display on the surface of the device main body takes the form of watch hands.

5.1.2. Structure of the main body of the device

The other components in FIG. 30 will now be explained with reference to FIG. 31, which is a planar view of the main body of pulse wave measuring device 1A which attaches to the arm.

In FIG. 30, device main body 10 is provided with a resin watch case 11. A liquid crystal display device 13 is formed to the surface of watch case 11 for displaying the current time and date, as well as pulse rate and other pulse wave information in digital form.

A data processor 50 which carries out signal processing on the detected result is housed in watch case 11, for displaying change in the pulse rate based on the result of detection by sensor unit 30 (i.e., pulse wave signal). A watch component is also formed in data processor 50, so that it is possible to display regular time, lap time sprint time and the like on liquid crystal display 13.

Button switches 111~115 are formed abut the outer periphery of watch case 11 for changing the various modes such as the time setting mode, display mode, pulse wave measuring mode, stop watch mode, data transmission mode and the like, while button switches 116~117 (not shown in FIG. 30) are formed to the surface of watch case 11.

Figure 31:
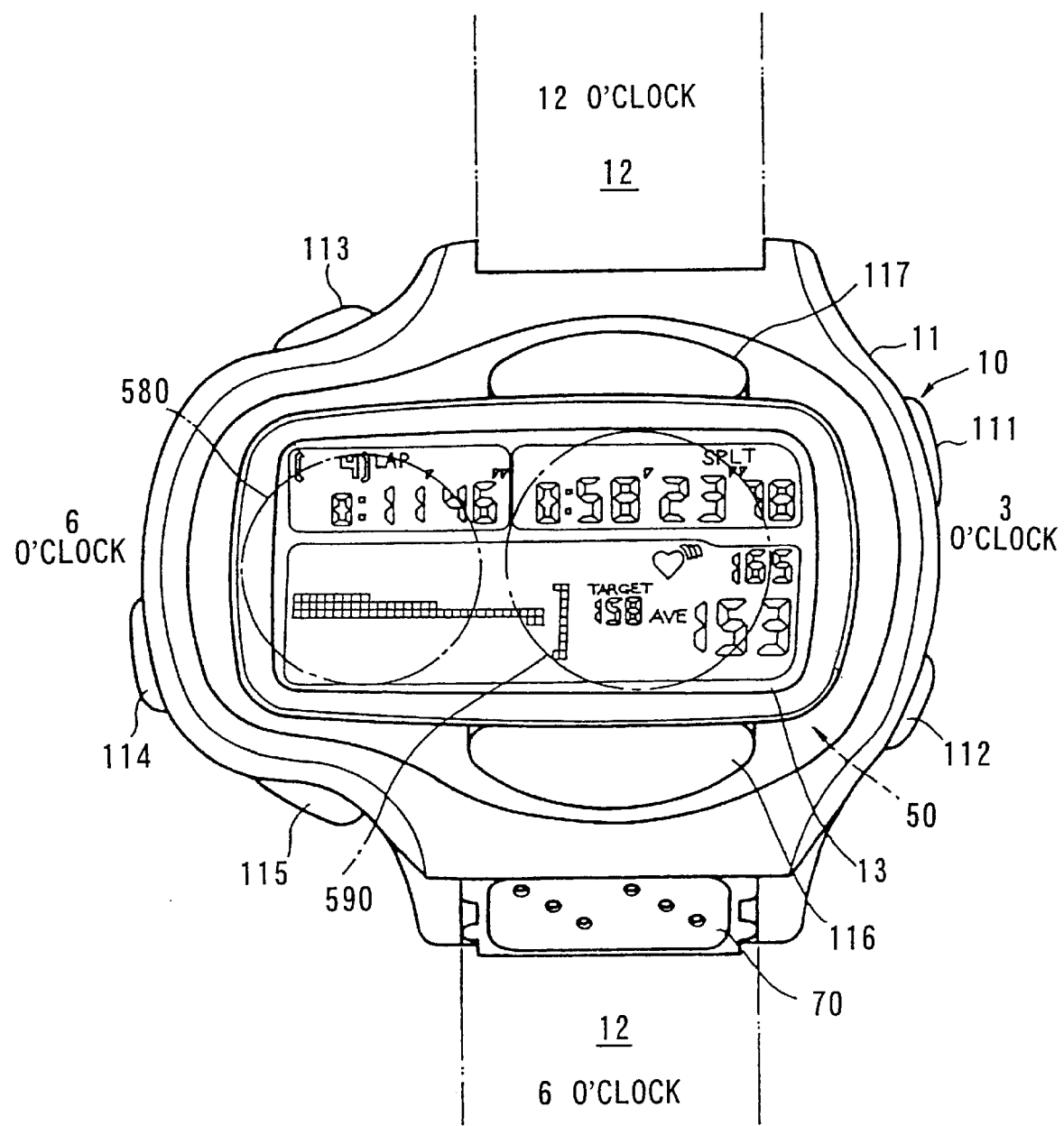
FIG. 31 is a planar view of the main body of this measuring device.

A flat button-shaped battery 590 is housed in watch case 11, as shown by the dashed line in FIG. 31, and is the power source for pulse wave measuring device 1A which attaches to the arm. Cable 20 supplies electric power from battery 590 to sensor unit 30, and inputs the results of detection by sensor unit 30 to data processor 50 inside watch case 11. Watch case 11 is longer in the horizontal direction. This feature is utilized to dispose battery 590 and flat piezoelectric element 580 for the buzzer next to one another in the planar direction inside watch case 11. As a result, it is possible to make device main body 10 thinner.

5.1.3. Structure of the sensor unit

As shown in FIG. 30, sensor unit 30 is composed of a band 40 for fixing the sensor in place and an optical unit 300. Band 40 for fixing the sensor in place is formed from a thick resin molded article which is flexible. Band 40 for fixing the sensor in place, which wraps around to form a circle, is pulled apart and wrapped around the base of the finger. When released, band 40 for fixing the sensor in place then wraps closely around the base of the finger under their intrinsic restorative force. Band 40 for fixing the sensor in place is thicker around the middle region thereof, where a hole 41 is formed for housing optical unit 300.

Figure 32:
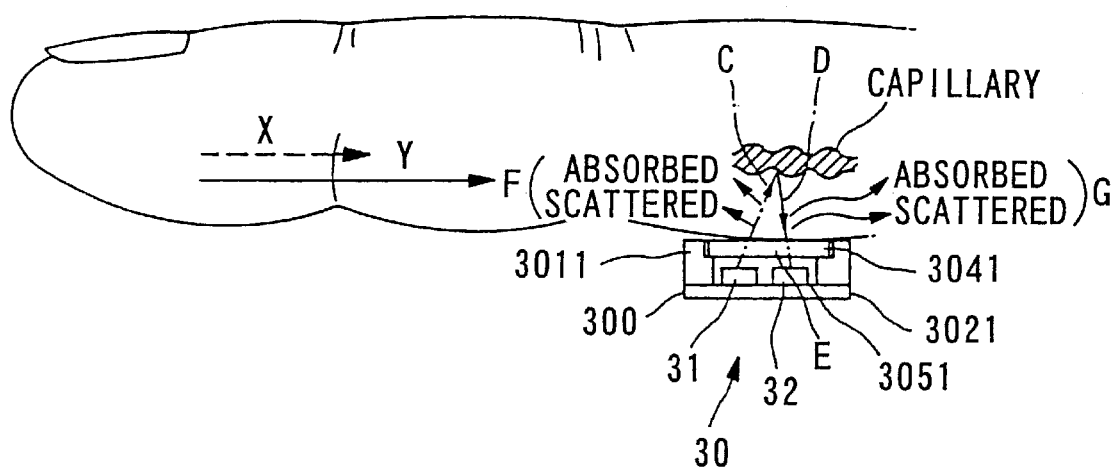
FIG. 32 shows an arrangement in which the sensor unit is attached to the finger in this measuring device.

Next, in FIG. 32, a rear cover 3021 covers the sensor frame 3011 of optical unit 300 as a case therefor, so that the internal area forms a component housing space. A light transparent window is formed in the upper portion of sensor frame 3011 by means of a glass plate 3041 (filter). A circuit board 3051 is fixed to the inner part of sensor frame 3011 so as to oppose glass plate 3041. Electrical components such as LED 31 used for pulse wave measurement, photo transistor 32 used for pulse wave measurement, transistors (not shown), and the like are mounted in circuit board 3051. The light emitting surfaces of LED 31 used for pulse wave measurement and the light receiving surface of photo transistor 32 used for pulse wave measurement are oriented in the direction of glass plate 3041.

Regarding optical sensor 300, when band 40 for fixing the sensor in place is attached to the base of the finger so that glass plate 3041 is attached on the inside with respect to band 40 for fixing the sensor in place, then the light emitting surface of LED 31 used for pulse wave measurement and the light receiving surface of photo transistor 32 used for pulse wave measurement are each directed toward the surface of the finger. Accordingly, when the finger is irradiated with light from LED 31 used for pulse wave measurement, then photo transistor 32 used for pulse wave measurement receives the light reflected by the blood vessels in the finger. The received light result (i.e., pulse wave signal) is input to device main body 10 from optical unit 300 via a cable 20.

Sensor unit 30 employs an LED 31 used for pulse wave measurement which has an emitted light wavelength region of 350~600 nm, and a photo transistor 32 used for pulse wave measurement which has a received light wavelength region of 300~600 nm. Physiological information is displayed based on the result of detection in the region of overlap therebetween, i.e., approximately 300~600 nm. In the case of outside light, it is difficult for light in the wavelength region below 700 nm to pass through the finger. Thus, even if outside light irradiates a portion of the finger not covered with band 40 for fixing the sensor in place, it employs the finger as a light guide as shown by dashed line X in the figure, but does not reach photo transistor 32 used for pulse wave measurement. Rather, only light in wavelength regions which will not impact detection travel using the finger as a light guide. Light in the low wavelength region of 300 nm or less is almost entirely absorbed by the skin surface. Thus, even if the wavelength region of the received light is set to 700 nm or less, the actual wavelength region of the received light is 300 to 700 nm. Accordingly, it is possible to restrict the impact of outside light, without significantly covering the finger, but rather by means of just covering a minimal area. Further, provided that a small sensor unit 30 is employed as in this embodiment, the device according to the present invention presents no impediment to running since the device can be grasped in the hand when attached to the base of the finger.

A portion of the light emitted from LED 31 used for pulse wave measurement reaches the blood vessels via the finger as shown by arrow C in the figure. Light reflected by the hemoglobin in the blood reaches photo transistor 32 used for pulse wave measurement as shown by arrow D. The light quantity received along this path is the quantity of light reflected by the body. Further, a portion of the light emitted from LED 31 used for pulse wave measurement is reflected by the surface of the finger as shown by arrow E, and reaches photo transistor 32. The quantity of light received along this path is the quantity of light reflected by the skin. A portion of the light emitted by LED 31 used for pulse wave measurement and a portion of the light reflected by the blood vessels is absorbed or scattered inside the finger as indicated by arrows F and G, and thus does not reach photo transistor 32 used for pulse wave measurement.

5.1.4. Structure of the data processor

Figure 33:
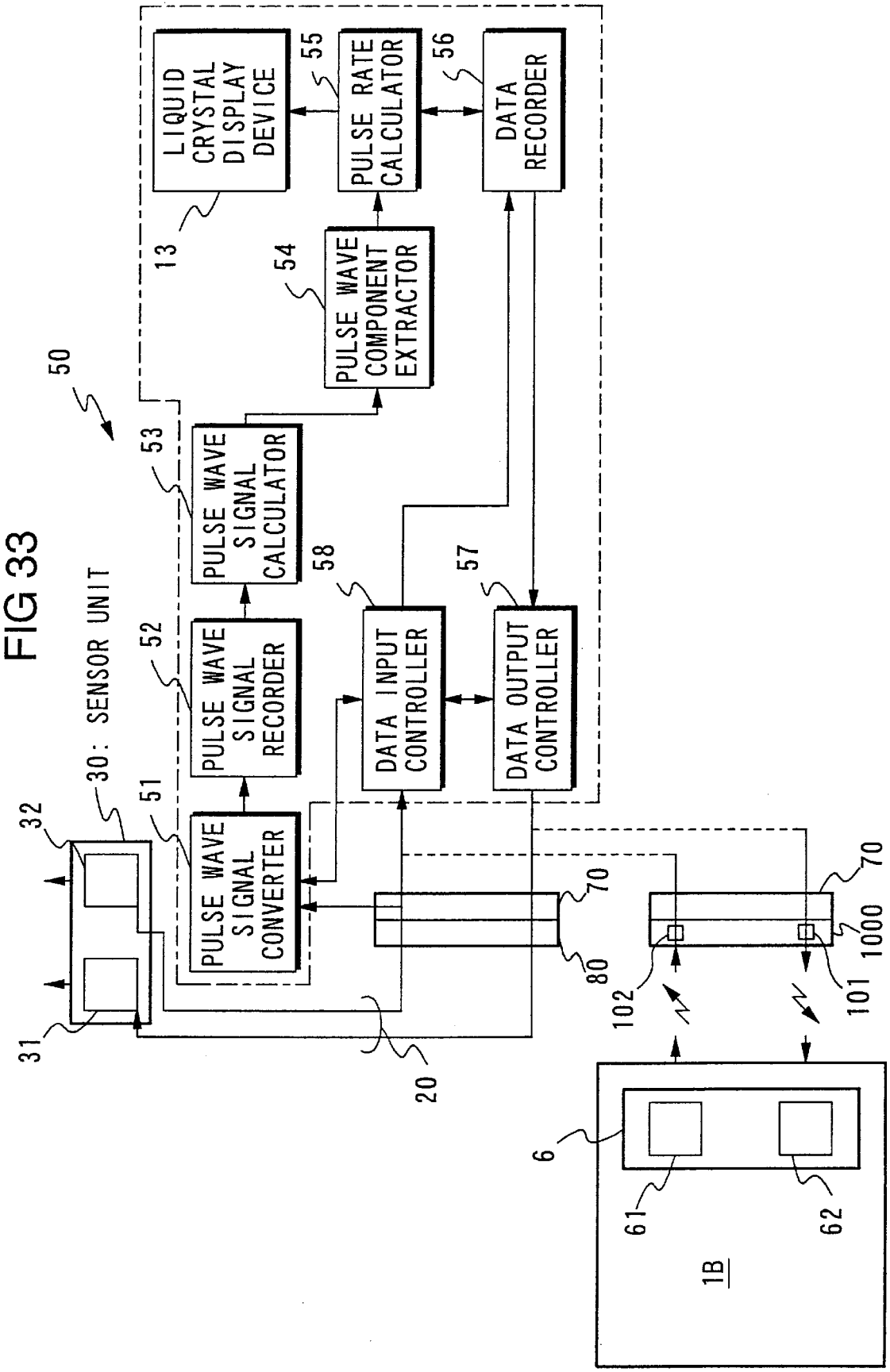
FIG. 33 is a block diagram showing the data processor of this measuring device.

The pulse rate is obtained in device main body 10 from the pulse wave signal described above. FIG. 33 is a block diagram of part of the functions of data processor 50 formed inside watch case 11. In this figure, pulse wave signal converter 51 converts the signal input from sensor unit 30 via cable 20 to a digital signal, and output this digital signal to pulse wave signal recorder 52. Pulse wave signal recorder 52 is a RAM (random access memory) for storing digitized pulse wave data. Pulse wave signal calculator 53 reads out the pulse wave data stored in pulse wave signal recorder 52, and inputs the result obtained after frequency analysis to pulse wave component extractor 54. This pulse wave component extractor 54 extracts the pulse wave component from the signal output from pulse wave signal calculator 53, and outputs this to pulse rate calculator 55. Pulse rate calculator 55 calculates the pulse rate from the frequency component of the input pulse wave, and outputs this result to liquid crystal display device 13.

A data recorder 56 is formed to data processor 50 for storing pulse wave information obtained by pulse rate calculator 55, time data corresponding to this pulse wave information, the sprint or lap time during a marathon which is measured using the watch function of pulse wave measuring device 1A which attaches to the arm.

Communications unit 100 may be attached to connector 70 in place of connector piece 80, with the following components functioning in the case where pulse wave measuring device 1A which attaches to the arm is set in the data transmission mode. Namely, data output controller 57 outputs pulse wave information and time data stored in data recorder 56 to data processor 1B via communications unit 100 as an optical signal. Data input controller 58 receives the optical signal sent from data processor 1B via communications unit 100, and stores it in data recorder 56.

5.1.5. Structure of the connector

So that pulse wave measuring device 1A which attaches to the arm can be used as an ordinary wristwatch during normal activities, connector piece 80 and communications unit 100 shown in FIG. 29 are designed to be releasable at the surface of the edge positioned at the 6 o clock position of the device main body. By positioning connector 70 at the 6 o clock position, the connector is disposed on the side of the watch which is nearer the user's body when device main body 10 is attached to the arm. Thus, it is easily manipulated by the user. Further, since connector 70 does not extend outward from the 3 o'clock side of device main body 10 of the wrist watch, the user can freely move his wrist during exercise. Even if the user falls during exercise, the back of the hand does not hit connector 70.

Figure 34:
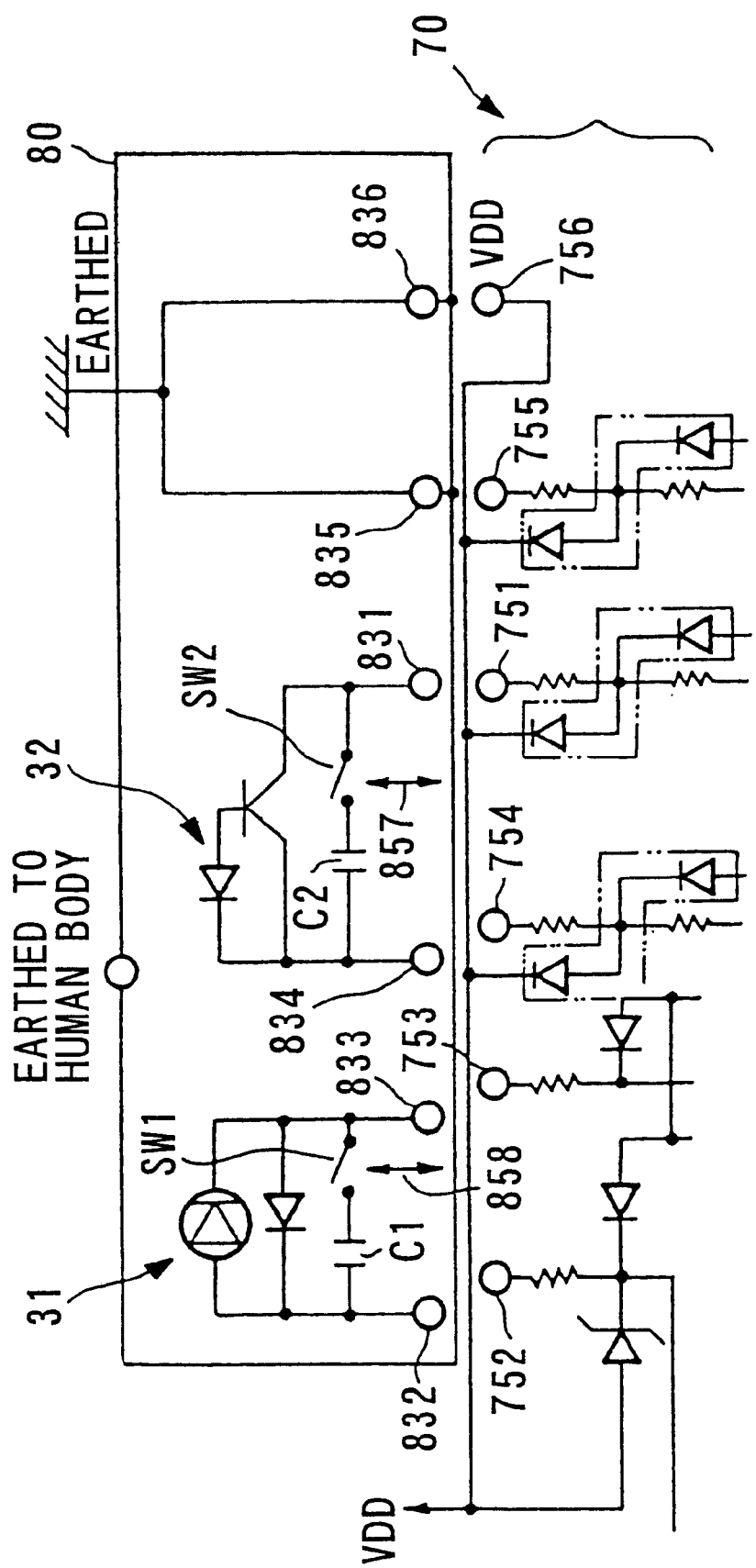
FIG. 34 shows the relationship between electrical connections in the connector of this measuring device.

FIG. 34 shows the electrical connection between connector 70 and connector piece 80 or communications unit 100. This figure shows the combination of a sensor circuit electrode on the connector piece 80 side, and a terminal on the connector 70 side for carrying out the input and output of signals with this sensor circuit. This figure shows the case where connector 70 and connector piece 80 are connected, however, this is entirely equivalent to the case where communications unit 100 is connected in place of connector piece 80.

In FIG. 34, terminals 751-756 are formed to connector 70. Electrodes 831~836 are formed to connector piece 80 corresponding to these terminals. Terminal 752 is a positive terminal for supplying drive voltage VDD to LED 31 used for pulse wave measurement via electrode 832, and terminal 753 is a negative terminal for LED 31 used for pulse wave measurement via electrode 833. Terminal 754 supplies a constant drive voltage to the corrector terminal of photo transistor 32 for measuring pulse waves via electrode 834.

Terminal 751 is the terminal to which the signal from the emitter terminal of photo transistor 32 used for pulse wave measurement is input via electrode 831. Terminal 755 is the terminal to which the signal for detecting whether or not connector piece 80 is attached to connector 70 is input via electrode 835. Electrode 836 is earthed to the human body at sensor unit 30, so that when terminal 751 and electrode 836 are electrically connected, electrodes 831~834 are shielded as a result of employing VDD as a ground line.

A condenser C1 and switch SW1 are inserted between the terminals (between electrodes 832, 833) of LED 31 used for pulse wave measurement on the connector piece 80 side. Switch SW1, which is closed when connector piece 80 is removed from connector 70, connects condenser C1 in parallel with LED 31 used for pulse wave measurement, and is open when connector piece 80 is attached to connector 70.

Similarly, a condenser C2 and switch SW2 are introduced between the terminals (between electrodes 831,834) of photo transistor 32 used for pulse wave measurement. Switch SW2, which is closed when connector piece 80 is removed from connector 70, connects condenser C2 in parallel with photo transistor 32 used for pulse wave measurement, and is open when connector piece 80 is attached to connector 70.

5.1.6. Structure of the connector piece

Figure 36:
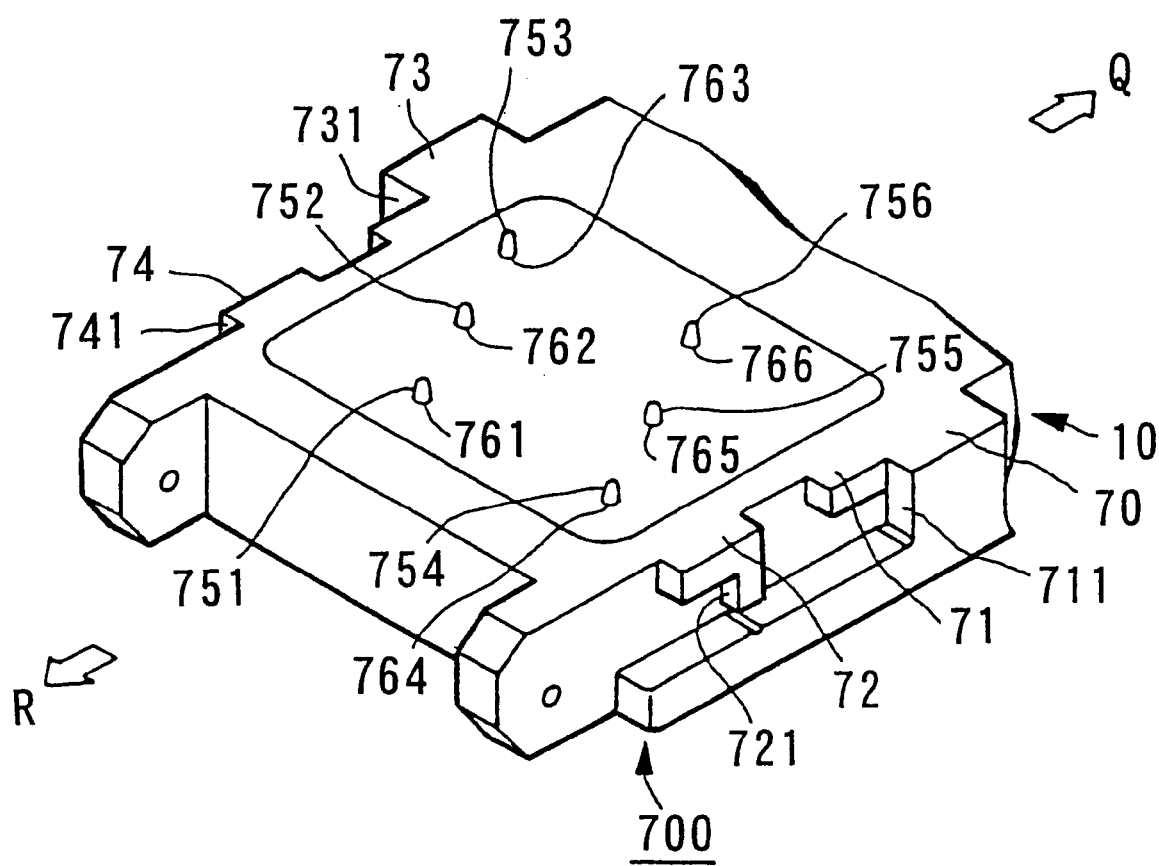
FIG. 36 shows the structure of connector 70 according to this embodiment.

The structure of connector 70 and connector piece 80 will now be explained. FIG. 35 is an enlarged view showing the structure of connector piece 80. FIG. 36 is an enlarged view of connector 70.

A pair of projections 81,82 are formed to either side of the bottom surface 801 of connector piece 80 in FIG. 35, extending in the downward direction. Four interlocking members 811, 812, 821, 822 project inward on the bottom end of projections 81,82. Two operational pins 857,858 are formed to the bottom surface 801, for switching the circuit (explained above) which stops the influence of static electricity when cable 20 is connected to device main body 10. When connector piece 80 is released from connector 70, the end of these operational pins project outward from the bottom surface 801 of connector piece 80.

Six electrodes 831~836 are formed to the bottom surface 801 of connector piece 80. Circular convexities 841~846 are formed about the periphery thereof. As will be explained below, when attaching connector piece 80 to connector 70, connector piece 80 slides in the direction of arrow Q after connector 70 has been covered by connector piece 80. Electrodes 831~836 are formed in two rows of electrodes 831~833 and electrodes 834~836 along the direction of sliding (i.e., the direction indicated by arrow Q). In the case of both of these rows, each of the electrode is disposed on the diagonal, so as to deviate in a direction perpendicular to the direction of sliding of connector piece 80.

5.1.7. Structure of connector

As shown in FIG. 36, interlocking parts 71~74 are formed to connector 70 extending outward. Accordingly, connector piece 80 covers connector 70 so that projections 81,82 of connector piece 80 are positioned to the outside of interlocking parts 71~74 of connector 70, and interlocking members 811,821 of connector piece 80 are positioned between interlocking parts 71 and 72 and between interlocking parts 73 and 74. Next, connector piece 80 is pushed on to connector 70 so that interlocking members 811,821 pass between interlocking parts 71 and 72 and between interlocking parts 73 and 74. (First operation for attaching connector piece 80 to connector 70). Thereafter, connector piece 80 is slid in the direction of arrow Q (i.e., direction of attachment of connector piece 80, from the 6 to the 12 o clock direction on device main body 10). (Second operation for attaching connector 70 to connector piece 80). As a result, the bottom of interlocking parts 71,73 enter into interlocking members 811,821, and interlocking members 821,822 enter into the bottom of interlocking parts 72,74. As a result, interlocking members 811,821,812,822 come to hold interlocking parts 71~74 respectively with the bottom surface 801 of connector piece 80. In this way, connector piece 80 is attached easily and with surety to connector 70.

Similar to electrodes 831~836, terminals 751~756 are formed into two rows of terminals 754~756 and terminals 751~753 along the sliding direction (i.e., direction of arrow Q) of connector piece 80. Further, as in the case of electrodes 831~836, in the case of both rows, each electrode is disposed on the diagonal so as to deviate in a direction perpendicular to the sliding direction of connector piece 80. Accordingly, when connector 70 is attached to connector piece 80, then the six terminals 751~756 are electrically connected to the six electrodes 831~836, so that the results of measurement by sensor unit 30 can be input into device main body 10 via cable 20. Terminals 751~756 are disposed inside holes 761~766 which are formed in connector 70.

When connector piece 80 is removed from connector 70, connector piece 80 slides in the opposite direction as indicated by arrow R. As a result, interlocking members 811,821 return to a position between interlocking parts 71 and 72 and between interlocking parts 73 and 74. Accordingly, if connector piece 80 is raised up in this state, it can be removed with ease and certainty from connector 70.

In this way, an interlocking mechanism 700 is formed which interlocks when connector piece 80 is slid on connector 70 in the direction indicated by Q, and which is released from the interlocked state when the connector piece 80 is slid in the opposite direction (indicated by arrow R). Moreover, although an interlocking mechanism of this design is a small component, the interlocking effect is accomplished with surety.

5.1.8. Structure of stopper mechanism

As shown in FIG. 36, vertical walls 711, 721, 731, and 741 are formed to interlocking parts 71~74, in the direction indicated by arrow Q. Accordingly, when attaching connector piece 80 to connector 70, connector piece slides in the direction of arrow R (second operation), causing interlocking members 811,812,821,822 to come in contact with vertical walls 711,721,731,741, respectively, and stop connector piece 80 at the position of attachment with connector 70. In other words, vertical walls 711,721,731,741 function as first stoppers with respect to connector piece 80.

Conversely, when connector piece 80 is removed from connector 70 by sliding in the direction of arrow R, interlocking members 811,821 come in contact with the rear side of vertical walls 721,741 of interlocking parts 72,74, stopping connector piece 80 and connector 70 at their original positions. In other words, the rear side of vertical walls 721,741 functions as a second stopper with respect to connector piece 80.

5.1.9. Structure of switch mechanism

In FIG. 34, the closing of switch SW1 is linked with the movement of operational pin 858 indicated by the-arrow. Condenser C1 is connected in parallel electrically to LED 31 used for pulse wave measurement. Accordingly, even if the a part having a high voltage due to static electricity comes in contact with electrodes 832,833, the charge is stored in condenser Cl, and does not damage LED 31 used for pulse wave measurement.

In FIG. 34, when connector piece 80 is attached to connector 70, switch SW1 is open, so that a circuit structure capable of measuring the pulse wave is formed. Even if charge is stored in condenser C1, this charge is not released via electrodes 832,833 and terminals 752,753, thus the circuits stored in connector 70 and device main body 10 are not impaired. In this way, the switch mechanism, while having a simple structure, is linked with surety to the attachment operation for attaching connector piece 80 to connector 70.

5.1.10. Structure of connector cover

Figure 37:
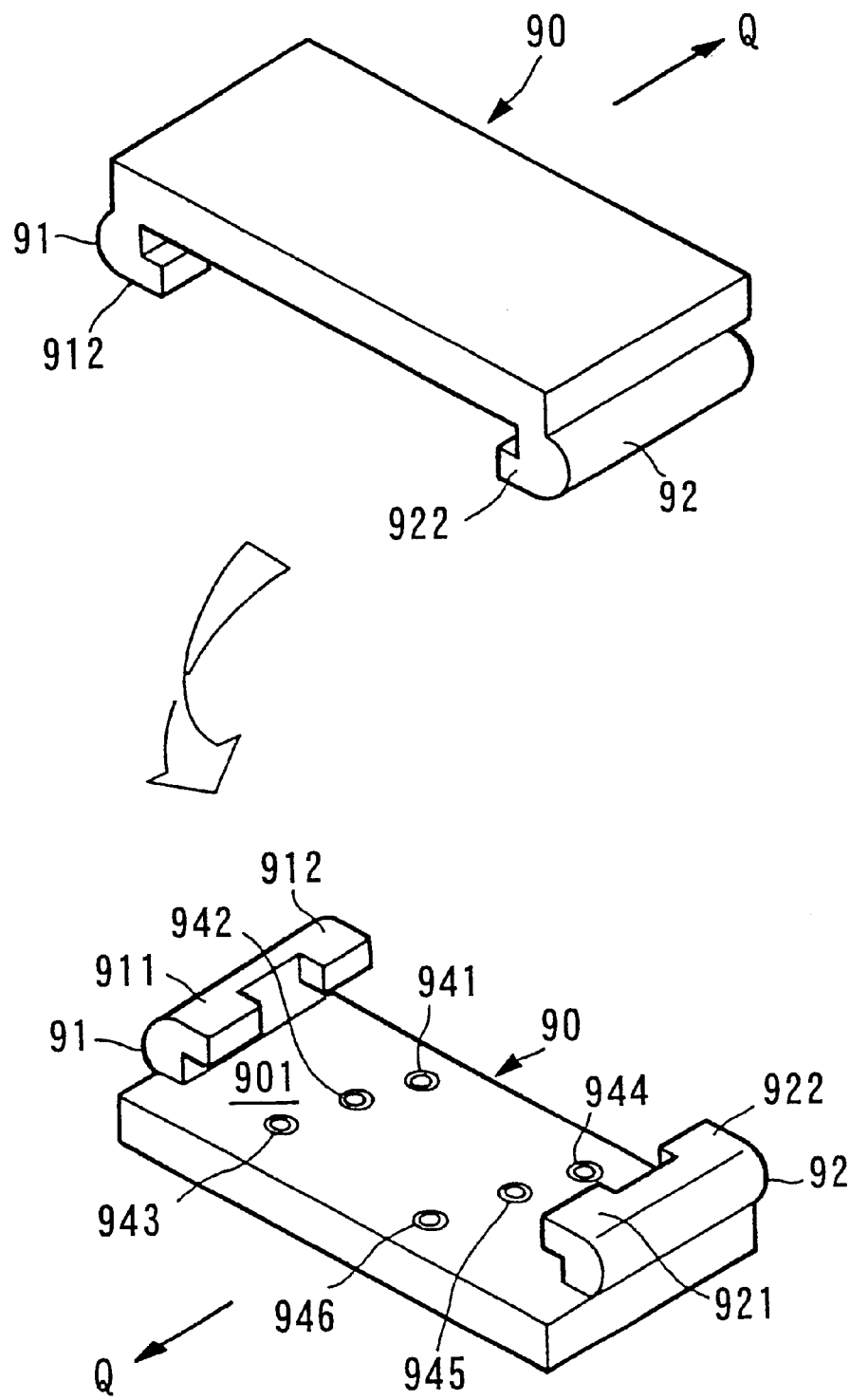
FIG. 37 shows the structure of connector cover 90 according to this embodiment.

FIG. 37 is an explanatory figure showing the structure of connector cover 90. Connector cover 90 is attached to connector 70, when connector piece 80 or communications unit 100 is removed from connector 70 and pulse wave measuring device 1A which attaches to the arm is employed as an ordinary wrist watch. Unlike connector piece 80, connector cover 90 is thin since it does not require electrodes, sensor circuits, or a cable. Further, connector cover 90 is designed in a shape which does not impair appearance when attached to connector 70. However, the structure of attachment with respect to connector 70 is the same as connector piece 80. In other words, a pair of projections 91,92 are formed to the bottom surface 901 of connector cover 90 which extend in the downward direction from either side thereof. Four interlocking members 911, 912,921,922 project inward at the bottom edge of projections 91,92. Convexities 941~946 are formed to the bottom surface 901, corresponding to the positions at which terminals 751~756 of connector 70 are disposed. Convexities 941~946 and terminals 751~756 form a click mechanism.

As in the case of connector piece 80, when attaching connector cover 90 to connector 70, connector cover 90 covers connector 70 so that interlocking members 911,921 of connector cover 90 are positioned between interlocking parts 71 and 72 and between interlocking parts 73 and 74. Then, connector cover 90 is pressed toward connector 70 so that interlocking members 911,921 pass between interlocking parts 71 and 72, and between interlocking parts 73 and 74. Thereafter, when connector cover 90 is slid in the direction indicated by arrow Q (from the 6 o clock to the 12 o clock direction on device main body 10), interlocking members 911,921 enter into the bottom of interlocking parts 71,73, and interlocking members 912,922 enter into the bottom of interlocking parts 72,74. As a result, interlocking parts 71~74 come to be held between interlocking members 911,921,912,922, respectively, and the bottom 901 of connector cover 90. Terminals 751~756 of connector 70 display click strength once they surpass convexities 941~946. In this way, connector cover 90 enters a state of attachment to connector 70.

5.1.11. Structure of the sensor unit

As shown in FIG. 38, the outer view of communications unit 100 is the same as connector piece 80. In other words, as may be understood from a comparison with FIG. 35, communications cable 20 is not attached to communications unit 100, but rather a rectangular visible light cutting filter 1001 covers the middle portion of the upper surface of communications sensor 100. A hole of the approximate shape of filter 1001 is opened directly below filter 1001 for exposing LED 1015 and photo transistor 102. This is designed to send and receive optical signals via filter 1001.

In other words, the internal area of communications unit 100 is a space for housing components. A circuit board not shown is fixed in place so as to oppose filter 1001 on the upper surface. LED 1015, photo transistor 102, and other electronic elements are mounted to this circuit board. LED 1015 and photo transistor 102 use infrared having an intermediate wavelength around 940 nm, with their respective light generating and light receiving surfaces facing toward filter 1001.

Note that the structures of projections 1100,1200, interlocking members 1011,1012,1021,1022, electrodes 1031~1036, convexities 1041~1046, and operational pins 1057,1058 have the same function as projections 81,82, interlocking members 811,812,821,822, electrodes 831~836, convexities 841~846, and operational pins 857, 858 shown in FIG. 35.

5.2. Operation of the Embodiments

Next, the operation of a device according to the preceding structure will be explained. This example will employ the case where the user is running a marathon.

5.2.1. Ordinary wrist watch

When employing pulse wave measuring device 1A which attaches to the arm as an ordinary wrist watch, connector piece 80 of device main body 10 is removed from connector 70, thereby removing cable 20 and sensor unit 30. In this state, device main body 10 is then attached to the arm by means of wrist band 12. Connector cover 90 shown in FIG. 37 is attached to connector 70 at this time, not only improving the appearance of the assembly, but also protecting connector 70.

5.2.2. Operation in pulse wave measuring mode

When using pulse wave measuring device 1A which attaches to the arm to measure the pulse rate while running, connector piece 80 is attached to connector 70 as shown in FIG. 30, and cable 20 is attached to device main body 10. Device main body 10 is then attached to the arm by means of wrist band 12. After tightly attaching sensor unit 30 (glass plate 3041 of optical unit 300 shown in FIG. 32) to the finger by means of band 40 for fixing the sensor in place, the user begins to run.

As shown in FIG. 32, when light is irradiated toward the finger from LED 31 used for pulse wave measurement, this light reaches the capillaries, where a portion of it is absorbed by the hemoglobin in the blood, and a portion is reflected. The light reflected by the capillaries in the finger is received by photo transistor 32 used for pulse wave measurement. The change in the quantity of this received light corresponds to the change in blood volume generated by the pulse waves in the blood. In other words, when blood volume is large, the reflected light becomes weaker, while when the blood volume is little the reflected light becomes stronger. Thus, the pulse wave can be detected by monitoring the change in the intensity of the reflected light at photo transistor 32 used for pulse wave measurement.

On the other hand, data processor 50 shown in FIG. 33 converts the signal input from photo transistor 32 used for pulse wave measurement to a digital signal. The pulse rate is calculated by carrying out frequency analysis and the like on this digital signal, and the obtained pulse rate is then displayed on liquid crystal display 13. In this way, pulse wave measuring device 1A which attaches to the arm functions as a pulse wave measurer. At the same time, the pulse rate and the time at which it was measured are output to data recorder 56 from pulse rate calculator 55, and are stored therein. In addition, when measuring the lap or sprint time during a marathon, this data is also stored in data recorder 56. Further, in the case where a function to measure the temperature or humidity is added to device main body 10, this data is also stored in data recorder 56. Once the marathon is over, the aforementioned information can be sequentially displayed again on liquid crystal display 13.

5.2.3. Operation in data transmission mode

Figure 39:
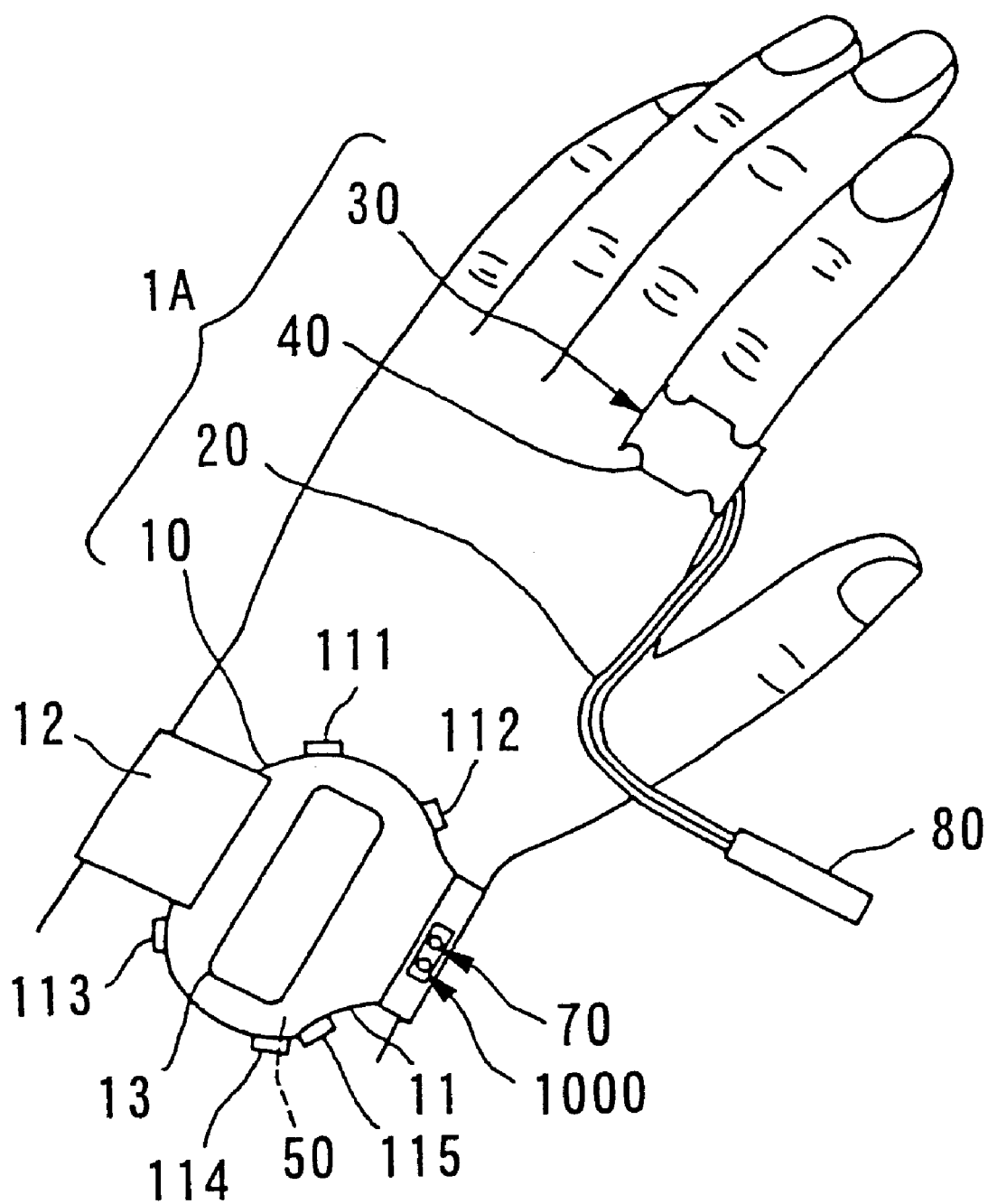
FIG. 39 shows the arrangement for attaching communications unit 100 to connector 70 in place of connector piece 80 in this embodiment.

After employing pulse wave measuring device 1A which attaches to the arm as a pulse wave measurer as described above, then, as shown in FIG. 29, data transmission is carried out between data processor 1B and pulse wave measuring device 1A which attaches to the arm. As shown in FIG. 39, this is accomplished by removing connector piece 80 from connector 70, and attaching communications unit 100 to connector 70. This state is equivalent to the formation of a pair of photo couplers between data processor 1B and pulse wave measuring device 1A which attaches to the arm, so that two-way data transmission is carried out between LED 61 and photo transistor 102, and between LED 1015 and photo transistor 62.

Next, a specific switch from among button switches 111~117 is operated to set pulse wave measuring device 1A which attaches to the arm to the data transmission mode. At this time, data output controller 57 in the data processor 50 shown in FIG. 33 becomes able to output pulse wave information, time data or the like, that has been stored in data recorder 56, as optical signals from LED 1015 of communications unit 100. When a command to transmit data is issued at data processor 1B in this standby state, the optical signal indicating that command is output from LED 61 via communications window 6.

When the optical signal is received by photo transistor 102 in pulse wave measuring device 1A which attaches to the arm, the message signal is received by data input controller 58. As a result, data output controller 57 outputs pulse wave information, time data or the like, that has been stored in data recorder 56, as optical signals from LED 1015. This light signal is received by photo transistor 62 in data processor 1B, with the message signal thereby taken up by data processor 1B. The pulse wave information and time data is recorded in the specified recording medium as needed in data processor 1B, and may be output to a display 3 or printer 5.

Thus, not only is pulse wave information and the like displayed on liquid crystal display 13 of device main body 10 in the pulse wave measuring device 1A according to this embodiment, but, in addition, data is sent to data processor 1B when the user is located away from data processor 1B, by employing data output controller 57 and LED 1015 inside communications unit 100. In other words, at the end of a marathon competition, this data may be displayed all together at data processor 1B, enabling data compilation to be carried out easily.

Moreover, data can be received from data processor 1B by using data input controller 58 and photo transistor 102 inside communications unit 100. Accordingly, it is possible to input conditions for a variety of operations to be carried out at pulse wave measuring device 1A which attaches to the arm, from data processor 1B to pulse wave measuring device 1A which attaches to the arm, and store these conditions in data recorder 56. In this way, setting of these conditions can be carried out from data processor 1B, so that it is not necessary to provide more switches to pulse wave measuring device 1A which attaches to the arm. Moreover, since data transmission using optical communications which employ a releasable communications unit 100 is carried out in order to transmit the aforementioned data, it is not necessary to provide a new interface unit or the like to pulse wave measuring device 1A which attaches to the arm. Thus, pulse wave measuring device 1A which attaches to the arm can be made smaller and more lightweight.

6. Embodiment 6

6.1. Structure of the embodiment

Figure 40:
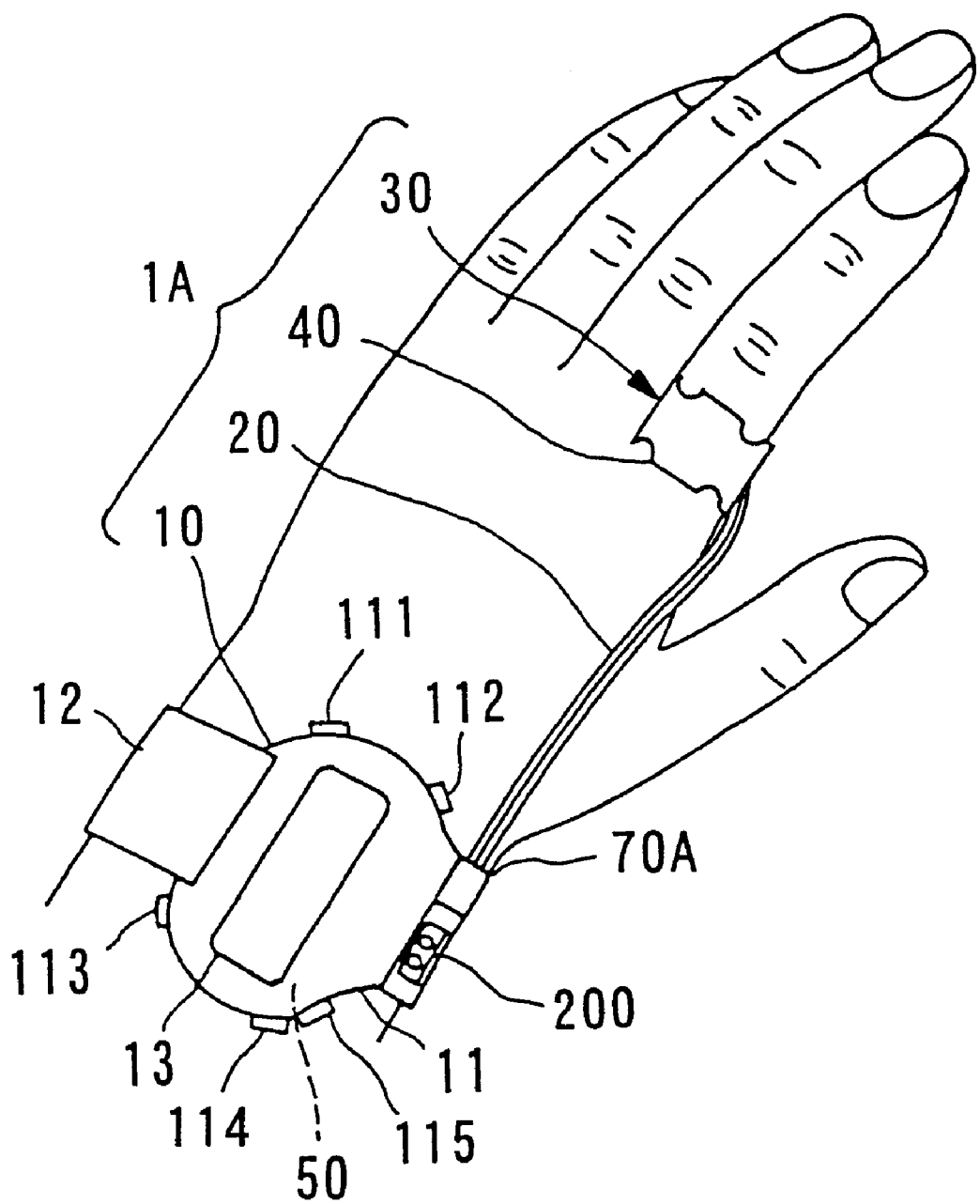
FIG. 40 shows the method of use for a pulse wave measuring device attached to the arm according to the sixth embodiment of the present invention.

When measuring the pulse wave in embodiment 5, a design was provided in which either connector piece 80 or communications unit 100 could be selectively attached to connector 70 of pulse wave measuring device 1A which attaches to the arm. In contrast, in this embodiment, a communications unit 200 in which connector piece 80 and communications unit 100 are formed in a unitary manner is attached to connector 70A of pulse wave measuring device 1A which attaches to the arm, as is shown in FIG. 40.

As a result of this design, there are more electrodes, which connect connector 70A and communications unit 200, employed in this embodiment than in embodiment 5.

Namely, the structure of communications unit 200 is as indicated by the blown-up view shown in FIG. 41. A filter 1001 is provided to the upper surface of communications unit 200, and a cable 20 is connected. When compared to the communications unit 100 shown in FIG. 38, electrodes 1137~1140 and circular convexities 1147~1150 are formed to the bottom surface 1301 of communications unit 200. These electrodes are in pairs, and are disposed in parallel respectively with respect to the two rows of electrodes present in FIG. 38. Note that this is also the case for the convexities.

Note that the structures of projections 1300,1400, interlocking members 1111,1112,1121,1122, electrodes 1131~1136, convexities 1141~1146, and operational pins 1157,1158 have the same function as projections 1100,1200, interlocking members 1011,1012,1021,1022, electrodes 1031~1036, convexities 1041~1046, and operational pins 1057,1058 shown in FIG. 38.

Figure 42:
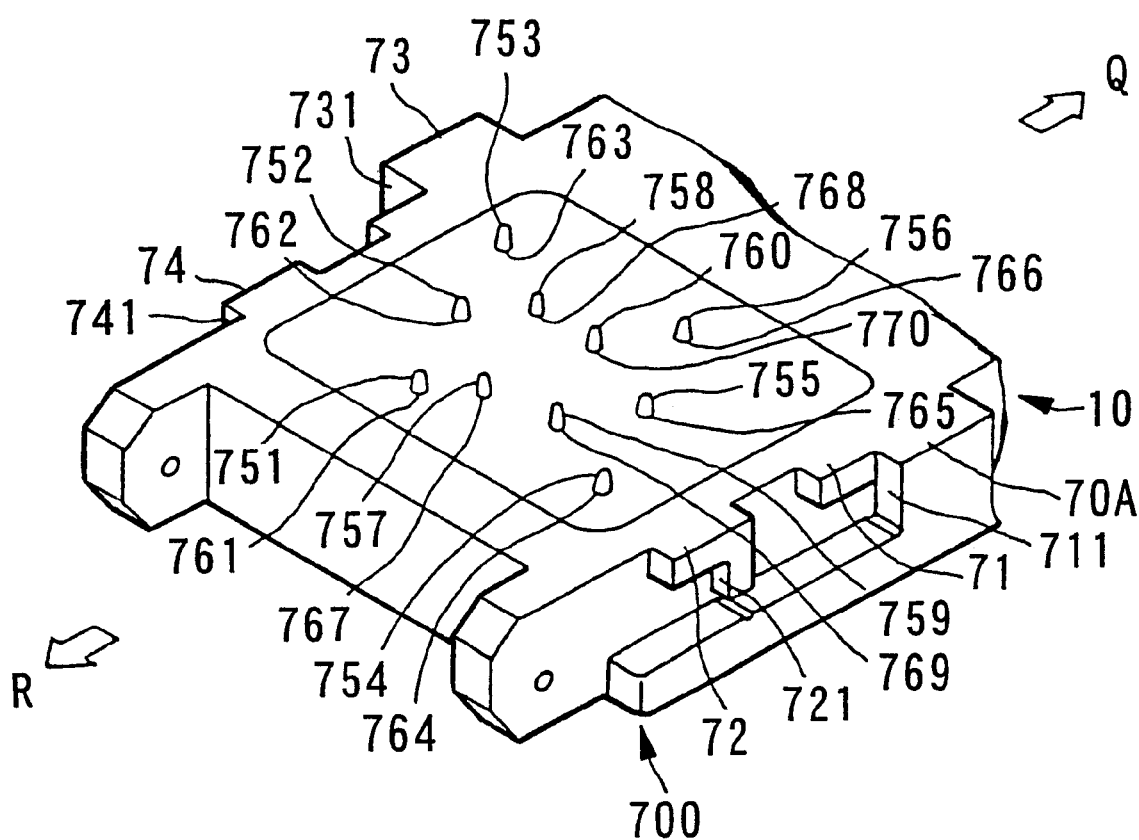
FIG. 42 shows the structure of connector 70A according to this same embodiment.

With respect to connector 70 shown in FIG. 36, connector 70A shown in FIG. 42 additionally has terminals 757~760 and holes 767~770 formed in the upper surface thereof. These terminals are in pairs, and are disposed in parallel respectively with respect to the two rows of terminals present in FIG. 36. The same holds true for the holes.

Figure 43:
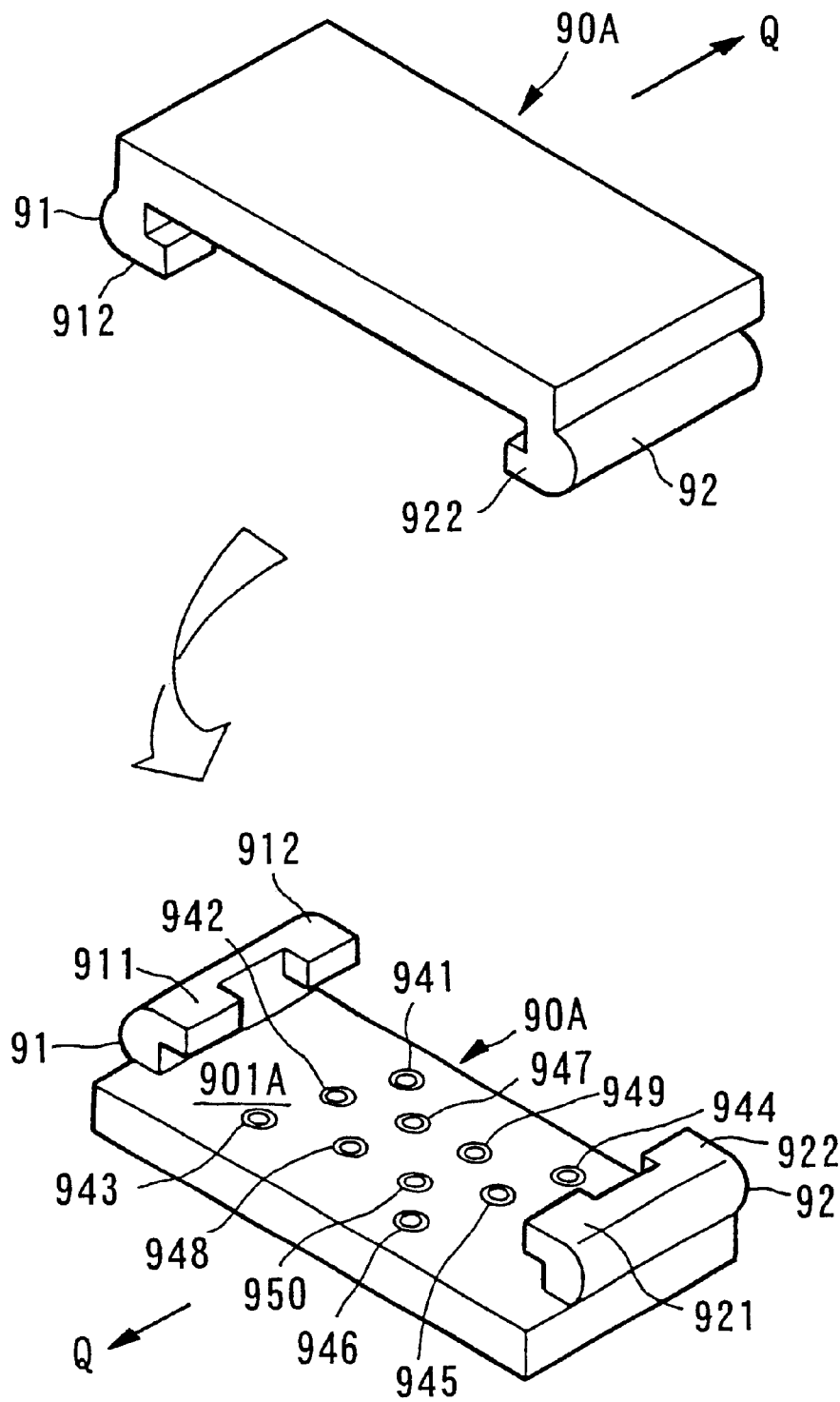
FIG. 43 shows the structure of connector cover 90A according to this same embodiment.

With respect to the connector cover 90 shown in FIG. 37, connector cover 90A shown in FIG. 43 additionally has convexities 947~950 formed in the lower surface 901A thereof. These convexities are in pairs, and are disposed in parallel respectively with respect to the two row of convexities present in FIG. 37.

Further, while not shown in the figures, circuits equivalent to those provided to LED 31 and photo transistor 32 respectively in FIG. 34 are added with respect to LED 1015 and photo transistor 102.

6.2. Operation of the embodiment

The operation of this embodiment will now be explained.

6.2.1. Ordinary wrist watch

In this case, band 40 for fixing the sensor in place is removed from the finger, thereby also removing sensor unit 30, and connector cover 90A is attached to connector 70A.

6.2.2. Operation in pulse wave measuring mode

When measuring the pulse rate during running, connector cover 90A is removed from connector 70A and sensor unit 200 is attached to connector 70A in its place. The user then begins running. After the pulse wave signal detected by sensor unit 30 has been taken up by data processor 50 and converted to a digital signal in the same manner as in Embodiment 5, the pulse rate is calculated by carrying out frequency analysis and the like on the digital signal, and the obtained pulse rate is then displayed on liquid crystal display 13. In addition, the time at which the pulse rate was measured is also stored together with the pulse rate in data recorder 56.

6.2.3. Operation in data transmission mode

When carrying out data transmission between data processor 1B and pulse wave measuring device 1A which attaches to the arm, a specific button switch is operated to put pulse wave measuring device 1A which attaches to the arm in the data transmission mode. Next, as in the fifth embodiment, data output controller 57 sends information stored in data recorder 56 to data processor 1B by means of optical signals, and carries out recording of the information in the recording media, output to display 3 or printer 5, and the like.

As a result, in this embodiment, once sensor unit 30 and communications unit 200 have been attached, it becomes possible to measure the pulse wave, send the pulse wave signal from sensor unit 30 to device main body 10, and send pulse information and the like from device main body 10 to data processor 1B, and the like, without performing any connection or release operations with connector 70A thereafter. Accordingly, the burden on the user is substantially reduced.

7. Embodiment 7

7.1. Structure of the embodiment

Figure 44:
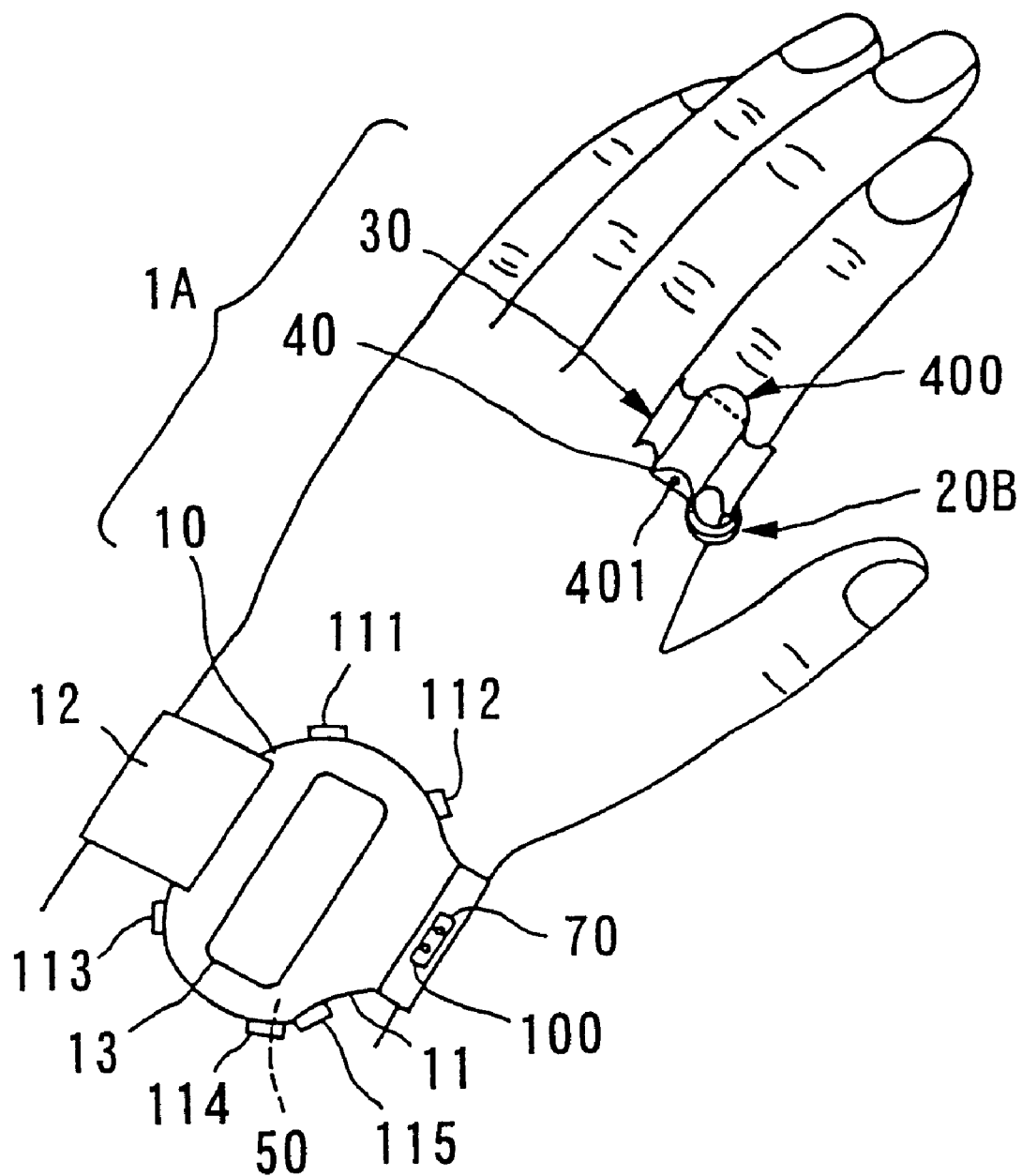
FIG. 44 shows the method of use for the pulse wave measuring device attached to the arm according to the seventh embodiment of the present invention.

In this embodiment, transmission of pulse wave information from sensor unit 30 to device main body 10 is carried out by means of optical signals, as shown in FIG. 44. In other words, a semispherical transmission device 400 is fixed in place along the longitudinal direction of the upper surface of band 40 for fixing the sensor in place which forms sensor unit 30. Further, sensor unit 30 and transmission device 400 send and-receive the pulse signal by means of an electrical connection via cable 20B. The electric source is supplied from transmission device 400 to sensor unit 30. A hole is provided on the bracket side of transmission device 400. Infrared LED 401, which is an element used for optical communications, is exposed via this hole.

In this embodiment, either connector cover 90 or communications unit 100 is attached to connector 70.

Figure 45:
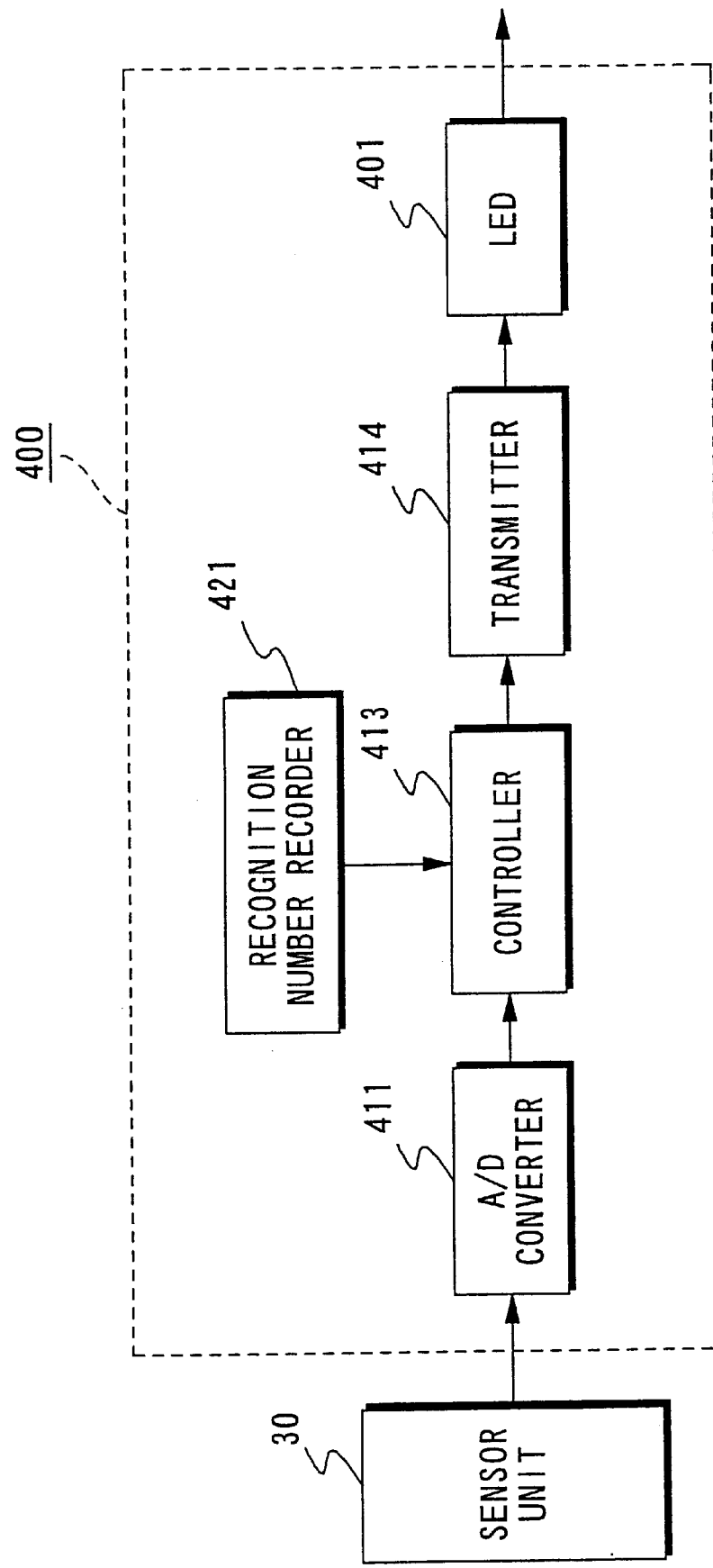
FIG. 45 is a block diagram showing the structure of transmission device 400 according to this same embodiment.

Next, the block diagram in FIG. 45 will be used to explain the circuit structure of transmission device 400. In this figure, A/D (analog/digit) converter 411 samples at specific time intervals the pulse wave signals sent from sensor unit 30, and converts the signal to a digital signal.

Recognition number recorder 412 records recognition numbers for recognizing which device sent the optical signal. When the pulse signal is sent from transmission device 400 to the outside, this recognition number is imparted to the optical signal along with the pulse wave signal. This is done to prevent competition when there are a plurality of transmission devices 400 because there are a plurality of individuals using pulse wave measuring device 1A which attaches to the arm. Accordingly, the recognition numbers recorded in recognition number recorder 412 inside each transmission device is assigned a differed number when setting is performed at the time of shipping. Thus, in this embodiment, unique numbers are assigned to all of the devices in this embodiment, including device main body 10 (i.e., data processor 50) and data processor 1B.

Controller 413 is a circuit for controlling each of the parts inside transmission device 400. In addition, transmitter 414 houses a drive circuit for driving LED 401. By driving LED 401, the transmission data formed by controller 413 is converted to an optical signal and sent to the outside.

A battery (not shown) which is the electric source for sensor unit 30 and each of the parts inside transmission device 400 is loaded inside transmission device 400.

7.2. Operation of the embodiment

The operation of the embodiment will now be explained.

7.2.1. Ordinary wrist watch

In this case, band 40 for fixing the sensor in place is removed from the finger, thereby also removing sensor unit 30 and transmission device 400, and connector cover 90 is attached to connector 70.

7.2.2. Operation in pulse wave measuring mode

When measuring the pulse rate during running, sensor unit 30 and transmission device 400 are attached to the finger by means of band 40 for fixing the sensor in place, so that the light emitter of LED 401 is directed toward the elbow side (device main body 10 side), as shown in FIG. 44. Connector cover 90 is removed from connector 70 of pulse wave measuring device 1A which attaches to the arm, and communications unit 100 is attached in its place. The user then begins to run.

The pulse wave signal detected by sensor unit 30 is taken up by controller 413 after being converted to a digital signal by A/D converter 411. Controller 413 applies information from recognition number recorder 412 such as a recognition number to the digitized signal which has been taken up, and sends the signal to transmitter 414. This information is converted to an optical signal at transmitter 414, and sent from LED 401 outside transmission device 400. This optical signal is sent to data processor 50 via photo transistor 102 of communications connector 1000. As a result, data input controller 58 extracts the recognition number portion from the optical signal and stores it in data recorder 56. The transmission source of the optical signal is recognized to be transmission device 400 provided to pulse wave measuring device 1A which attaches to the arm, and subsequent data is recognized as pulse wave signals. Thereafter, in the same manner as in Embodiment 5, the pulse signal is taken up and the pulse rate is calculated and displayed on liquid crystal display 13. The pulse rate and the time at which it was measured are stored together in data recorder 56.

7.2.3. Operation in data transmission mode

When carrying out data transmission between data processor 1B and pulse wave measuring device 1A which attaches to the arm, a specific button switch is operated to put pulse wave measuring device 1A which attaches to the arm in the data transmission mode. Next, as in the fifth embodiment, data output controller 57 sends information stored in data recorder 56 to data processor 1B by means of optical signals, and carries out recording of the information in the recording media, output to display 3 or printer 5, and the like.

As a result, in this embodiment, once communications connector 1000, sensor unit 30 and transmission device 400 have been attached, it becomes possible to measure the pulse wave, send the pulse wave signal from sensor unit 30 to device main body 10, and send pulse information and the like from device main body 10 to data processor 1B, and the like, without performing any connection or release operations with connector 70 thereafter. Accordingly, the burden on the user is substantially reduced.

8. Embodiment 8

The user s $VO_{2max}$ was obtained in the preceding first through third embodiments, and the user was notified of an exercise workout based on the obtained $VO_{2max}$. The details of this will be explained below. First, in order to notify the user of the exercise workout, it is necessary to specify the user s optimal exercise intensity, exercise duration per session, and frequency of exercise during a given period of time.

As discussed above, the optimal exercise intensity is the exercise intensity corresponding to 50% of $VO_{2max}$. Thus, this value can be directly determined once $VO_{2max}$ is obtained. Further, if the typical person is taken as the subject, then a suitable duration of exercise per session is 20 min, while a suitable exercise frequency is 40~50%, (i.e., 4 to 5 days out of a 10-day period).

Figures 50, 51:
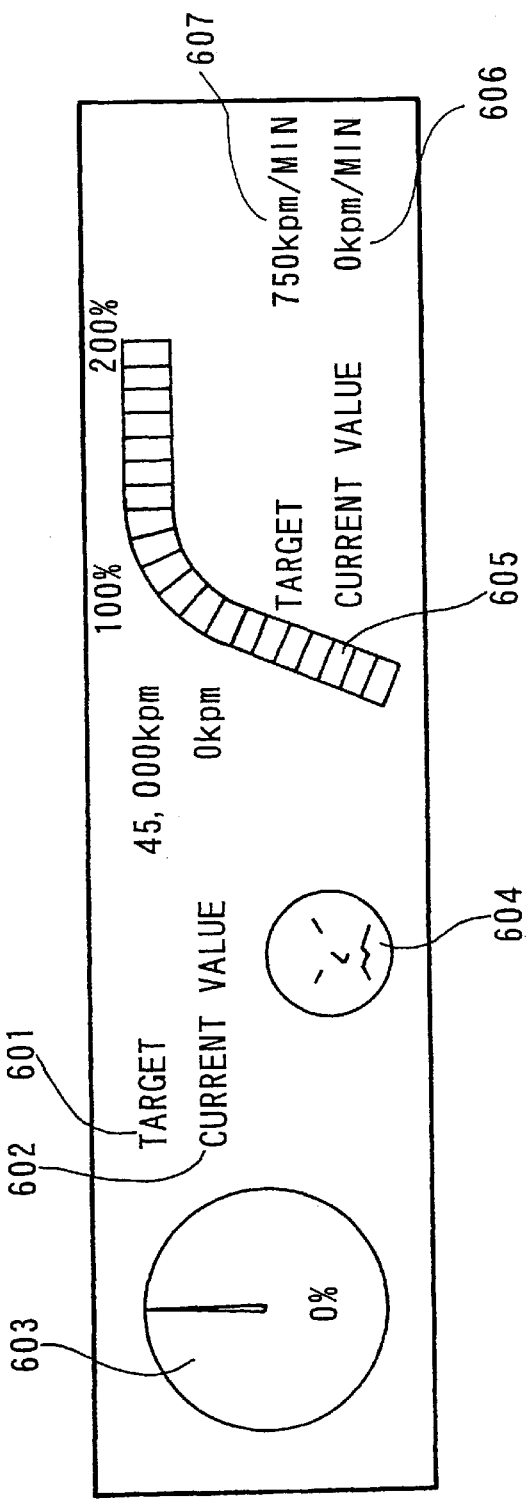
FIGS. 50 through 53 show examples of displays for display 208 in the eighth embodiment of the present invention.

Accordingly, in this modification, once the $VO_{2max}$ has been obtained, then an exercise target screen such as shown in FIG. 50 is displayed on display 208. From the example in this figure, it may be understood that exercise of 750 kpm/min, 3 times a week for 20 minutes at a time, is suitable. Here, the screen shown in FIG. 51 is displayed in display 208 when the user performs a specific manipulation.

In the figure, 601 is an exercise quantity target value display which displays a target value for the user with respect to the exercise quantity per week. From the preceding example, the exercise quantity target value would be [750[kpm/min]×20[min]×3[times]=45000[kpm]]. Accordingly, this value is displayed on the display. Note that exercise quantity is obtained by taking the integral of exercise intensity with respect to time. 602 indicates an exercise quantity current value display which displays the cumulative value for the quantity of exercise performed by the user over the past week. However, the example shown in the figure assumes the state immediately after the user has initiated the device according to this embodiment for the first time, and obtained the $VO_{2max}$. Therefore, a [0] is displayed on exercise quantity current value display 602.

Next, 603 indicates a bar graph display which displays the exercise quantity current value with respect to the exercise quantity target value as a percentage proportion thereof. 604 is a face chart display which displays a face chart in accordance with the exercise quantity current value-to-exercise quantity target value proportion. 607 is an exercise intensity target value display which displays the exercise intensity target value (750[kpm/min]) obtained previously. 606 is an exercise intensity current value display which displays the current value of exercise intensity. The example shown in this figure assumes that the user has stopped, so that exercise intensity current value display 606 displays a [0].

Next, 605 is an exercise intensity meter wherein there are disposed 20 LEDs at intervals of 10% within the range of [0%]~[200%]. By means of the illumination of these LEDs, the proportion of the exercise intensity current value with respect to the exercise intensity target value is displayed. In the example shown in this figure, the exercise intensity current value is [0], so that none of the LEDs are illuminated. From among the LEDs which compose exercise intensity meter 605, those corresponding to [10~70%] are yellow, those corresponding to [80~120%] are blue, and those corresponding to [130% or higher] are red.

Figure 52:
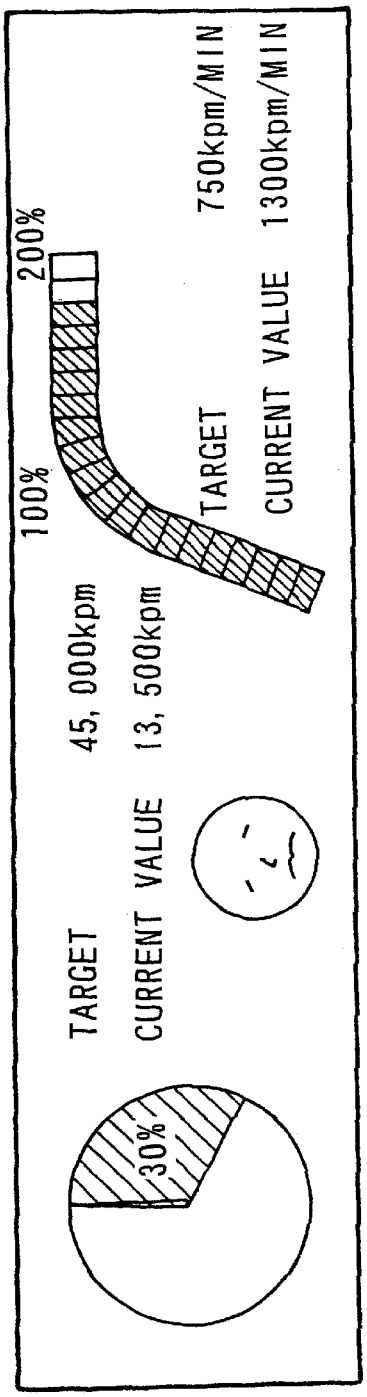

Next, an example of the display in the state where the user is carrying out exercise of a given degree is shown in FIG. 52. The exercise quantity current value in the example shown in the figure is [13500], so that [30%] of the exercise quantity target value has been reached. Accordingly, a pie chart corresponding to this is displayed on pie chart display 603, and a face chart displayed on face chart display 604 is changed in accordance to the proportion of the target value which has been achieved.

On the other hand, the exercise intensity current value is [1300], which greatly exceeds the exercise intensity target value of [750]. Accordingly, a number of red LEDs from among those provided to exercise intensity meter 605 are illuminated. Accordingly, the user is able to know that the intensity of exercise is too great by looking at the display.

Figure 53:
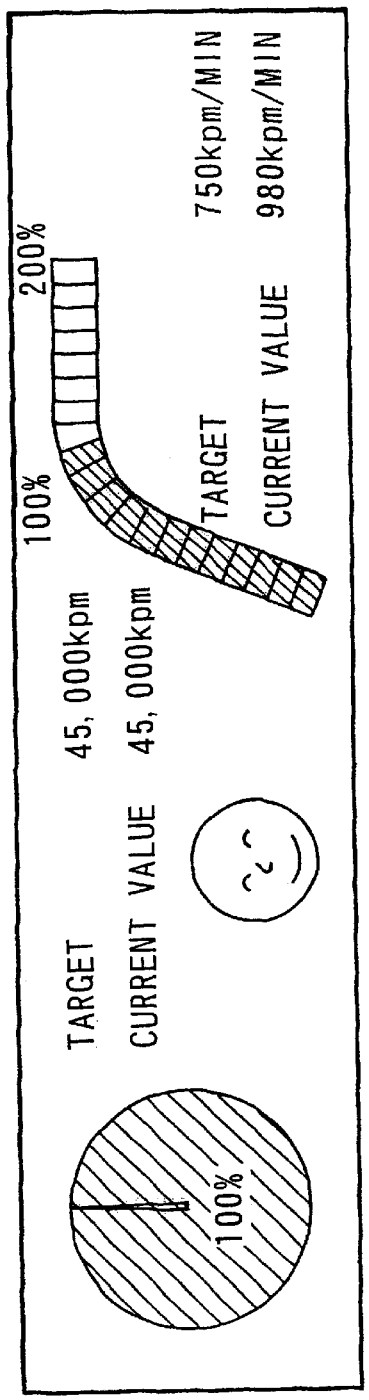

Next, the suitable state for the user s exercise quantity and exercise intensity is shown in FIG. 53. In this figure, the exercise quantity current value is [45000[kpm]], so that the exercise quantity target value has been reached. Accordingly, the displays on the pie chart display 603 and the face chart display 604 correspond to this state. Further, the exercise intensity current value is [980[kpm/min]], which is within ±20% of the exercise intensity target value. Thus, the corresponding green LEDs in exercise intensity meter 605 are illuminated.

In this modification, the exercise quantity is recorded each day, extending over the past 7 days, and this cumulative result is displayed as the exercise quantity current value. Further, at a specific time (for example, 12 midnight), the data for exercise quantity from the oldest day is discarded, and the exercise quantity data from the new day is used in place thereof.

The above example employed a 7 day period for the interval over which the exercise quantity data is added up. However, this interval could also be 10 days or the like, for example. In other words, the user is free to set this interval. Accordingly, the user may set a specific target date such as [3 months], and then be able to carry out training by setting an exercise quantity targeted for that interval.

In addition, by providing a connector 70 such as explained in the fifth embodiment to the device of the present embodiment, and attaching communications unit 100 thereto, it is possible to carry out two-way data transmission with an external device. Namely, the $VO_{2max}$ or pulse wave data measured by the device according to the present embodiment can be supplied to an external device. Moreover, in the device according to the present embodiment, it is possible to provide an exercise workout which is influenced not only by the value measured for $VO_{2max}$, but also by the various data obtained from the external device (the results of consultation with a physician or trainer, for example).

9. Modifications

In the preceding, the present invention was explained in detail with reference to the figures. However, the specific structure of the present invention is not limited to these embodiments. Rather, a variety of modifications such as changing the design within limits which do not depart from the spirit of the invention are included within the scope of the present invention, various examples being provided below.

9.1. Modification of device arrangement

The site of detection of the pulse wave is not limited to the finger. Rather, any site (the ear, for example) is acceptable, provided that the pulse wave can be measured there.

In other words, although the arrangement of the device according to each of the preceding embodiments was typically in the form of a wrist watch, the present invention is not limited thereto. Any object used by the test subject daily, or an object worn on the body (i.e., portable object), is also acceptable. For example, the device may be incorporated into eyeglasses, a ring, necklace, band, or the like, or may be incorporated as one function of a pedometer that is attached via a band.

A pair of eyeglasses and an accessory will now be used as examples of items into which the device of the present invention may be incorporated, in addition to a wristwatch.

Figure 46:
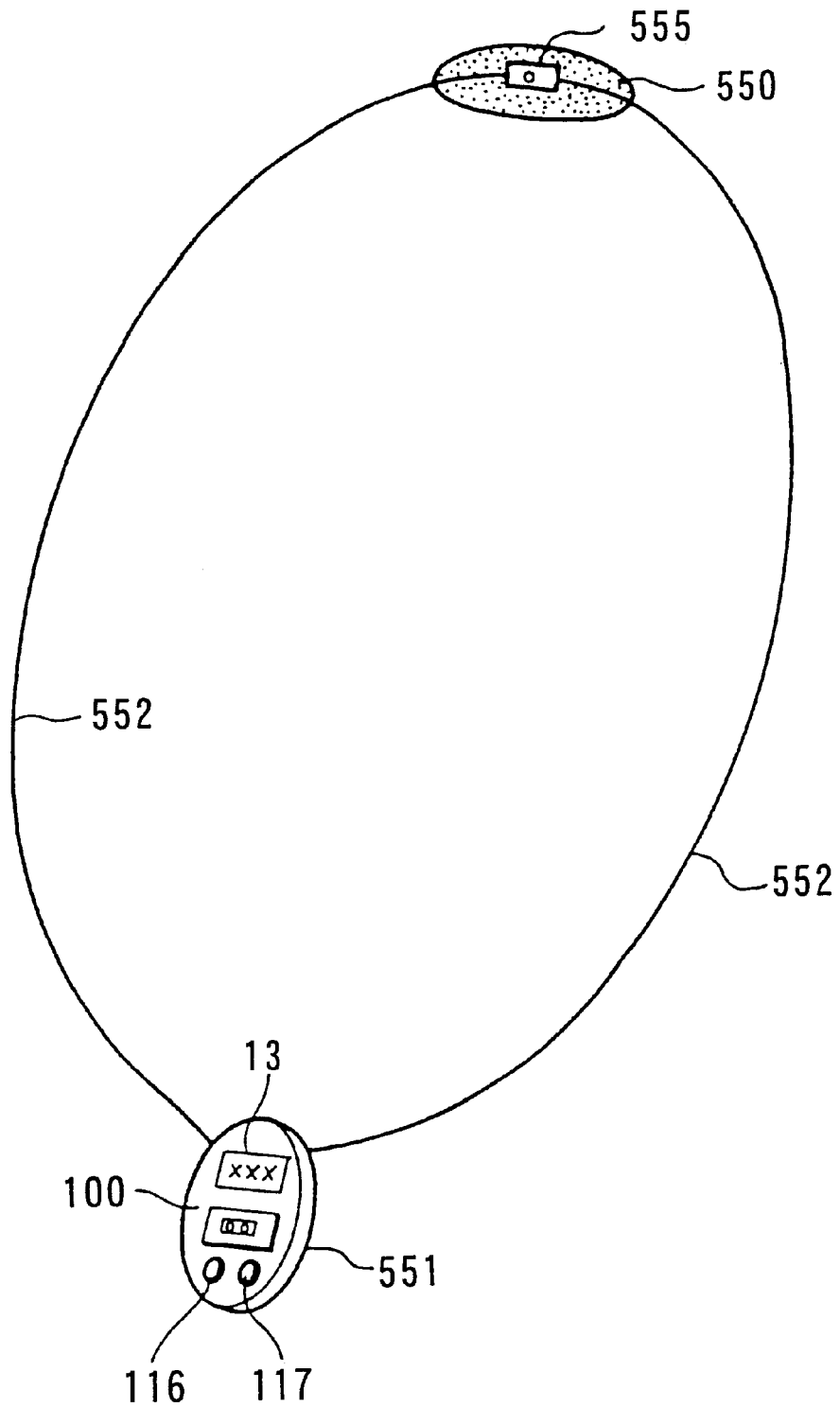
FIG. 46 shows the case where the device is incorporated into a necklace.

The necklace shown in FIG. 46 may be cited as an example of an accessory into which the device of the present invention may be incorporated. In this figure, 550 is a sensor pad, and is comprised, for example, of a shock absorbing material such as a sponge. A transmission device 555 formed in the same manner as transmission device 400 shown in FIG. 44 is attached to sensor pad 550. A sensor unit (not shown) which corresponds to optical unit 300 is provided to transmission device 555. This sensor unit is formed so as to be in contact with the skin surface. As a result, when this necklace is worn around the neck, the sensor unit comes in contact with the skin at the back of the neck, enabling measurement of the pulse wave.

A variety of parts equivalent to those provided inside device main body 10 in the first embodiment are housed in case 551 which is in the form of a broach which is hollow. A connector is provided to case 551 for attaching either connector cover 90 or communications unit 100 to the front surface thereof. Communications unit 100 is shown attached in the figure.

Button switches are provided to case 551. Button switches 116, 117 from among the button switches shown in FIG. 31 are indicated here. However, other button switches may also be provided. Further, liquid crystal display device 13 is provided to the front surface of case 551. In addition, as shown in the figure, sensor pad 550 and case 551 are linked via chain 552.

Note that it is of course acceptable to employ other types of accessories, in addition to a necklace.

Figure 47:
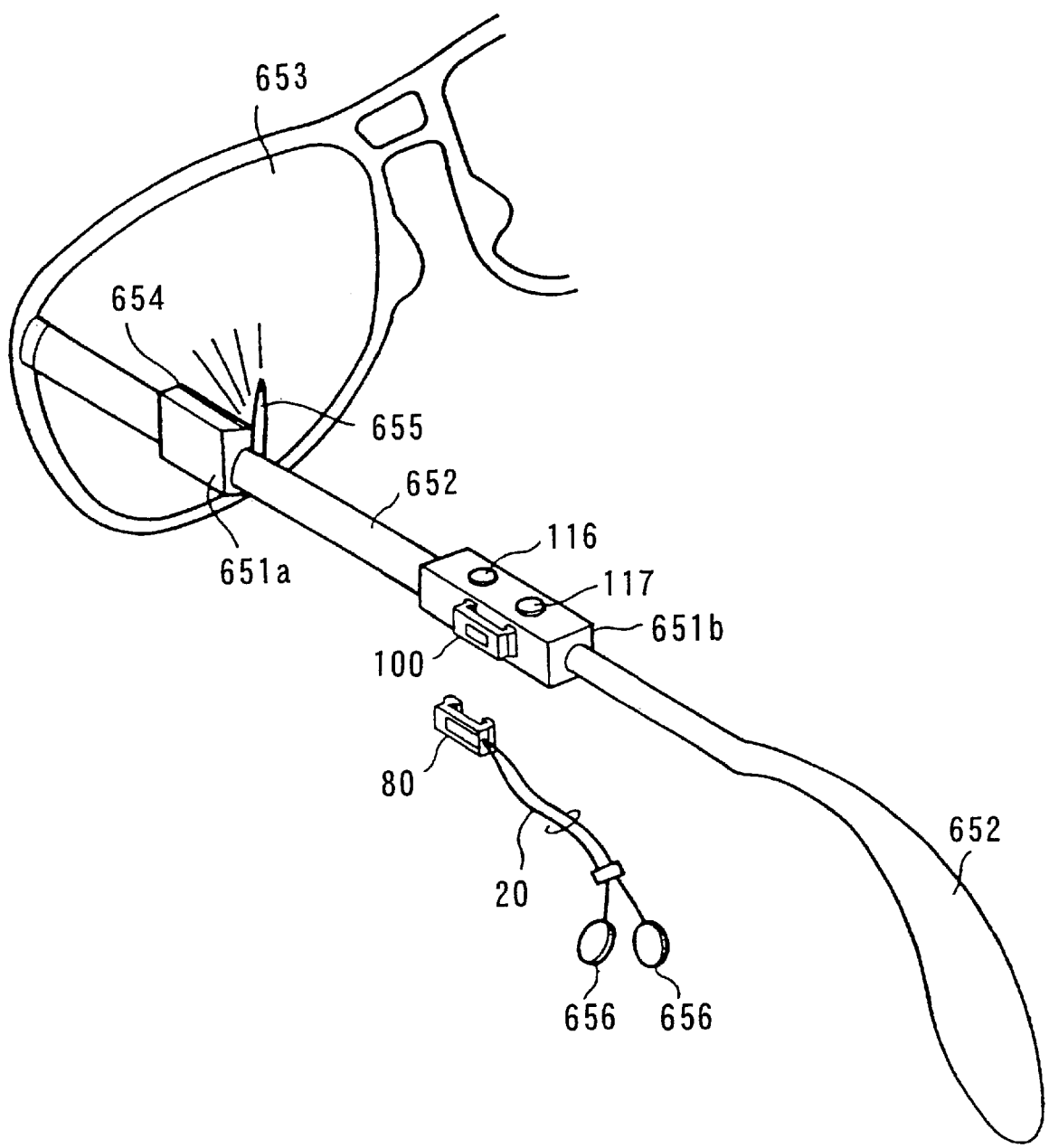
FIG. 47 shows the case where the device is incorporated into a pair of eye glasses.

FIG. 47 shows an example of the case where the present invention is incorporated into a pair of eyeglasses. As shown in this figure, a case 651a and a case 651b are provided for housing the portable pulse wave measuring device. These cases are attached to the stems 652 of the eyeglasses, respectively, and are connected electrically via a lead wire embedded in stems 652.

Case 651a houses a display control circuit. A liquid crystal panel 654 is attached over the entire surface of the lens 653 side of case 651a. A mirror 655 is fixed to the edge of this lateral surface at a specific angle. A drive circuit for liquid crystal panel 654 which includes a light source (not shown) is incorporated in case 651a. The light emitted from this light source passes via liquid crystal panel 654, and is reflected at mirror 655 to incident on lens 653 of the eyeglasses. Accordingly, this corresponds to liquid crystal display 13 in FIG. 33.

Components equivalent to those housed inside device main body 10 of the first embodiment are included in case 651b. A variety of button switches are provided to the upper surface thereof. As in the case of the necklace, only button switches 116,117 are shown, however, other button switches may be provided. In addition, a connector is provided to the lateral surface opposite that which contacts the skin, for attaching either connector piece 80, connector cover 90, or communications unit 100. Communications unit 100 is shown attached in the figure.

Photo transistor 32 and LED 31 which formed optical unit 300 in the first embodiment are housed inside pads 656, with the subject s earlobe being held between pads 656,656. In addition, these pads are connected to connector piece 80 via cable 20.

The lead wires which connect case 651a and case 651b may be designed so as to extend along stems 652, or may be formed in a unitary manner with the two cases described above. The mirror may be moveable so that the user can adjust the angle between the liquid crystal panel 654 and mirror 655. Further, while FIG. 47 shows the situation described in connection with the first embodiment, it is also acceptable to combine this with the second through third embodiments.

The above-described embodiments may be combined in various ways. For example, transmission device 555 shown in FIG. 46 may be employed in place of transmission device 400 shown in FIG. 44, to send the pulse wave signal measured at the neck to the wrist watch side by means of an optical signal. Similarly, it is acceptable to provide a design in which only a transmission device is provided to the eyeglasses shown in FIG. 47, with the pulse wave signal measured at the earlobe sent to the wrist watch side, and transmission to the data processor 1B side then carried out via the wrist watch.

The preceding explanations employed a design in which the connector piece or communications unit was attached in a releasable manner to a portable device such as a wrist watch, necklace, pair of eyeglasses or the like. However, when the pulse wave is not being measured, the connector piece or communications unit may be left attached to the portable device without any problem. Accordingly, provided that the design is not one in which the connector piece and the communications unit are alternatively attached to the connector, i.e., provided that the design is one other th an that of the first embodiment, then the communications unit may be attached by fixing it in place on the portable device side. As a result, it is possible to eliminate connector 70 from the portable device, so that the structure of the portable device can be simplified and the production cost reduced.

9.2. Modification of the type of exercise

The exercise performed by the test subject in the preceding first through third embodiments was running. However, the present invention is not limited thereto. For example, the same effect may be obtained in the case where the exercise is swimming. In this case, the distance covered with each stroke is input corresponding to the running stride, and the number of strokes per unit time is detected corresponding to pitch. In other words, provided that the test subject s exercise intensity and beat number can be detected, then the form of exercise is not restricted, and the maximum oxygen uptake quantity ($VO_{2max}$/wt) can be obtained.

To restate, the acceleration sensor employed as body motion sensor 302 is not limited to the arm, but may be attached anywhere on the body of the runner, thereby enabling the pitch to be measured from the change in acceleration.

9.3. Modification of the recording device

Further, in each of the preceding embodiments, the pulse rate table recorder 9 was composed of ROM. However, in addition, it is also possible to employ a non-volatile memory ($E^2$PROM, flash ROM, battery backed-up RAM, etc.) which is write-capable for pulse rate recorder 9. In this case, the contents of the pulse rate table shown in FIG. 14 are occasionally written over in response to improvement in the user s exercise capacity.

9.4. Modification of the estimate and input of $VO_{2max}$

With respect to the methods for estimating $VO_{2max}$, in addition to the above-described indirect method, other methods may be considered such as a method in which the components in the air expired by the subject are measured, or a method in which $VO_{2max}$ is obtained from the lactic acid threshold value.

The expired gas method cited here is a method for estimating $VO_{2max}$/wt from the $CO_2$ present in expired air and the power under maximum effort exercise, while the lactic acid threshold method estimates $VO_{2max}$/wt from the power under maximum effort exercise and lactic acid in the blood.

In addition to a method using up switch U and down switch D, other methods are available for inputting $VO_{2max}$, including the method of providing a small ten-key, or a method in which input of $VO_{2max}$ is carried out by communication from a personal computer or other device (either wireless or wired).

Further, the pulse rate read out from the pulse rate table may be corrected for the user s age, the surrounding temperature obtained from a temperature sensor (not shown), or for the desired exercise intensity which matches the subject s current physical condition.

In addition, the width between upper limit UL and lower limit LL may be a value other than ±20%.

Moreover, with respect to the frequency analysis method carried out by CPU 308, other methods may be considered in addition to FFT, including the maximum entropy method, the wavelet conversion method, and the like.

9.5. Modification of method for notifying user 9.5.1. Notification using sense of sight, touch, etc. With respect to the method of pitch notification of the user in the fourth embodiment, methods relying on the sense of sight or touch may also be employed, in addition to the pitch sound from sound releaser 25. For example, in the case of the sense of sight, an LED or the like may be flashed in time with the indicated pitch. In the case of the tactile sense, a form memory alloy may be provided projecting outward from the bottom surface of a main body 14 (see FIG. 16), with electricity passed through this form memory alloy at a timing which matches the indicated pitch. Alternatively, a vibration alarm is conventionally known which communicates a vibration to the user s body by rotation of an eccentric load. This vibration alarm may be provided separately or in a unitary manner with main body 14, with electricity passed through the vibration alarm in time with the indicated pitch.

Figure 28:
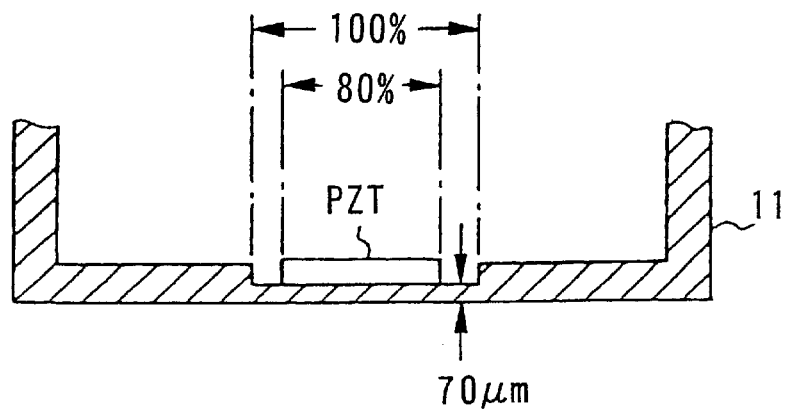
FIG. 28 is a cross-sectional view showing the state of installation when a piezo element is employed as the pitch notifying means.

In addition, a concavity may be formed in a portion of the inner side of the bottom surface of the main body 14 having a thickness of 70 μm as shown in FIG. 28. A piezoelement PZT is then attached to this concavity. When an alternating current of a suitable frequency is impressed on this piezoelement, piezoelement PZT vibrates, with this vibration communicated to the user. Accordingly, if an alternating current is impressed at a timing matching the indicated pitch, then it is possible to provide tactile pitch notification. Additionally, piezoelement PZT may have a thickness of 100 μm, with a diameter length which is 80% of the length of the diameter of the concavity.

9.5.2. Notification of results of pitch evaluation

Figure 48:
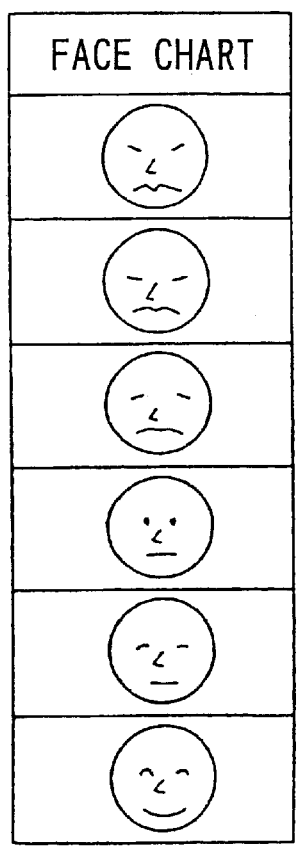
FIG. 48 shows an example of a modification for the pitch notifying arrangement.

The user may be notified of the results of an evaluation of the current pitch, i.e., whether it is in the appropriate range, is too low or is too high, rather than simply being notified of the pitch. Provided that the arrangement for notification of the results of this evaluation rely on sight, sound, touch or one of the other five senses, then any embodiment may be appropriately employed. For example, a face chart such as shown in FIG. 48 may be used to indicate whether or not the results of the evaluation are in the appropriate range.

Figure 49:
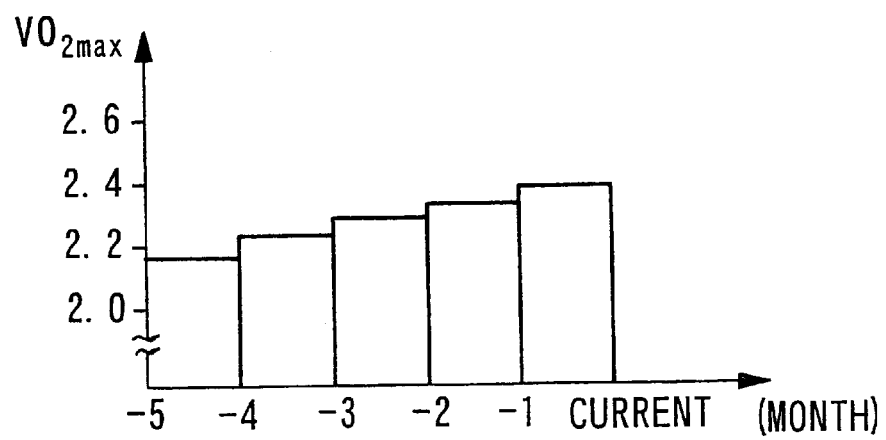
FIG. 49 shows the arrangement wherein the user is notified of the change in $VO_{2max}$ over an extended period of time.

9.5.3. Notification of $VO_{2max}$ history $VO_{2max}$ is a measure of the increase in endurance. Therefore, in each of the preceding embodiments, the $VO_{2max}$ history extending over a long period of time is recorded in memory, and the user is notified by displaying the change on display 208. FIG. 49 shows an example in which the change in $VO_{2max}$ is displayed in one month units. In this figure, the average value for one month periods extending back four to six months from the current time is displayed in the form of a histogram. As a result, the user is able to know the effect of training over an extended period of time.

9.6. Modification of method for specifying beat component

9.6.1. Maximally simplified case

In the preceding fourth embodiment, the beat frequency component is specified according to the flow chart in FIG. 24. However, when the processing capacity of CPU 308 is not sufficient, then the processing for specifying the beat frequency component may be simplified as follows.

Figure 25:
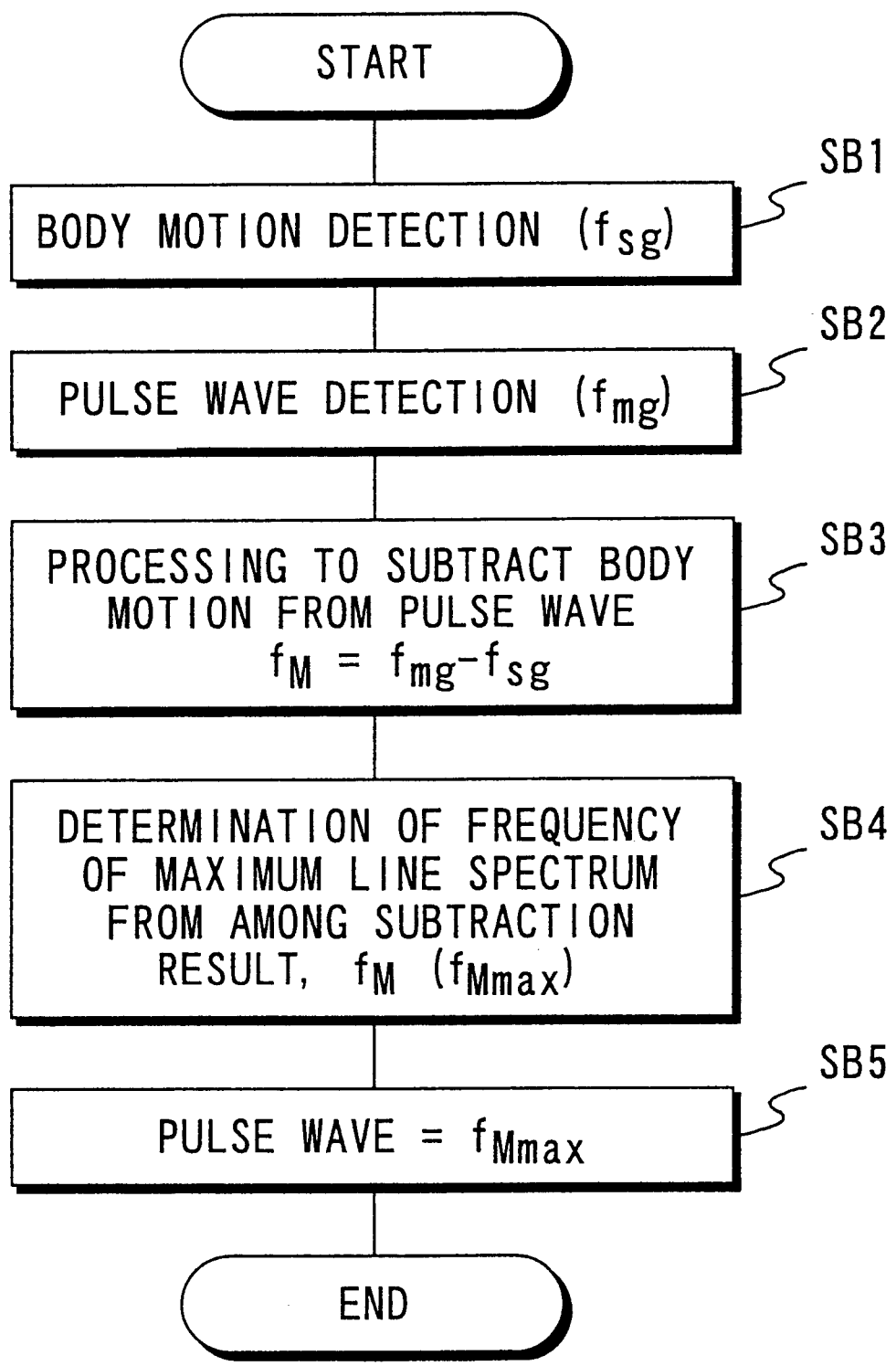
FIG. 25 is a flow chart showing an example of a method for specifying the pulse wave component using pulse/pitch detector 22.

FIG. 25 is a flow chart showing an example of the method for specifying the beat component from pulse/pitch detector 22.

In this figure, in step SB3, CPU 308 carries out a pulse wave-body motion subtraction operation (i.e., $f_M = f_{mg} - f_{sg}$) to extract the frequency component which is present only in the beat signal. In step SB4, CPU 308 specifies the maximum frequency component from the extracted pulse wave component $f_M$. The specified $f_{Mmax}$ is the beat frequency component. There is a difference in the change in the harmonic wave component in the beat component and the body motion component due to the exercise load, so that the change in the beat component is well expressed. This is caused by the change in heart functioning, and is well expressed in the change in stroke volume per beat (SV). Further, as is well known, beat rate increases as the exercise load becomes greater.

9.6.2. Specifying the maximum body motion component as the second harmonic wave In the preceding Embodiment 4, the maximum body motion component was initially assumed to be the second harmonic wave, and an investigation was carried out to determine whether or not this assumption was correct (steps SD2, SD4). The probability that this assumption was correct is viewed to vary according to conditions such as type of exercise (running, swimming, race walking, etc.), the movement of the user s body during the particular type of exercise, and the like. Accordingly, provided that the conditions are understood, then the probability that the assumption is correct becomes extremely high. In this case, the processing for verifying the assumption may be omitted.

Figure 26:
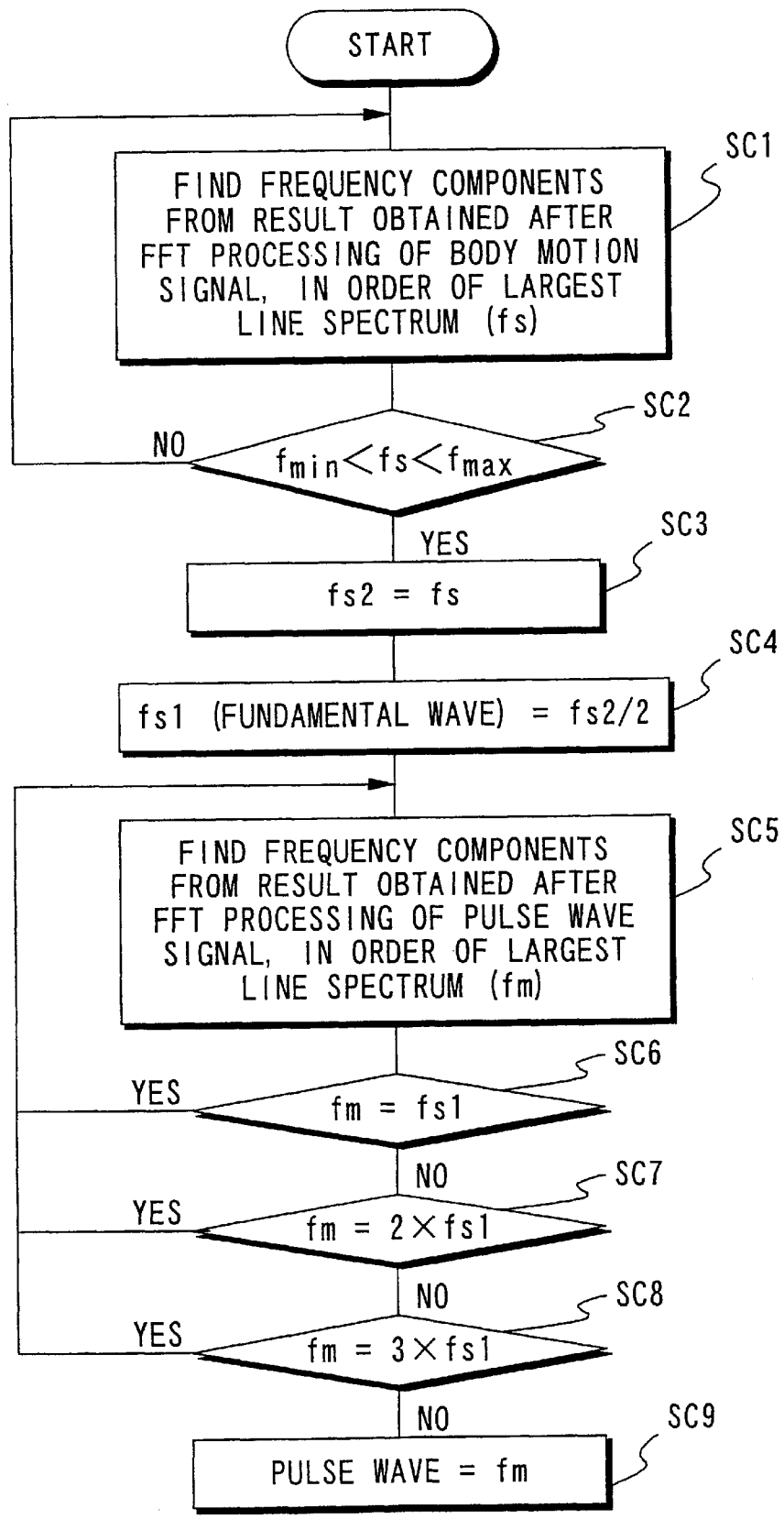
FIG. 26 is a flow chart showing an example of a method for specifying the pulse wave component using pulse/pitch detector 22.

FIG. 26 is a flow chart showing an example in which the method for specifying the pulse wave component has been simplified based on this principle.

In steps SC1~SC3 in the example shown in this figure, CPU 308 specifies the frequency $f_{s2}$ of the second harmonic wave from body motion sensor 302, which is relatively easily detected as a body motion component.

In the case where the exercise is running, for example, the $f_{min}$ shown in step SC2 is defined to be 2 Hz, i.e., the frequency which is the lower limit at which the second harmonic wave for running motion appears.

On the other hand, the $f_{max}$ shown in step SC2 is the frequency which is determined by the sampling rate for the A/D conversion. When the sampling frequency is set to 8 Hz, then, according to the sampling theorem, the maximum frequency at which the original waveform reappears is automatically determined to be 4 Hz.

The maximum line spectrum in this $f_{max}$ to $f_{min}$ range is specified as the second harmonic wave $f_{s2}$ of the body motion component.

Next, in step SC4, CPU 308 obtains frequency $f_{s1}$ of the fundamental wave of body motion.

In steps SC5~SC8, CPU 308 removes the pulse wave component which coincides with the fundamental wave ($f_{s1}$), second harmonic wave ($2xf_{s1}$), and third harmonic wave ($3xf_{s1}$) of the body motion component from the spectrum detected by pulse wave sensor 301.

In step SC9, the maximum frequency component remaining after the above-described removal process is specified as the pulse wave fm.

9.7. Modification of processing allotment

In the preceding fifth through seventh embodiments, the pulse rate at pulse wave measuring device 1A which attaches to the arm is calculated, and the obtained pulse rate is relayed to the data processing device 1B side. However, it is also acceptable to send the detected pulse wave signal as is to data processor 1B, and calculate the pulse rate from the pulse wave signal at data processor 1B.

What is claimed is:

1. A maximum oxygen intake quantity estimating device incorporated in a portable article carried by a test subject comprising:

exercise intensity detecting means for detecting an exercise intensity of the test subject;

beat rate detecting means for detecting a beat rate of the test subject;

recording means for recording in advance a relationship of a maximum oxygen intake quantity corresponding to exercise intensity and beat rate; and calculating means for determining the maximum oxygen intake quantity corresponding to the beat rate detected by said beat rate detecting means and exercise intensity from the relationship of the maximum oxygen intake quality stored in said recording means.

2. A maximum oxygen intake quantity estimating device according to claim 1, further comprising:

input means for inputting
  (1) at least one of body weight and stride of the test subject, and
  (2) body height of the test subject; and pitch detecting means for detecting a running pitch of the test subject;

wherein, said exercise intensity detecting means defines a product of one of an input stride value and a stride value determined from said body height, and the running pitch detected by said pitch detecting means as distance run, and detects as said exercise intensity a value obtained by multiplying said product by the body weight input by said input means and converting to a per unit time value.

3. A maximum oxygen intake quantity estimating device according to claim 2, further comprising:

altitude measuring means for measuring altitude at least at a first time and a second time;

wherein, said exercise intensity detecting means determines a slope from the detected altitude difference of the first time and the second time, and revises the exercise intensity by correcting the stride according to said slope.

4. A maximum oxygen intake quantity estimating device according to claim 1, further comprising notifying means for prompting the test subject to increase exercise intensity.

5. A maximum oxygen intake quantity estimating device according to claim 1, further comprising:

input means for inputting a body weight of the test subject and and one of a body height and a stride of the test subject;

pitch detecting means for detecting a running pitch of the test subject; and notifying means for prompting the test subject to increase exercise intensity;

wherein said exercise intensity detecting means defines a product of one of an input stride value, and a stride value determined from the body height, and a detected pitch as a distance run by the test user, and detects as the exercise intensity a value obtained by multiplying said product by the body weight and converting to a per unit time value, and revises the exercise intensity by correcting stride to match the detected pitch.

6. A maximum oxygen uptake quantity estimating device according to claim 1, further comprising means for recording the measured maximum oxygen intake quantity over a specific period of time, and notifying the user of change in said maximum oxygen uptake quantity.

7. A portable pulse wave measuring device which is incorporated in a portable device, having a pulse wave detecting means for detecting a pulse wave in the body, and which sends and receives information including said pulse wave to and from an information processing device provided external to said portable device, said portable pulse wave measuring device comprising:

communications means for transferring said pulse wave, subtracting a body motion component from said pulse wave and relaying pulse wave information obtained from said pulse wave to said information processing device by optical signals.

8. A portable pulse wave measuring device according to claim 7, wherein said communications means comprises a connector means which can attach in a freely releasable manner to one of a connector member in which said communication means is formed and a connector member in which a transmitter is formed which transmits said pulse wave information to said information processing device.

9. A portable pulse wave measuring device according to claim 7, wherein said communications means comprises a connector means which can attach in a freely releasable manner to a connector member in which said communication means and said transmitter for transmitting said pulse wave information to said information processing device are formed in a unitary manner.

10. A portable pulse wave measuring device according to claim 8 or claim 9, wherein said communications means comprises a receiving element which is formed in a unitary manner with said transmitter for receiving information sent from said information processing device by optical signals.

11. A portable pulse wave measuring device according to claim 7, wherein:

said pulse wave detecting means comprises pulse wave sending means for sending said pulse wave by optical signals; and said communications means comprises connector means which can attach in a freely releasable manner to a connector member in which a receiving element which receives said pulse wave through optical signals and a transmitter which transmits said pulse wave information to said information processing device are formed in a unitary manner.

12. A portable pulse wave measuring device according to claim 11, wherein said receiving element receives information sent in a wireless manner by means of an optical signal from said information processing device.

13. A portable pulse wave measuring device according to claim 12, wherein said optical signal is near-infrared light, and said receiving element has a filter for blocking visible light from said optical signal, and a light receiving element for near-infrared rays, which receives the optical signals which have passed through said filter.

14. A portable pulse wave measuring device according to claim 9, or claim 11, wherein said connector member is fixed in place to said connector means.

15. An exercise workout support device comprising:

recording means for recording relationship of correspondence between maximum oxygen intake quantity and pulse rate;

input means for inputting the maximum oxygen intake quantity estimated based on lactic acid threshold value;

read out means for reading out pulse rate corresponding to said input maximum oxygen uptake quantity from said recording means;

correcting means for correcting said read out pulse rate from said readout means based on at least one of an age of a user, a surrounding temperature and a desired exercise intensity;

calculating means for calculating upper and lower limits centered about said corrected pulse rate; and notifying means for notifying a test subject of said upper limit and said lower limit, wherein said maximum oxygen uptake quantity is estimated based on lactic acid threshold value.

* * * * *

UNITED STATES PATENT AND TRADEMARK OFFICE
CERTIFICATE OF CORRECTION

PATENT NO.    : 6,241,684 B1
DATED         : June 5, 2001
INVENTOR(S)   : Kazuhiko Amano et al.

It is certified that error appears in the above-identified patent and that said Letters Patent is hereby corrected as shown below:

<u>Title page,</u>
Item [56], FOREIGN PATENT DOCUMENTS, add:
-- 59-149128    8/1984(JP) --
-- 7-246255     9/1995(JP) --
-- 7-246254     9/1995(JP) --
-- 5-154116     6/1993(JP) --
-- 2-80029      3/1990(JP) --
-- 7-178064     7/1995(JP) --
-- 6-44270      2/1994(JP) --
-- 60-104285    6/1985(JP) --
-- 3-5405       1/1991(JP) --
-- 5-212136     8/1993(JP) --

Signed and Sealed this

Seventeenth Day of September, 2002

*Attest:*

*Attesting Officer*

JAMES E. ROGAN
*Director of the United States Patent and Trademark Office*